United States Patent [19]

Dubach et al.

[11] Patent Number: 5,788,713
[45] Date of Patent: Aug. 4, 1998

[54] METHOD AND APPARATUS FOR STEREOTACTIC IMPLANTATION

[75] Inventors: Mark Dubach, Seattle; Yves Nievergelt, Spokane, both of Wash.

[73] Assignee: University of Washington, Seattle, Wash.

[21] Appl. No.: 918,680

[22] Filed: Aug. 21, 1997

Related U.S. Application Data

[63] Continuation of Ser. No. 278,786, Jul. 22, 1994, abandoned.
[51] Int. Cl.[6] .................. A61B 19/00; A61M 25/088; A61M 25/09
[52] U.S. Cl. .................. 606/130; 606/108; 604/264; 604/280; 604/164; 604/116
[58] Field of Search .................. 604/264, 280, 604/164, 116; 128/654–8; 606/78, 108, 129, 130

[56] References Cited

U.S. PATENT DOCUMENTS

| | | | |
|---|---|---|---|
| 4,026,296 | 5/1977 | Stoy et al. | 604/96 |
| 4,306,562 | 12/1981 | Osborne | 604/280 |
| 4,386,602 | 6/1983 | Sheldon et al. | 128/4 |
| 4,552,554 | 11/1985 | Gould et al. | |
| 4,563,181 | 1/1986 | Wijayarathna et al. | 604/280 |
| 4,613,324 | 9/1986 | Ghajar | |
| 4,773,431 | 9/1988 | Lodomirski | |
| 4,869,247 | 9/1989 | Howard, III et al. | |
| 4,883,474 | 11/1989 | Sheridan et al. | 604/280 |
| 4,892,538 | 1/1990 | Aebischer | |
| 4,986,814 | 1/1991 | Burney et al. | 604/264 X |
| 5,045,072 | 9/1991 | Castillo et al. | 604/280 |
| 5,069,226 | 12/1991 | Yamauchi et al. | 128/772 |
| 5,078,713 | 1/1992 | Varney | 606/23 |
| 5,102,391 | 4/1992 | Palestrant | 604/116 |
| 5,106,627 | 4/1992 | Aebischer | |
| 5,125,888 | 6/1992 | Howard et al. | |
| 5,154,723 | 10/1992 | Kubota et al. | 606/130 |
| 5,191,898 | 3/1993 | Millar | 604/160 X |
| 5,205,289 | 4/1993 | Hardy et al. | 128/653.1 |
| 5,211,644 | 5/1993 | VanBeek et al. | 604/264 |
| 5,257,998 | 11/1993 | Ota et al. | 606/130 |
| 5,267,982 | 12/1993 | Sylvanowicz | 604/280 X |
| 5,269,759 | 12/1993 | Hernandez et al. | 604/280 X |
| 5,309,913 | 5/1994 | Kormos et al. | 128/653.1 |
| 5,322,509 | 6/1994 | Rickerd | 604/280 X |
| 5,324,286 | 6/1994 | Fowle | 606/23 |
| 5,389,100 | 2/1995 | Bacich et al. | 604/280 X |
| 5,389,101 | 2/1995 | Heibrun et al. | 606/130 |
| 5,411,476 | 5/1995 | Abrams et al. | 604/96 X |
| 5,417,669 | 5/1995 | Castaneda et al. | 604/264 |
| 5,439,464 | 8/1995 | Shapiro | 604/264 X |

OTHER PUBLICATIONS

Emerich et al., "A Novel Approach to Neural Transplantation in Parkinson's Disease: Use of Poly–Encapsulated Cell Therapy" 1992.

Levy et al, "Curved Biopsy Needle for Stereotactic Surgery: A Technical Note", Neurosurgery, 1984.

Myers, "Injection of Solutions into Cerebral Tissue: Relation between Volume and Diffusion," *Physiol. Behav.*, 1:171–174 (1966).

Blacker et al., "Hypotonia Accompanying the Neurosurgical Relief of Essential Tremor," *J. Nerv. Ment. Dis.*, 147:1, pp. 49–55 (1968).

(List continued on next page.)

*Primary Examiner*—Danton D. DeMille
*Attorney, Agent, or Firm*—Townsend and Townsend and Crew LLP

[57] ABSTRACT

A device for the percutaneous localization of a foreign object in a body has a base collar mount and one or more movable collar mounts all located on at least one perpendicular guide rail. The base collar mount has a guide-tube cannula affixed to it. A series of tubings and wire lengths extend through the guide-tube cannula as the movable collar mounts are advanced. As the tubings and wire are exposed from the guide-tube cannula, they assume their native curvature thus forming a compound trajectory for the insertion of a foreign object in a body.

41 Claims, 8 Drawing Sheets

OTHER PUBLICATIONS

Lassers, et al., "Removal of an Iatrogenic Foreign Body from the Aorta by Means of a Ureteric Stone Catcher," *Am. Heart J.*, 73:375–378 (1970).

O'Neill, et al., "Pervenous Retrieval of Embolized Catheters from the Right Heart and Pulmonary Arteries," *Am. Heart J.*, 98:287–293 (1979).

Levy, et al., "Curved Biopsy Needle for Stereotactic Surgery: A Technical Note," *Neurosurgery*, 15:82–85 (1984).

Ungerstedt, "Measurement of Neurotransmitter Release by Intracranial Dialysis."*Meaurement of Neurotransmitter Release In Vivo*, C.A. Marsden, Ed., pps. 81–105, John Wiley & Sons, Ltd. (1984).

Dubach et al., "Techniques for Improving Stereotaxic Accuracy in *Macaca fascicularis*," *J. Neurosci. Meth.*, 13:163–169 (1985).

Sendelbeck, et al., "Spatial Distribution of Dopamine, Methotrexate and Antipyrine During Continuous Intracerebral Microperfusion," *Brain Res.*, 328:251–258 (1985).

Tossman, et al., "Microdialysis in the Study of Extracellular Levels of Amino Acids in the Rat Brain," *Acta Physiol. Scand.*, 128:9–14 (1986).

Bankiewicz, et al., "Hemiparkinsonism in Monkeys after Unilateral Internal Carotid Artery Infusion of 1–Methyl–4–Phenyl–1,2,3,6–Tetrahydropyridine (MPTP)," *Life Sci.*, 39:7–16 (1986).

Dorros, et al., "Angiography of the Internal Mammary Artery via the Contralateral Brachial Artery," *Cathet. Cardiovasc. Diagn.*, 13:138–140 (1987).

Ungerstedt, et al., "In Vivo Microdialysis –A New Approach to the Analysis of Neurotransmitters in the Brain."*Life Sciences*, 41:861–864 (1987).

Ostrup et al., "Continuous Monitoring of Intracranial Pressure with a Miniaturized Fiberoptic Device," *J. Neurosurg.* 67:206–209 (1987).

Fellmeth et al., "Ultralong, Reverse–Curve Angiographic Catheter," *Radiology*, 172:872–873 (1989).

Winn et al., "An Encapsulated Dopamine–Releasing Polymer Alleviates Experimental Parkinsonism in Rats," *Exper. Neurol.*, 105:244–250 (1989).

Winn, et al., "Brain Tissue Reaction to Permselective Polymer Capsules," *J. Biomedical Materials Res.*, 23:31–44 (1989).

Crutchfield et al., "Evaluation of a Fiberoptic Intracranial Pressure Monitor," *J. Neurosurg.* 72:482–487 (1990).

Kordower et al., "NGF–like Trophic Support from Peripheral Nerve for Grafted Rhesus Adrenal Chromaffin Cells," *J. Neurosurg.*, 73:418–428 (1990).

Dubach, "Accurate Stereotactic Injection by Radially Curved Injection Needles," *Neurosurgery*, 29:144–149 (1991).

Kroin et al., "Dopamine Distribution and Behavioral Alterations Resulting from Dopamine Infusion into the Brain of the Lesioned Rat," *J. Neurosurg.*, 74:105–111 (1991).

Moura, et al., "A Direct Method for Least–Squares Circle Fitting," *Computer Physics Communications*, 64:57–63 (1991).

Dubach, "Distribution of Intracerebrally Injected Dopamine as Studied by a Punch–Scintillation Modeling Technique," *Neuroscience*, 45:103–115 (1991).

Emerich et al., "A Novel Approach to Neural Transplantation in Parkinson's Disease: Use of Polymer–Encapsulated Cell Therapy," *Neurosci. Biobehav. Rev.*, 16:437–447 (1992).

CMA/Microdialysis Catalog, pp. 7 and 8 (Jan., 1994).

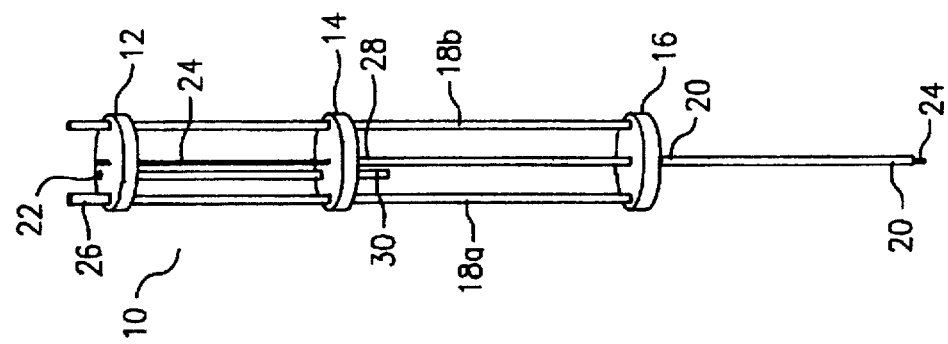
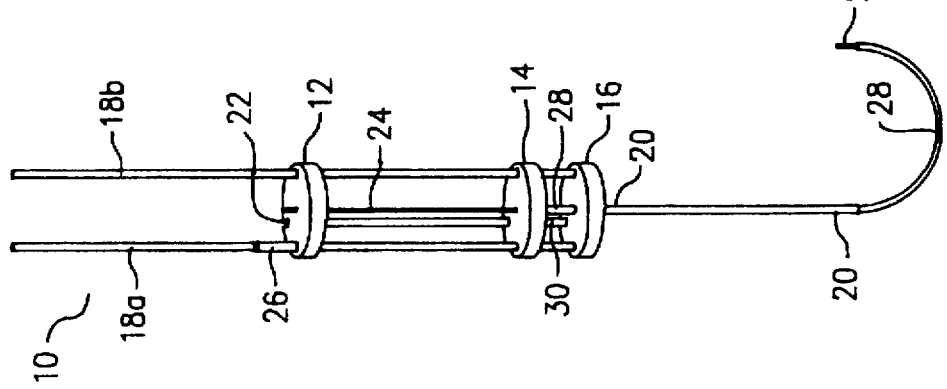
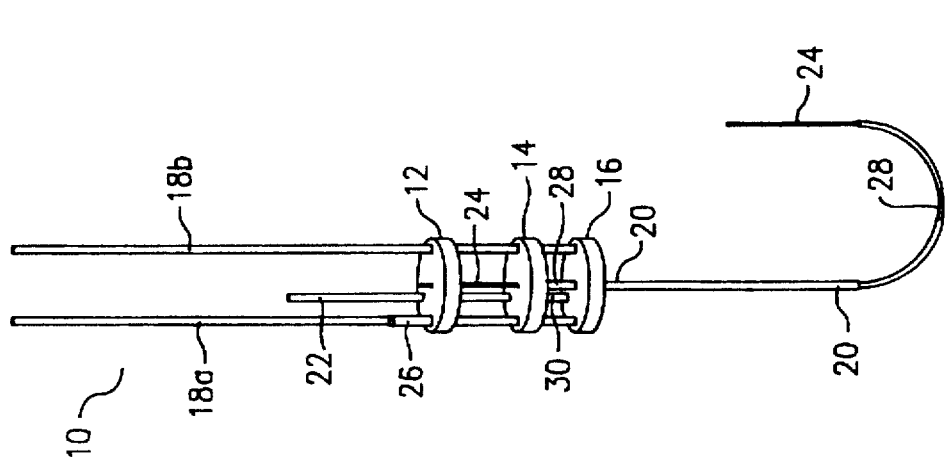

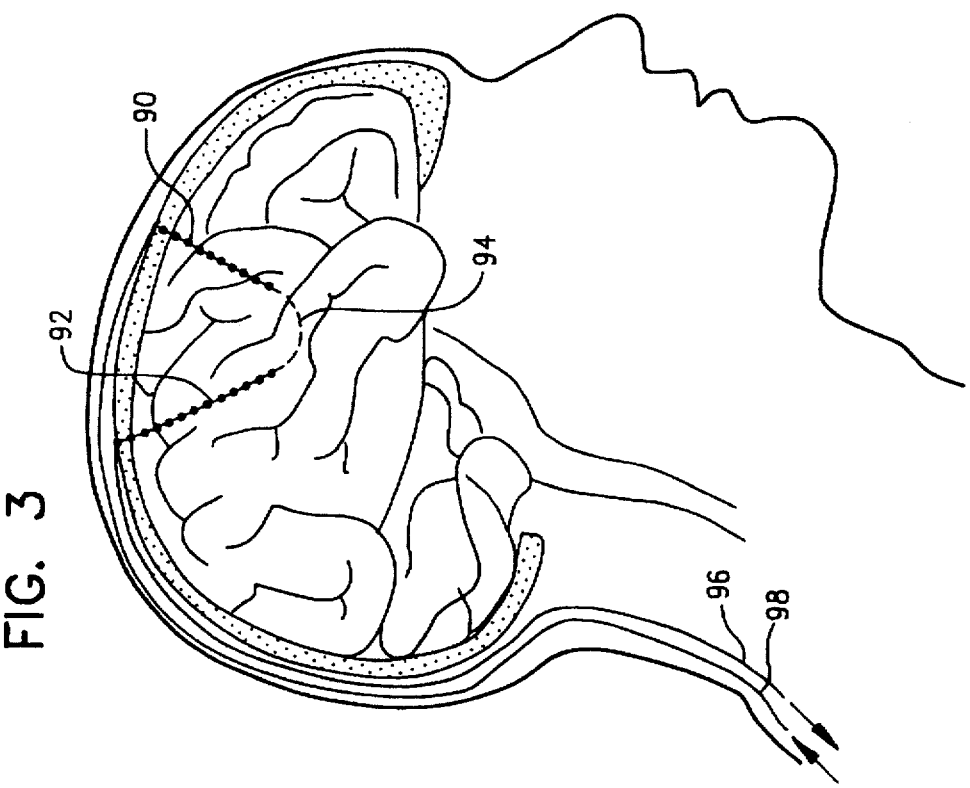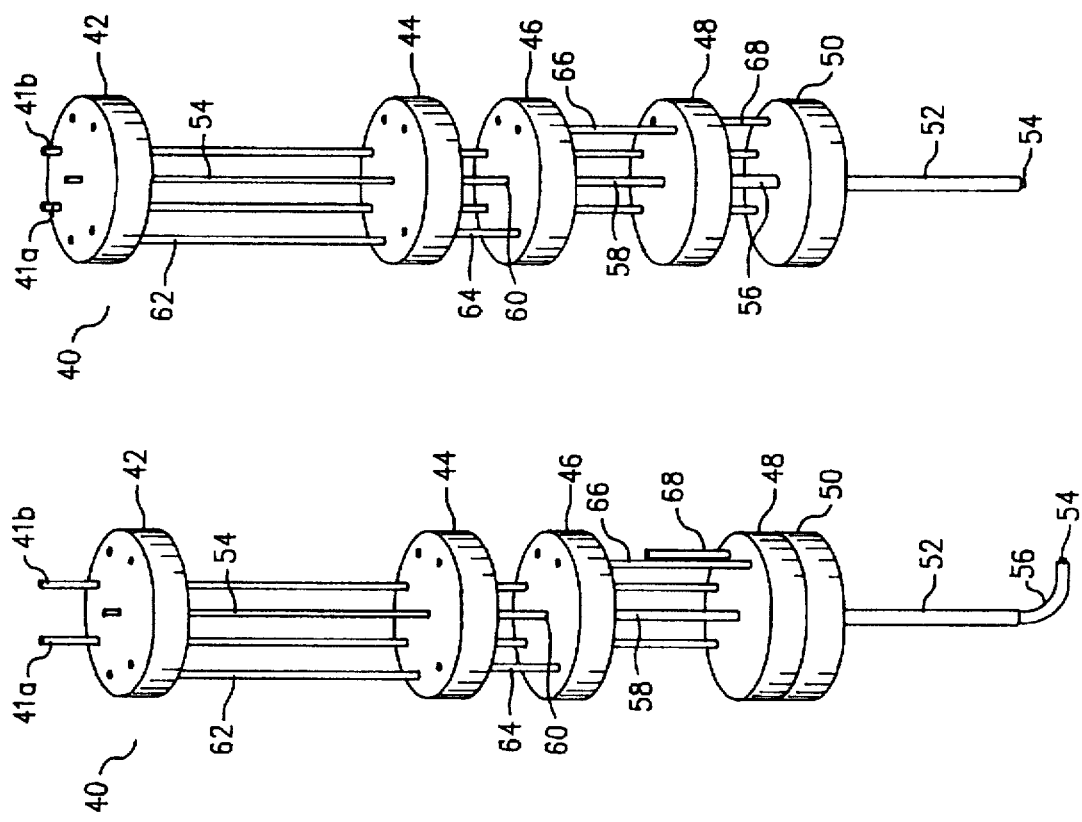

METHOD AND APPARATUS FOR STEREOTACTIC IMPLANTATION

This application in a continuation of Ser. No. 08/278,786 filed Jul. 22, 1994, now abandoned.

GOVERNMENT SUPPORT

The U.S. government may have certain rights in the invention pursuant to a grant received from the U.S. National Institutes of Health.

BACKGROUND OF THE INVENTION

The present invention provides methods for stereotactic implantation of foreign bodies in organs or tissues. More particularly, the present invention provides methods for stereotactic implantation of a foreign body along a compound straight and curvilinear trajectory through an organ or tissue. The compound trajectory may be identified by computer programs. The present invention allows short-term or long-term access to a disease locale by minimally invasive surgical techniques.

Surgeons commonly treat localized disease processes by altering and, in some instances, by destroying biological tissue in a disease locale. In most cases, surgical treatment does not provide for chronic direct application of biological agents or other means of modulating or monitoring local tissues. Surgeries that involve such treatment have inherent limitations. In many clinical settings in which foreign matter is implanted for therapeutic purposes, such as hip replacements, major surgery is required. Overlying tissues and target tissues must be incised and opened to gain access to the implantation site. In some instances, surgeons may leave an implanted vascular catheter for localized administration of a drug. This type of treatment is generally limited, however, because the catheter delivers drug into a vessel that enhances delivery to the general circulation, the tumor may extend beyond the drainage of the vessel, or delivery is limited to the point of egress at the tip of the tubing. For example, localized chemotherapy for liver cancer can be provided by catheterizing the hepatic artery. The catheter must follow the route of hepatic artery. Infused drugs contact the entire drainage of the artery, eventually joining the general circulation in the inferior vena cava.

In the treatment of brain lesions, such as malignancies, single vessels will often not perfuse the entire tumor bed. Further, the blood brain barrier acts to limit the delivery of drug across the capillary wall. As delivery of the drug is limited, the tumor receives low doses even during localized infusions of high doses. Attempts to directly apply medications to intracranial lesions are limited by the difficulties and dangers inherent in intracranial access. Localized radiotherapy of gliomas (brachytherapy), for example, requires the passage of straight tubes through brain tissue to reach the tumor site. Often several such tubes are required to treat the entire tumor. Such treatments are limited because many delivery tubes may be required to reach the necessary points for insertion of the radioactive material. Also, linear percutaneous approaches to deep tissues are often impossible if the path traverses, or lies close to, critical structures that may be injured by catheter placement.

Temporarily concealed retrieval hooks and loops of various designs have been used in angiography and urology. For example, O'Neill and Joseph describe retrieval of severed catheter tips from pulmonary arteries by means of a catheter from which a retractable loop could be extended (*Am. Heart J.*, 98, pp. 287–93, 1979). Similarly, ureteral stones have been snared and removed by catheters having extendable curved elements (Lassers, *Am. Heart J.*, 73, pp. 375, 1970).

Looped and curved catheters of various designs have been used in angiography for placement of catheter tips into branched vessels. (See, e.g., Fellmeth et al., *Radiology*, 172, pp. 872–3, 1989; and Dorros and Lewin, *Cathet. Cardiovasc. Diagn.*, 13, pp. 138–140, 1987). These angiographic and related techniques employed natural body channels for the placement of the catheters, i.e., blood vessels and the urinary tract.

Concealed wire loops have been used in disconnection neurosurgeries, but for the inherent purpose of cutting tissue rather than penetrating with minimal damage as is desirable for treating localized lesions deep within normal parenchyma. The concealed curve is a loop that expands outward from a housing, thus shearing across tissue for the purpose of cutting fiber tracts (leukotomy), rather than cleanly piercing along its trajectory. For example, such a technique has been employed for thalamotomy to relieve essential tremor (Blacker et al., *J.Nerv. Ment. Dis.*, 147, pp. 49–55, 1968). Another type of probe has been introduced into the brain for a different purpose, without the intention of damaging diseased tissue. A flexible optical fiber tipped with a pressure transducer has been inserted into the brain for the measurement of intracranial pressure (Ostrup et al., *J. Neurosurg.* 67, pp. 206–207, 1987; Crutchfield et al., *J. Neurosurg.* 72, pp. 482–487, 1990). Such devices have not been passed clear through the brain from the entry point to an exit point, and have not been used for drug application. No method is available for specifically selecting an extended region deep within the brain or body affected by a disease.

Many localized disease processes may be treated by systemically administered drugs. Oral or parenteral administration provides access to the general circulation and, thus, to the diseased site. Such systemic therapy is effective for certain diseases. Many other diseases are not amenable to such treatment, however. Treatment may be limited by toxic side effects at other sites in the body. Treatment may be limited by the metabolism and elimination of the drug before it reaches the intended site.

Molecular biology is leading to the emergence of new classes of therapeutic agents, many of which are biologically too delicate and too expensive to be useful as peripherally administered drugs. Means of delivering such substances in clinically practicable ways are a major concern. This is especially true for the many currently untreatable diseases of the brain. Therapeutics often cannot cross the blood brain barrier in sufficient quantities to produce effective tissue concentrations. Likewise from a research perspective, the understanding of brain function is impeded by the fact that substances can be administered locally only to a single "point site", and only acutely or subchronically. Long-term studies of localized drug effects are hampered by the inflammatory processes associated with normal implanted cannulae, which are stiff and usually metallic. The experimental implantation of encapsulated tumor cells that produce neuroactive substances (Emerich et al., *Neurosci. Biobehav. Rev.*, 16, pp. 437–447, 1992) is limited by inherent dangers of implanting tumor cells, by the lack of means to regulate or to alter the flow of substances after implantation, and by the limitation to point sites of implantation. The effects of drugs in anatomically distant brain locales are not easily tested by systemic delivery or by existing means of administration to a point site.

What is needed in the art are means for accessing extended local regions of organs, which may be vascularized by several different and often inaccessible vessels. Preferably, the means would allow for accurate percutaneous access to disease sites that would not compromise sensitive structures, such as points in the brain stem, as well as allow for chronic localized therapy of a lesion. Quite surprisingly, the present invention fulfills these and other needs.

SUMMARY OF THE INVENTION

The present invention provides devices having a proximal end and a distal end for percutaneous localization of a foreign object in a body (FIGS. 1A–1C and 2A–2E). The devices generally comprise a plate-like base collar mount having a proximal surface, a distal surface rigidly affixed to at least one perpendicular guide rail, and a channel between the proximal and distal surfaces through which channel a guide-tube cannula extends from the proximal surface of the base collar; a plate-like first movable collar mount slidably located on each guide rail rigidly affixed to a curved first extendable cannula having a proximal end and a distal end, wherein the distal end of the first extendable cannula is affixed to the first movable collar in a channel through the first movable collar and the proximal portion of the first extendable cannula is in the guide-tube cannula; and a plate-like second movable collar mount slidably located on each guide rail rigidly affixed to a second extendable cannula or wire having a proximal end and a distal end, wherein the distal end of the second extendable cannula or wire is affixed to the second movable collar in a channel through the second movable collar and the proximal portion of the second extendable cannula or wire is in the first extendable cannula; wherein proximal sliding of the first movable collar will extend the first extendable cannula through the proximal end of the guide-tube cannula and proximal sliding of the second movable collar will extend the second extendable cannula or wire through the proximal end of the first extendable cannula. The devices may have additional movable collar mounts and extendable cannulae. Generally, the path of percutaneous access will be a compound trajectory comprising straight and curvilinear segments.

Methods for percutaneous placement of foreign substances at desired locations in the body are also provided. The methods generally comprise positioning a device as described above at a predetermined location and orientation over the body; advancing the guide-tube cannula into the body, covering an original predetermined distance; advancing the first extendable cannula into the body, covering a first additional predetermined distance; optionally advancing a second or more additional coaxial cannulae, covering a second or more additional predetermined distances; and introducing the foreign substance through the final extendable cannula to the desired location in the body. The desired position in the body is generally identified by a diagnostic imaging technique (e.g., magnetic resonance imaging, computerized tomography, ultrasound, or the like). The foreign substance is often a pharmaceutical compound or catheter.

Methods for treating localized diseased regions in a body are also provided. The methods involve stereotactically implanting a foreign object along a compound trajectory through a desired region in a host. The methods generally comprise identifying an arcuate or helical curvilinear path through the host, which curvilinear path may traverse the region to be treated; inserting a guide-tube cannula through a surface of the host to meet the curvilinear path; advancing a curved cannula or wire, preformed to match the curvilinear path, through the guide-tube cannula into the host along the curvilinear path to a predetermined point; optionally advancing one or more additional coaxial cannulae, the last of which may be a solid wire, through the curved cannula to the surface of the host; attaching a foreign object to the final cannula or wire; withdrawing each wire or cannula through the host in reverse order, whereby the foreign object traverses the compound trajectory including the insertion path of each wire or cannula in the host. The foreign object may include a cryogenic probe, an electrode or electric device such as chips or wires, or a semipermeable catheter. The catheter may be used for analyzing substances passing into the catheter from the brain, for exposing the brain region to therapeutic compounds elaborated by cells introduced into the catheter, or for adjustably exposing the brain region to therapeutic compounds placed directly in the catheter itself. The treated disease may be a tumor, Parkinson's disease, schizophrenia, depression, Alzheimer's disease, epilepsy, spinal cord trauma, or the like. The therapeutic compound may be a dopamine agonist, a neurotrophic factor, or any of a wide variety of other agents.

Kits for placing catheters along compound trajectories in a host are also provided. The kits generally comprise a device of the present invention and a catheter. The catheter is typically semipermeable. Often the catheter is polyacrylonitrile polyvinylchloride copolymer. Pumps may also be supplied in the kits.

Methods for determining a compound trajectory through a localized or extended region of a body for selective placement of a therapeutic modality are also provided. The methods generally comprise identifying the body region in a diagnostic image of tissue surrounding the region; assigning a coordinate system to the body; identifying three or more non-collinear points in the region; identifying the circle that intersects the three points, or a helix that passes near the four or more points; determining the radius, center and plane of the circle, or the formula of the helix; identifying points of intersection of the circle or helix with predetermined parallel sections through the body; identifying two points of tangency at which entry and exit segments of the compound trajectory contact an arc of the circle or helix; determining the direction cosines of the entry and exit segments; calculating the arcuate distance between each pair of circle or helix intersection points on consecutive sections, from one point of tangency to the other; summing the arcuate distances; identifying points of intersection of the entry and exit segments with the predetermined parallel sections through the body; calculating the linear distances between each pair of entry or exit segment intersection points on consecutive sections; summing the linear distances; determining the compound trajectory of the path as the points of intersection of the arcuate and linear segments with the predetermined parallel sections; redefining the trajectory in the coordinate system of the diagnostic image; and displaying the trajectory in the diagnostic image. The diagnostic image is generally a magnetic resonance image, computerized tomographic image, ultrasound image, or the like. The body region is often in the brain, and may be, for example, a brain tumor or a portion of the basal ganglia.

BRIEF DESCRIPTION OF THE DRAWINGS

FIGS. 1A–1C illustrate a device of the present invention having two cannulae and one wire, in the fully extended position, partially extended position, and non-extended position.

FIGS. 2A–2E illustrate a device of the present invention having four cannulae and one wire, in the fully extended position, partially extended positions, and non-extended position.

FIG. 3 illustrates the position of a catheter placed by the methods of the present invention for treatment of a deep site in the brain.

DESCRIPTION OF SPECIFIC EMBODIMENT

Figure 2A:
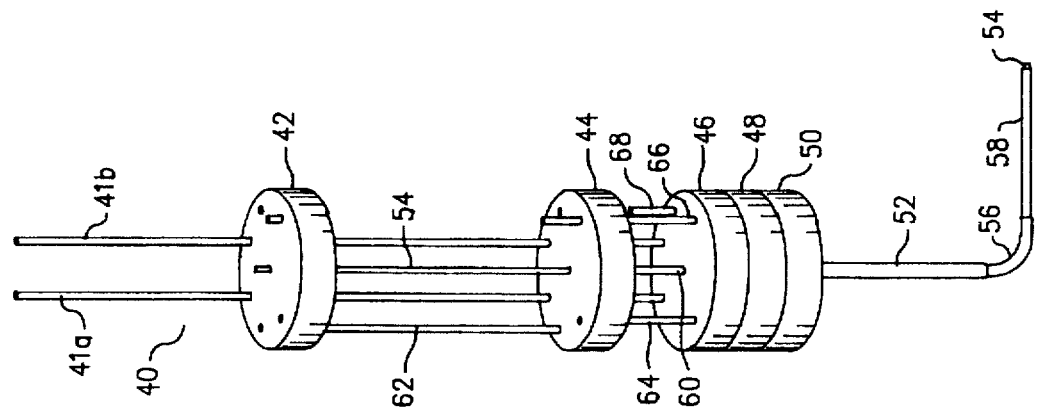
Figure 2B:
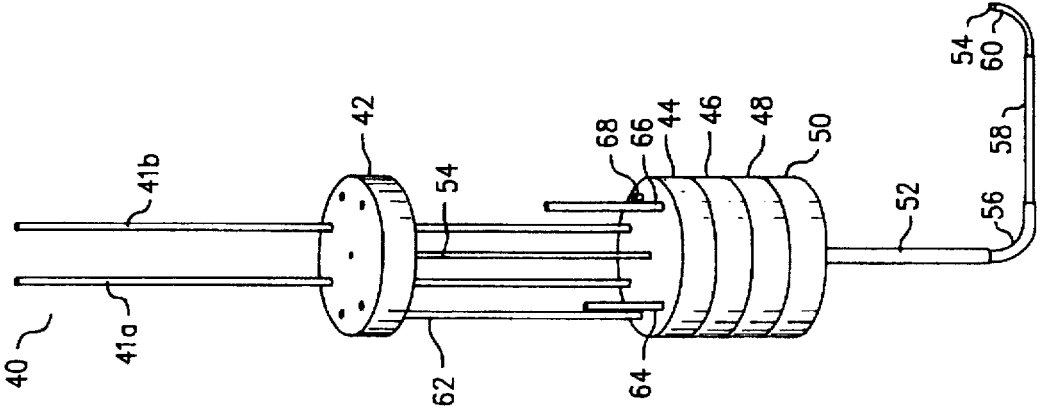
Figure 2C:
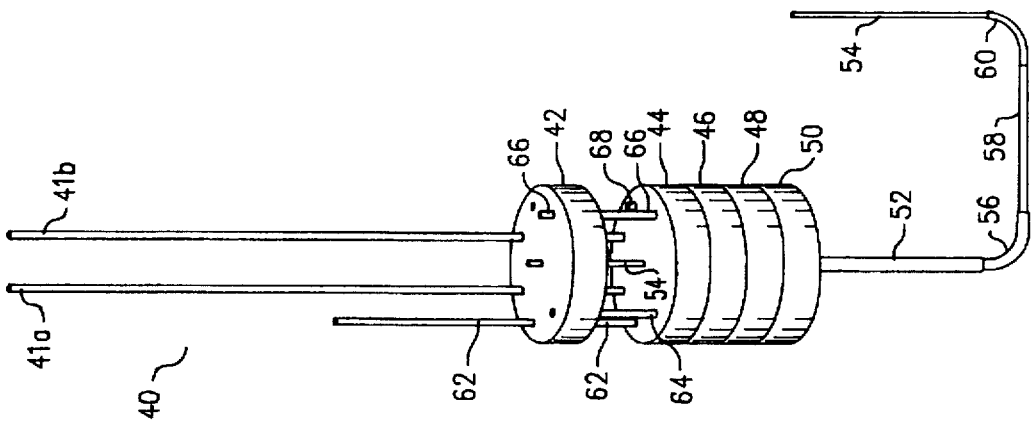

The present invention provides devices and methods for determining curvilinear paths through three dimensional structures. The methods allow clinicians to select a targeted group of points in a compact or extended region identified in an imaging study, such as MRI, CT, or ultrasound, and to link the points by a helical curvilinear path. The targeted region may be remote from the surface of the body. The region may have a tortuous shape, or may need treatment near its margins, requiring access from a helical arc or a coil of several periods. In other cases the region will have a simpler shape and will require access centrally, so that often the helix will be circular. After determining the helical path, devices of the present invention may be constructed to provide a means for implanting a catheter through the targeted region and treating the targeted region including each of the selected points. The parameters of the helix provide the parameters employed in shaping the curved cannulae as described above.

One specific embodiment of the present invention will now be described by referring to FIG. 1, where an implantation tool 10 is shown. The implantation tool 10, in one embodiment, includes an upper collar mount 12, a middle collar mount 14, and a lower collar mount 16. These collar mounts are each formed, e.g., out of plastic and are plate-like in shape. The mounts serve as handles and as guides for mounting and manipulating other components of the implantation tool 10. The lower collar mount 16 is fixed to a pair of stainless steel guide rails 18a–b, while the upper and middle collar mounts 12, 14 are slidably connected to the guide rails.

The tool further consists of a guide-tube cannula 20 which is affixed to the lower collar mount 16 and which slidably receives a length of curved nitinol tubing 28. Although other materials may be used for the tubing and wiring of the tool, nitinol, a nickel-titanium alloy, is preferred as it exhibits great flexibility and a strong shape memory. The length of curved nitinol tubing 28 is, in turn, affixed to the middle collar mount 14 and slidably receives a length of nitinol wire 24. The length of nitinol wire 24 is attached to the upper collar mount 12. A gauge 26 for the curved nitinol tubing 28 is provided on the upper collar mount 12, slidably fitting around the guide rail 18a. Another gauge 22 is provided for the nitinol wire 24. The gauge 22 is affixed to the middle collar mount 14 and adjustably affixed to the upper collar mount 12. Finally, a stop 30, attached to the middle collar mount 14, is used for the curved nitinol tubing 28.

The basic operation of an implantation tool 10 is shown in FIGS. 1A–C. In FIG. 1A the tool 10 is positioned for the maximum extension of the nitinol wire 24 and tubing 28. As the upper collar mount 12 moves away from the middle collar mount 14, as in FIG. 1B, the nitinol wire 24 retracts into the curved nitinol tubing 28. When the upper collar mount 12 reaches the end of the gauge 22, it is tightened in position on the gauge 22. When the upper collar mount 12 and the middle collar mount 14 move together away from the lower collar mount 16, the curved nitinol tubing 28 and the nitinol wire 24 retract into the guide-tube cannula 20. The gauges ensure that the tubing and wire do not retract too far. The gauge 22 also ensures that the upper and middle collar mounts 12, 14 move in unison when the curved nitinol tubing 28 and the nitinol wire 24 are retracted together into the guide-tube cannula 20. The properties of nitinol allow the curvature of the curved tubing and the wire to be precisely controlled, even after residing within the straight guide-tube cannula 20. As the tool 10 is extended into the body, the tubing and wire emerge from the guide-tube cannula 20 and express their native curvature and the device thus defines a distinctive pre-planned trajectory. The curvature may be programmed into the nitinol using means well-known in the art.

At maximal extension, the nitinol wire protrudes from the body. Semipermeable tubing can be fastened to its tip so that when the tool 10 is retracted the semipermeable tubing is drawn through the body along the pre-planned trajectory.

Figure 4:
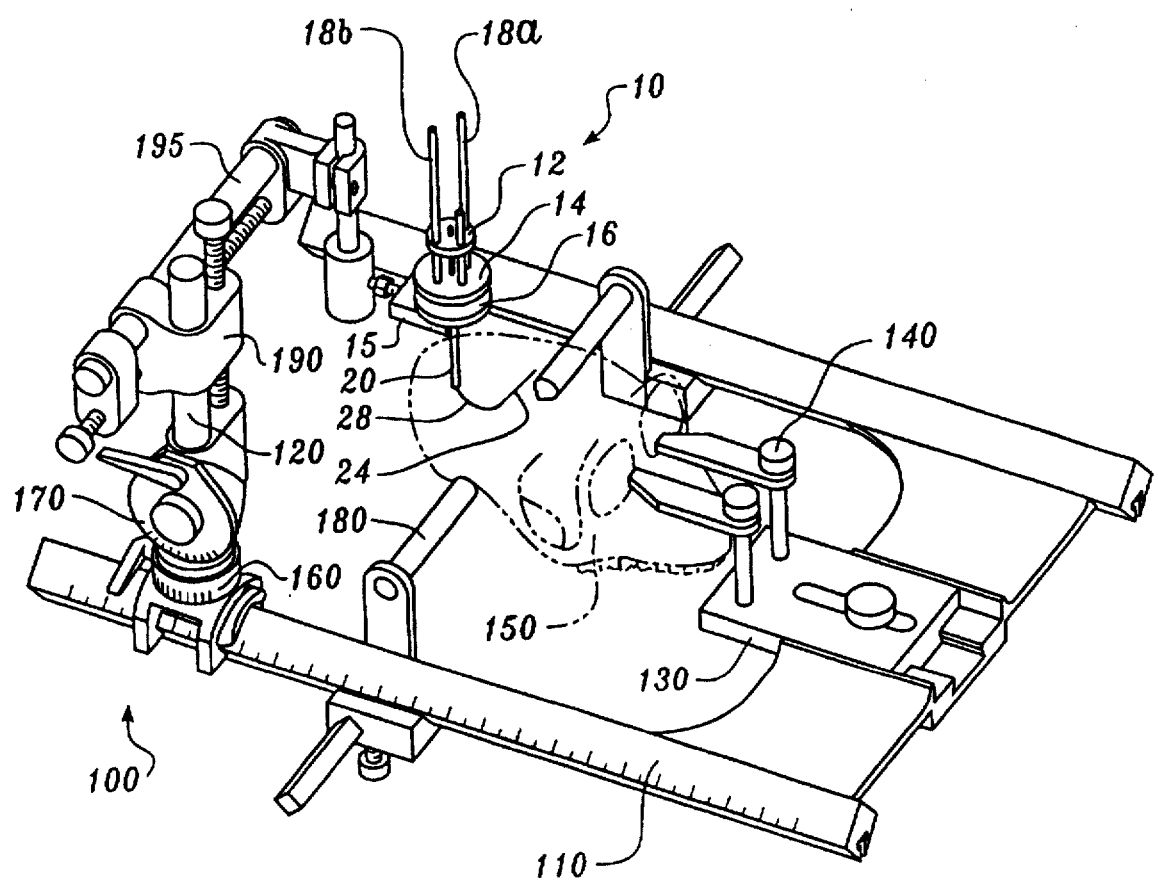
FIG. 4 illustrates a perspective view of a device of the present invention having two cannulae and one wire in the fully extended position, mounted on a Kopf stereotactic instrument with PED and ROT adjustments at the standard square and upright starting positions.

Those skilled in the art will appreciate that the curvatures and relative lengths of the wires and tubing may be modified as needed for specific applications. Skilled practitioners will also recognize that the implantation tool 10 may be used in conjunction with a variety of stereotactic instruments, such as a Kopf stereotactic device as shown in FIG. 4. The Kopf stereotactic device is available from David Kopf Instruments, Tujunga Calif., and is used as an example platform in the discussion herein.

Another specific embodiment of an implantation tool 40 is shown and described by referring to FIGS. 2A–E. In this embodiment, five elements are utilized to provide additional trajectory options for reaching remote and otherwise inoperable sites in the brain or other parts of the body. The tool includes five collar mounts 42–50. The top four collar mounts 42–48 are slidably attached to two stainless steel guide rails 41a–b. The bottom collar mount 50 is fixed to the ends of the guide rails 41a–b. A guide-tube cannula 52 is attached to the bottom collar mount 50 and slidably receives a first length of curved nitinol tubing 56. This first length of curved tubing 56 is attached to the next highest collar mount 48 and receives a length of straight nitinol tubing 58. The straight tubing is attached to the next highest collar mount 46 and receives a second length of curved nitinol tubing 60 which in turn is attached to the next highest collar mount 44. A length of nitinol wire 54 slides within the second length of curved nitinol tubing 60. The length of wire 54 is attached to the upper collar mount 42. Thus, as is depicted in FIG. 2A, as the collar mounts are moved together, the wire 54, the second curved nitinol tubing 60, the straight nitinol tubing 58, and the first curved nitinol tubing 56 are all extended and exposed past the end of the guide-tube cannula 52. When the collar mounts are moved apart, as shown in FIG. 2E, the tubing and wire are retracted within the guide-tube cannula.

The implantation tool 40 also includes a variety of gauges attached to each of the collar mounts. For example, the length of straight nitinol tubing 58, which is attached to collar mount 46, has a corresponding gauge 66, which is adjustably attached to collar mount 46. Further, the gauge is also attached to the next-lowest collar mount 48. Observation of the gauge 66 as the collar mount 46 is raised enables the length of straight nitinol tubing 58 to be retracted the proper distance. Its tip is flush with the tip of the first curved nitinol tubing 56 when the top of its collar mount 46 is flush with the top of the gauge 66, as shown in FIG. 2D. Tightening the attachment of collar mount 46 on gauge 66 ensures that collar mounts 46 and 48 will subsequently move in unison during the retraction of the first curved nitinol tubing 56. Each of the other lengths of nitinol has a corresponding gauge. The nitinol wire 54 is gauged by gauge 62. The first and second lengths of curved nitinol tubing are gauged by gauges 68 and 64, respectively. Those skilled in the art will realize that the lengths of the gauges will be chosen to correspond to the necessary lengths of nitinol tubing and wiring required for a specific procedure. The calculation and selection of such lengths and curvatures will be discussed infra in conjunction with a description of the methods for planning a trajectory of the three part implantation tool.

Referring now to FIG. 3, a view of a human cranium having an implant inserted by a device according to the present invention is shown. The figure relates the compound trajectory which must be followed in order to make such an implant. An implant with a front, non-permeable portion is shown as item 90. The implant also includes a back non-permeable portion 92 and a semipermeable portion 94. The interrupted line format of portions 90, 92, 94 in the drawing indicate that they pass deeply through the substance of the brain, rather than lying at its surface. Return and input lines 96, 98 are also shown which connect the example implant with a pump 99. These lines are solid in the drawing, to indicate that they lie outside the brain, just under the skin. Those skilled in the art will appreciate that other foreign objects may also be inserted using the device and method of the present invention, including a flexible catheter ending deep in the brain or body without a return line, various pharmaceutical compounds, cryogenic probes, or the like.

Methods for planning a trajectory for a device of the present invention are described below. The implantation tool is temporarily advanced in stages along the planned compound trajectory, into the brain or another organ or region of the body, until its leading tip emerges again; then a length of implantable tubing is connected to the tip and drawn into position as the telescoping implantation tool is retracted. Various software packages were utilized in conjunction with a portion of the steps to be described. Those skilled in the art will recognize that methods for the calculation and planning of such a trajectory may differ in detail from those utilized.

The methods will be described in nine parts. The first part (Machine-dependent Input) will begin with imaging scans, proceed to three original target points, and add other measurements and user-input adjustments to provide to the Core Section. The next two parts (Core Section) will begin with the three original target points, incorporate two additional user-input tangent points, and proceed to the final series of calculated points all along the trajectory. The fourth, fifth, sixth, and seventh parts (Machine-dependent Output) will begin with the calculated trajectory and proceed to its display, its improvement and recalculation if necessary, the angular and translational settings it prescribes for the stereotactic equipment, and the specifications it provides for the implantable tubing and the implantation tool. The eighth part (Alternative Input Methods) will return to the beginning and describe a few of the many possible alternative input techniques that have been developed in the prototype. The ninth part (Fitting a Three-Dimensional Helical Curve to a Set of Points) will present an alternative to the second part, for the case in which a three-dimensional helix is desired and more than three target points have been entered.

I. Machine-dependent input Algorithms

From an imaging scanner (MRI, CAT, ultrasound, etc.), to an accessible file format representing its images, to a display with a graphical user interface (GUI), to inputs in the form of selected pixels, to the selection of three original target points. Additional hardware parameters and user-input adjustments.

1. A first step is to establish physically an orthogonal coordinate system. The manner by which this system is established is immaterial, as long as it can be effectively reproduced in both the radiological and surgical environments. It is necessary to configure equipment that can be used to align the imaging and surgical coordinate systems. To accomplish an accurate placement of implanted tubing, it is important for the body to be in the same fixed position in the imaging machine and in the surgical context. There are a number of ways to align the two systems, depending on the targeted part of the body and on the appropriate and available equipment. One useful way is illustrated below.

The example described herein reflects the development of the technique of the present invention in the context of nonhuman primate neurosurgery, making use of a standard stereotactic instrument fixed at the external auditory meati and the inferior orbital ridge. Those skilled in the art will appreciate that the method and apparatus of the present invention is preferably used in conjunction with tools allowing implantation in human organs and tissue. The nonhuman primate stereotactic instrument is described as a convenient example.

The origin at which this system is zeroed (called earbar zero) is a point midway between the points at which the stereotactic earbars contact the bony external auditory meatus. The line between these two contact points is one of the axes (the ML axis) of the coordinate system. A second axis (the AP axis) passes through earbar zero and a point on the sagittal plane at the level of the inferior orbital ridge (its superior surface). Together, the ML axis and the AP axis define a standard plane, which is known to classical craniometry as the Frankfurt plane, or to tomographic radiology as an axial plane. The third axis (the DV axis) is orthogonal to both the ML and AP axes, passing through earbar zero and through the cranium above earbar zero. The plane orthogonal to the ML axis is the midline sagittal plane. The plane orthogonal to the AP axis is known to tomographic radiology as the horizontal plane, or to classical neuroanatomy as the coronal plane. The utility of the method and the algorithms is not limited, however, to the brain stereotactic context. More generally, in the summary statements and in the formula derivations presented below, the following terminology conventions are respected:

earbar zero=origin
ML axis=X axis
DV axis=Y axis
AP axis=Z axis
coronal plane=DV/ML plane=XY plane
sagittal plane=DV/AP plane=YZ plane
axial plane=ML/AP plane=XZ plane The following sign conventions are also respected in the formula derivations presented below. The X values along the ML axis are positive to the left of earbar zero, negative to the right. The Y values along the DV axis are positive above earbar zero, negative below. The Z values along the AP axis are positive in front of earbar zero, negative behind. The convention that requires this sign designation was set out in order to conform to the standard examination of coronal sections in neuroanatomy. It permits the surgeon to examine coronal sections as if viewing the brain from in front of the face, and in that situation to have the view on the right (patient's left) positive and the view on the left (patient's right) negative.

The stereotactic device (Kopf stereotactic instrument, #1404, David Kopf Instruments, Tujunga Calif.) (FIG. 4) fixes the cranium in place by four contacts, two at the bony external auditory meati (earbars) and two fixed against the inferior orbital ridges of the eyes (eyebars). The stereotactic device for nonhuman primate magnetic resonance imaging (MRI) developed at the Regional Primate Research Center (RPRC, University of Washington, Seattle, Wash.) fixes the cranium in the same manner. In both cases, the plane in which these four bony landmarks reside (the Frankfurt plane) is typically held parallel to the plane of the arms of the stereotactic instrument, but it can be adjusted if necessary by rotating the cranium on the earbars and adjusting the eyebars (Dubach et al., *J. Neurosci. Meth.*, 13, pp. 163–169, 1985) to a higher or lower position. As a rule, the eyebars are set to the same height as the earbars, but other variations are acceptable as long as the settings can be reproduced on both devices; the bony landmarks must be in the same position for scanning and for surgery. The stereotactic device for the imaging scanner is mounted in the imaging field in a fixed position such that, if eyebars and earbars are set to the same height, the Frankfurt plane containing these landmarks is parallel to the axial plane of the imaging field. The mount is also designed to place the cranium's midline sagittal plane in the center of the imaging field. Therefore, if the cranium were properly and perfectly positioned, and if the imaging scanner always centered its images at the same point, no registration points would need to be entered.

2. A second step is to configure equipment that can be used to interface between the imaging machine and the analytic algorithms that plan the trajectory. Again, there are a number of ways for accomplishing this. One useful way is illustrated below.

When the imaging machine generates a video picture, that picture is the expression of an underlying data file. Such a file, converted to a TIF file in the rectangular format as described below, is a series of numbers (of magnitude 0–254 inclusive) representing gray-scale values of pixels. The first pixel in the data portion of the file is the pixel in the upper left-hand corner, the second is adjacent to its right, the third is to the right of that, and so on to the end of a line of 256 pixels. The 257th pixel is on the left just below the first pixel, starting another row of 256 pixels proceeding to the right. There are 256 such rows, from the top to the bottom. The origins of the imaging stereotactic coordinate system and the surgical stereotactic coordinate system, on the other hand, are in the center. Because of the structure of a TIF file, it is most straightforward to define for the scan a TIF coordinate system with its origin at the upper left-hand corner of the picture, with X values (ML) increasing toward the right of the picture, and Y values (DV) increasing toward the bottom of the picture.

In one specific embodiment, software may be utilized in order to assist in the selection of input points. For example, the following may be used:

(1) A conversion program available as part of the imaging facility converts each file, containing data from a coronal tomographic slice, from its native imaging scanner format to a rectangular TIF file format.

(2) An FTP network protocol, run from an 80486 microcomputer, may transfer the file onto the 80486 computer.

(3) An 80486 conversion program (such as those available at the RPRC, implemented in Microsoft Visual BASIC) can be used to put the data into a 256×256 format, and to query the user to set the gray-scale in such a way as to make full use of 255 shades of gray (omitting use of the brightest shade).

(4) The file may then be displayed by a commercial image-display package (Adobe Photoshop), for visual observation. Any pixel in the grid can be highlighted to the brightest gray-scale shade.

(5) An 80486 program (which may, for example, be implemented in Microsoft Visual BASIC) can then be used to survey the modified TIF file to find highlighted points, convert each point from its sequential position in the TIF file to its TIF coordinates as defined above, and pass the list of points into a text file. The text file may then be utilized as input information for analysis.

3. A third step, given these configurations, is to register the imaging stereotactic coordinate system with the surgical stereotactic coordinate system assumed by the subsequent algorithms. This registration is accomplished by informing the algorithms of the location of landmarks in the imaging system, so that input from and output to images can be properly expressed within the algorithms.

In practice, the imaging machine does not center its images at a standard single point, so at least one point is necessary for registration. In practice, furthermore, the positioning of the subject is not perfect, so that more points are required for registration. A total of eight registration points are entered. An imaging stereotactic device may contain channels of oil in the earbars, which can be perceived in the pictures it creates, on the basis of a display on the computer monitor, a single point (LeftEarML, LeftEarDV, LeftEarAP) is entered for the left earbar, and another (RightEarML, RightEarDV, RightEarAP) for the right earbar, marking the coronal slice and the ML/DV location of the pixel nearest to the corner of the earbar, which is more specifiable and more faithfully rendered by the imaging scanner than other points along the channels. It is always best, however, to determine a set of landmarks from a position close to the targeted position; the earbar points are well outside the cranium, and the location of the midline sagittal plane in the image can vary significantly from one recording session to another. Therefore, two points are entered along the midline of the coronal section through each original target point, one point at a relatively dorsal position along the midline (e.g., UpMidP1ML, UpMidP1DV, UpMidP1AP) and the other at a relatively ventral position along the midline (e.g., LoMidP1ML, LoMidP1DV, LoMidP1AP).

4. A fourth step is to enter the three original target points.

There are many different ways to proceed in this step. (See Part VIII for some alternatives.) One way is to acquire the three original target points, (PT1ML, PT1DV, PT1AP), (PT2ML, PT2DV, PT2AP), and (PT3ML, PT3DV, PT3AP), in the manner described above for the earbar points. Along with each target point, two points on the midline in each corresponding section are also acquired, as described above.

The points acquired in Steps 3 and 4 can be summarized:
(LeftEarML, LeftEarDV, LeftEarAP)
(RightEarML, RightEarDV, RightEarAP)
(PT1ML, PT1DV, PT1AP)
(UpMidP1ML, UpMidP1DV, UpMidP1AP)
(LoMidP1ML, LoMidP1DV, LoMidP1AP)
(PT2ML, PT2DV, PT2AP)
(UpMidP2ML, UpMidP2DV, UpMidP2AP)
(LoMidP2ML, LoMidP2DV, LoMidP2AP)
(PT3ML, PT3DV, PT3AP)
(UpMidP3ML, UpMidP3DV, UpMidP3AP)
(LoMidP3ML, LoMidP3DV, LoMidP3AP)

5. A fifth step is to convert the input points from pixel units to millimeter units and to place them in the stereotactic coordinate system used by the Core Algorithms.

Again, there are a number of ways to do this. One useful way is illustrated below.

The tilt and translation of the imaging coordinate system is detected and compensated on the basis of the line between the eyebars and the midline of each slice containing an original target point. First, for the earbars, in the TIF coordinate system, the line (in the coronal plane) connecting the two earbar points has the general formula:

$$Y = m*X + b \quad (1)$$

or:

$$Y = EarbarSlope*X + EarbarIntercept \quad (2)$$

The slope of the line is calculated as $(\Delta Y/\Delta X)$, the change in Y from one entered earbar point to the other, divided by the change in X:

$$EarbarSlope = (LeftEarDV - RightEarDV)/(LeftEarML - RightEarML) \quad (3)$$

The intercept (EarbarIntercept) with the Y axis (the left-hand margin of the TIF file, off to the right of the brain) can be derived by substituting (3) in (2):

$$Y = ((LeftEarDV - RightEarDV)/(LeftEarML - RightEarML))*X + EarbarIntercept \quad (4)$$

rearranging to obtain:

$$EarbarIntercept = Y - ((LeftEarDV - RightEarDV)/(LeftEarML - RightEarML))*X \quad (5)$$

and then substituting X and Y values from one of the earbar points (LeftEarML, LeftEarDV, LeftEarAP) in (5):

$$EarbarIntercept = LeftEarDV - ((LeftEarDV - RightEarDV)/(LeftEarML - RightEarML))*LeftEarML \quad (6)$$

The same derivation provides the coefficients in the formula for the line connecting the upper and lower points entered from the midline on the slice containing the second original target point (or, in the same manner, the midlines of the slices containing the first and third original target points).

$$MidP2Slope = (UpMidP2DV - LoMidP2DV)/(UpMidP2ML - LoMidP2ML) \quad (7)$$

$$MidP2Intercept = LoMidP2DV - ((UpMidP2DV - LoMidP2DV)/(UpMidP2ML - LoMidP2ML))*LoMidP2ML \quad (8)$$

The AP position of the earbars in the MRI picture is calculated as the average of the two earbar AP values:

$$EBZeroAP = (RightEarAP + LeftEarAP - RightEarAP)/2 \quad (9)$$

The field of view (FOV) in centimeters and the slice thickness (SliceThickness) of the tomographic slices are provided by the imaging scanner. Given that the standard display in the TIF file is a 256×256 grid, and that it represents the entire field of view (FOV×FOV centimeters), the edge of each square pixel in the grid can be calculated in millimeters:

$$PixelSize = (FOV*10)/256 \quad (10)$$

The position of the second target point can now be translated into terms of millimeters from earbar zero. Its AP position is measured as the distance of its section from EBZeroAP, and is adjusted by the SliceThickness factor:

$$AP_B = SliceThickness*(Pt2AP - EBZeroAP) \quad (11)$$

Its ML position within its section is defined as its distance to the midline, the line between the points (UpMidP2ML, UpMidP2DV, UpMidP2AP) and (LoMidP2ML, LoMidP2DV, LoMidP2AP). This distance can be written in general, for the point $(x_0, y_0)$ and the line $(AX+BY+C=0)$ as:

$$d = |Ax_0 + By_0 + C|/SQRT(A^2 + B^2) \quad (12)$$

(See, Taylor, *Calculus With Analytic Geometry*, Prentice Hall, Englewood Cliffs, N.J., p. 272, 1959)

The formula for a line used above in the derivation of the slope and intercept of the midline, rearranged from (1), was:

$$m*X - Y + b = 0 \quad (13)$$

In this formula as written, the coefficients (from (7) and (8)) are:

$$A = MidP2Slope = (UpMidP2DV - LoMidP2DV)/(UpMidP2ML - LoMidP2ML) \quad (14)$$

$$B = -1 \quad (15)$$

$$C = MidP2Intercept = LoMidP2DV - ((UpMidP2DV - LoMidP2DV)/(UpMidP2ML - LoMidP2ML))*LoMidP2ML \quad (16)$$

Substitution of these coefficients in formula (12), and multiplication by the scale factor to convert from pixels to millimeters, provides:

$$ML_B = PixelSize*(MidP2Slope*Pt2ML - Pt2DV + MidP2Intercept)/SQRT(MidP2Slope^2 + 1) \quad (17)$$

The same derivation provides the formula for the DV position of the second target point, defined as its distance within its section from the line between the earbars:

$$DV_B = \text{PixelSize} * (\text{EarbarSlope} * Pt2ML - Pt2DV + \text{EarbarIntercept}) / \text{SQRT}(\text{EarbarSlope}^2 + 1) \quad (18)$$

The same reasoning leads to equations of the form of Equations (11), (17), and (18) to provide the positions of the first and third target points ($ML_A$, $DV_A$, $AP_A$) and ($ML_C$, $DV_C$, $AP_C$) in terms of millimeters from earbar zero. Note that no "EBZeroML" or "EBZeroDV" terms appear in (17) and (18) to match the "EBZeroAP" term in (11). This is because AP is defined as the position of a plane in a series of parallel planes, with a "starting plane" based on the earbar entries, while ML and DV are defined specifically as distances from a point to a line in the same plane; for DV, of course, this makes the assumption that the earbar line would be in the same position in the three target-point slices as in the earbar slices.

6. A sixth step is simply to pass on the GUI-entered points (as converted to millimeter units and referenced to earbar zero) to the Core Algorithms outlined in Parts II and III. Other input options, however, are also useful. The most obvious of these is to enter coordinates at the starting point of the Core Algorithms, without reference to imaging data. This would be the approach, for example, if the user were relying on a brain atlas, and this is expected to be a common approach for experimental applications involving rodents, which conform closely enough to a standard atlas, because of inbreeding, that imaging data on individuals may not be necessary. Other additional input options are described in Part VIII, "Alternative input methods".

One other variable to be entered by the user along with the original target points is SideArm, which indicates that the cannula-carrier is to be mounted on the right (−1) or left (+1) stereotactic arm. This variable of course has no effect on the Core Algorithms (Part II and Part III), but it is important to the positioning of stereotactic equipment (Part V and Part VI) used as an example herein.

7. A seventh step is to enter the physical characteristics of the coaxial elements (inner and outer diameters, cannula length) and collar mount elements (thickness) of the implantation tool. These parameters will not affect the trajectory itself, but they will affect the stereotactic positioning necessary to achieve the trajectory.

The three original target points (Part I, Step 4) and the two tangent points (Part III, Step 1) on the circle are necessary and sufficient for calculating the trajectory. Additional details must be entered, however, to enable the accurate expression of the trajectory by the implantation tool, and to enable construction of the tool and the implanted compound tubing. The approach of the guide-tube cannula to the arcuate portion of the trajectory depends on accounting for a fine detail in the alignment of the curved tubing within the straight cannula. This detail is the fact that the curvature of the tubing (e.g., nitinol tubing) will begin to express itself slightly before the tubing emerges from the cannula. Mathematically, the only way to avoid this circumstance is to assume that the inner diameter of the cannula and the outer diameter of the nitinol tubing are identical, which is not physically possible. Since the tubing, therefore, must be smaller than the cannula, it is important to account for the curvature of the tubing that is concealed in the tip of the cannula. A comparable situation exists, of course, for the straight wire (e.g., nitinol wire) as it emerges from the curved nitinol tubing. These details, although small, can have a substantial effect on the actual trajectory expressed by the implantation tool. The following values are provided:

$$LE = \text{length of the guide-tube cannula} \quad (1)$$

$$ID = \text{inner diameter of the guide-tube cannula} \quad (2)$$

$$OD = \text{outer diameter of the curved nitinol tube} \quad (3)$$

$$IDNitTube = \text{inner diameter of the curved nitinol tube} \quad (4)$$

$$ODNitWire = \text{outer diameter of the innermost nitinol wire} \quad (5)$$

Finally, the thickness of the collar mounts and the thickness of the cannula-carrier block in which the guide-tube cannula (and therefore the implantation tool as a whole) is mounted are necessary for calculating the required lengths of tubing in the implantation tool:

$$\text{CollarMountThickness} = \text{thickness of the collar mounts} \quad (6)$$

$$\text{MountingBlockThickness} = \text{thickness of the cannula-carrier block} \quad (7)$$

8. An eighth step is to make fine adjustments for the three initial target points.

In practical use, for various reasons, it is helpful to be able to add slight adjustments to the initial target points, whatever input method is employed. These adjustments may be made at the outset or, more commonly, when the trajectory is being visually evaluated and readjusted (Part IV Step 3).

FitRad, an optional small quantity to be added to the DVs of two target points, is a means of forcing the radius of the circle to a specific value. This conveniently permits matching the planned trajectory to the implantation tool available, for example. FitRad is an arbitrarily and empirically selected number that is added to the DV of target point 1 ($DV_A$) and to the DV of target point 3 ($DV_C$).

AvoidDivZero can be used to avoid a division-by-zero error for a trajectory that lies fully within a single coronal plane. AvoidDivzero is an arbitrarily and empirically selected very small number that is added to the AP of target point 1 ($AP_A$) and subtracted from the AP of target point 3 ($AP_C$). It can easily be made so small it has no practical effect on placement, but does permit the algorithms to proceed to calculate a very close approximation of the desired trajectory.

TiltFactor makes it possible to move the exit point slightly, to avoid a critical structure at the surface such as the sagittal sinus when the wire emerges. TiltFactor is an empirically selected small number added to the ML of target point 3 ($ML_C$).

II. Core Algorithms

From three points to a series of circle points.

1. A first step is to derive coefficients of the formula for the plane that contains the three original (non-collinear) target points ($ML_A$, $DV_A$, $AP_A$), ($ML_B$, $DV_B$, $AP_B$), and ($ML_C$, $DV_C$, $AP_C$) from Part I. Again, there are a number of ways for accomplishing this task. One useful way is illustrated below.

The general formula for a plane is:

$$H*X + I*Y + J*Z + K = 0 \quad (1)$$

(See, Love, *Elements of Analytic Geometry* MacMillan, NY, p. 136, 1940)

The coefficients for this general formula that specify the plane containing the circle (the "circle plane") can be calculated from the three given points in a number of ways. One efficient way is illustrated below:

Since all three points satisfy the general formula, one can substitute in (1) to get:

$$H*ML_A + I*DV_A + J*AP_A + K = 0 \quad (2)$$

$$H*ML_B + I*DV_B + J*AP_B + K = 0 \quad (3)$$

$$H*ML_C + I*DV_C + J*AP_C + K = 0 \quad (4)$$

Subtracting (2) from each of the other Equations (1), (3), and (4) gives:

$$H*(X-ML_A)+I*(Y-DV_A)+J*(Z-AP_A)=0 \quad (5)$$

$$H*(ML_B-ML_A)+I*(DV_B-DV_A)+J*(AP_B-AP_A)=0 \quad (6)$$

$$H*(ML_C-ML_A)+I*(DV_C-DV_A)+J*(AP_C-AP_A)=0 \quad (7)$$

This homogeneous system of three equations gives rise to a determinant which is an alternative formula for a plane:

$$\begin{vmatrix} (X-ML_A) & (Y-DV_A) & (Z-AP_A) \\ (ML_B-ML_A) & (DV_B-DV_A) & (AP_B-AP_A) \\ (ML_C-ML_A) & (DV_C-DV_A) & (AP_C-AP_A) \end{vmatrix} = 0 \quad (8)$$

Evaluation of this determinant can be used to deduce a set of values for the unknowns H, I, and J of the homogeneous system. This is done by evaluating the minor related to each term in the first row (see Taylor supra, pp. 522, 536):

$$H = \begin{vmatrix} (DV_B-DV_A) & (AP_B-AP_A) \\ (DV_C-DV_A) & (AP_C-AP_A) \end{vmatrix} \quad (9)$$

$$I = \begin{vmatrix} (ML_B-ML_A) & (AP_B-AP_A) \\ (ML_C-ML_A) & (AP_C-AP_A) \end{vmatrix} \quad (10)$$

$$J = \begin{vmatrix} (ML_B-ML_A) & (DV_B-DV_A) \\ (ML_C-ML_A) & (DV_C-DV_A) \end{vmatrix} \quad (11)$$

The fourth coefficient that corresponds to these is derived by substituting H, I, and J in Equation (2) and solving for K:

$$K=-(H*ML_A+I*DV_A+J*AP_A) \quad (12)$$

This is not, and does not need to be, a unique set of coefficients. Any multiple of the derived coefficients H, I, J, and K will be describing exactly the same plane (Equation (1)).

2. A second step is to find the center of the circle through these three original points.

Again, there are a number of ways to do this. One efficient way is illustrated below.

Since the center of any circle lies on the perpendicular bisectors of any triangle on it, we simply manufacture the perpendicular bisector planes of two of the edges of the triangle formed by the three original points, then solve the three equations (one for the plane containing the three original points and two for the perpendicular bisector planes).

The general formula for the distance (call it D) between two points $(x_2, y_2, z_2)$ and $(x_1, y_1, z_1)$ is:

$$D=\pm SQRT[(x_1-x_2)^2+(y_1-y_2)^2+(z_1-z_2)^2] \quad (1)$$

The general formulas for the direction cosines of a line between two points $(x_2, y_2, z_2)$ and $(x_1, y_1, z_1)$ are:

$$A=(x_1-x_2)/D \quad (2)$$

$$B=(y_1-y_2)/D \quad (3)$$

$$C=(z_1-z_2)/D \quad (4)$$

(See, Love supra, p. 129, and Protter et al., College Calculus with Analytic Geometry, Addison-Wesley, Reading, Mass., p. 538, 1964.)

The general formula for a plane, again, is:

$$AX+BY+CZ+E=0 \quad (5)$$

(See, Love supra, p. 136)

For a plane perpendicular to a line, the direction cosines of the line may be taken as the first three coefficients in the formula for the plane (Love supra, p. 137). Therefore the plane perpendicularly bisecting the line between the original target points $(ML_A, DV_A, AP_A)$ and $(ML_B, DV_B, AP_B)$ is described by the formula:

$$[(ML_A-ML_B)/D]*X+[(DV_A-DV_B)/D]*Y+[(AP_A-AP_B)/D]*Z+E=0 \quad (6)$$

Since the plane passes through the midpoint between the two points, this midpoint may be substituted in Equation (6) to give:

$$[(ML_A-ML_B)/D]*(ML_A+ML_B)/2+[(DV_A-DV_B)/D]*(DV_A+DV_B)/2+ \\ [(AP_A-AP_B)/D]*(AP_A+AP_B)/2+E=0 \quad (7)$$

Solving for E:

$$E=-\tfrac{1}{2}*[(ML_A^2-ML_B^2)+(DV_A^2-DV_B^2)+(AP_A^2-AP_B^2)]/D \quad (8)$$

Multiplying both sides of Equation (6) by $-D$, substituting E from (8), and rearranging gives:

$$(ML_B-ML_A)*X+(DV_B-DV_A)*Y+(AP_B-AP_A)*Z=\tfrac{1}{2}*[(ML_B^2-ML_A^2)+ \\ (DV_B^2-DV_A^2)+(AP_B^2-AP_A^2)] \quad (9)$$

Similarly, for points $(ML_C, DV_C, AP_C)$ and $(ML_B, DV_B, AP_B)$, $$(ML_C-ML_B)*X+(DV_C-DV_B)*Y+(AP_C-AP_B)*Z=\tfrac{1}{2}*[(ML_C^2-ML_B^2)+ \\ (DV_C^2-DV_B^2)+(AP_C^2-AP_B^2)] \quad (10)$$

The formula for the plane specified by the three points (coefficients given in Part II Step 1 Equations (9)–(12)), and the two formulas ((9) and (10)) for the perpendicular bisector planes between two pairs of these points, can be solved simultaneously to give the location of the center of the circle through the three points. Again, there are a number of ways to do this. One efficient way is illustrated below.

First, a matrix is designated consisting of the coefficients of the three planes:

$$\begin{vmatrix} H & I & J & K \\ A_1 & B_1 & C_1 & E_1 \\ A_2 & B_2 & C_2 & E_2 \end{vmatrix} = 0$$

Second, the planes are sorted to assure that a row with a leading zero (if it is present) is at the bottom, and another row with a leading zero (if it is present) is second up from the bottom.

Third, elementary row operations are performed (Hoffman et al., Linear Algebra, Prentice-Hall, Englewood Cliffs, N.Y., p. 6, 1961), each of which leaves the matrix row-equivalent to the original matrix, resulting in a row-reduced echelon matrix (Hoffman, supra, p. 12). The right-hand column of values in the solved matrix represents the desired simultaneous solution of the three equations, and therefore the center of the circle, designated herebelow as (xx, yy, zz).

3. A third step is to find the radius of the circle. This can be easily calculated as the distance from any one of the points to the center:

$$rad=SQRT((xx-ML_A)^2+(yy-DV_A)^2+(zz-AP_A)^2) \quad (1)$$

4. A fourth step is to use the coefficients of the formula for the plane (H, I, J, K), the coordinates of the center of the circle (xx, yy, zz), and the radius of the circle (rad) to determine the Y coordinate of each of the two points of intersection of the circle with an XY plane at an arbitrarily selected position along the Z axis.

Again, there are a number of ways to do this. One useful way is illustrated below.

The DV coordinate of the intersection of the circle with a coronal plane at $AP_{arctraj}$ can be calculated by the formulas below, where:

$$AA = H/SQRT(H^2+I^2+J^2)$$

$$BB = I/SQRT(H^2+I^2+J^2)$$

$$CC = J/SQRT(H^2+I^2+J^2)$$

$$DD = K/SQRT(H^2+I^2+J^2)$$

The formula for the circle plane is:

$$AA*X+BB*Y+CC*Z+DD=0 \quad (1)$$

The formula for the circle is:

$$(X-xx)^2+(Y-yy)^2+(Z-zz)^2=rad^2 \quad (2)$$

The formula for the coronal plane is:

$$Z=AP_{arctraj} \quad (3)$$

Substituting (3) in (1) produces:

$$AA*X+BB*Y+CC*AP_{arctraj}+DD=0 \quad (4)$$

Substituting (3) in (2) produces:

$$(X-xx)^2+(Y-yy)^2+(AP_{arctraj}-zz)^2=rad^2 \quad (5)$$

Solving (4) for X produces:

$$X=(-DD-BB*Y-CC*AP_{arctraj})/AA \quad (6)$$

Substituting (6) in (5) produces:

$$([(-DD-BB*Y-CC*AP_{arctraj})/AA]-xx)^2+(Y-yy)^2+(AP_{arctraj}-zz)^2=rad^2 \quad (7)$$

Resolving (7) in terms of Y produces $$a*Y^2+b*Y+c \quad (8)$$

where $$a=(BB^2/AA^2+1)$$

$$b=(-2*yy+2*BB*(xx+(CC*AP_{arctraj}+DD)/AA)/AA)$$

$$c=(yy^2+((-CC*AP_{arctraj}-DD)/AA-xx)^2+(AP_{arctraj}-zz)^2-rad^2)$$

Solving (8) for Y by using the quadratic equation gives two possible answers, corresponding to the DV coordinate at which the circle passes through the coronal plane above and below:

$$\text{above: } DV_{arctraj}=Y=(-b+SQRT(b^2-4*a*c))/(2*a) \quad (9)$$

$$\text{below: } DV_{arctraj}=Y=(-b-SQRT(b^2-4*a*c))/(2*a) \quad (10)$$

5. A fifth step is to repeat the same calculation for each of a series of planes parallel to the arbitrarily selected XY plane. This can be accomplished simply by repeating the formula many times over, once for each coronal plane, over the range of the AP limits of the circle, making the calculations twice for each plane to account for the upper and lower intersection points. The selection of coronal planes may be made arbitrarily. It is convenient, however, to select the imaging scanner series of planes, at an interval of SliceThickness between selected planes, supplemented by the planes at the most posterior and most anterior points on the circle (see Part VII Step 4). If an atlas is being used for entry of the original target points (see Part VIII Step 2), then planes shown in the atlas should be included.

6. A sixth step is to determine the X coordinate of each of the two points of intersection of the circle with each plane (in the series of XY planes parallel to the arbitrarily selected XY plane). Again, there are a number of ways to do this. One useful way is illustrated below.

Given that the AP of the coronal plane is designated $AP_{arctraj}$, and the previously calculated DV is designated $DV_{arctraj}$, the result follows simply from the substitution of these values in the formula for the circle plane:

$$AA*X+BB*Y+CC*Z+DD=0 \quad (1)$$

$$ML_{arctraj}=(-BB/AA)*DV_{arctraj}-(CC/AA)*AP_{arctraj}-(DD/AA) \quad (2)$$

III. Core Algorithms

From a series of circle points and two tangent points to a series of trajectory points.

1. A first step is to select a point at which the straight guide-tube cannula will first contact the circle, and a second point at which the straight wire will first lose contact with the circle. These two tangent points must be entered by the user.

There are a number of ways in which the two points might be designated. One useful way is for the user simply to select the AP values of two of the parallel coronal planes for which the circle's intersection points have been calculated. These points are designated as ($ML_{gtang}$, $DV_{gtang}$, $AP_{gtang}$) and ($ML_{wtang}$, $DV_{wtang}$, $AP_{wtang}$), indicating their X, Y, and Z coordinates, respectively.

2. A second step is to derive the direction cosines of the tangent to the circle, in the plane of the circle, at each of these two points. Again, the derivation could be performed in a number of different ways. One useful way is illustrated below.

Since the tangent is perpendicular to the radius of the circle to its contact point, it must also lie in a plane normal to that radius. The formula for this plane is first derived, then the formula for the plane of the circle is restated, and the two formulas are solved simultaneously to give direction cosines that specify the tangent line.

The radius of the circle that reaches the contact point of the tangent is a line, and therefore has direction cosines derivable from the coordinates of two points ($x_1$, $y_1$, $z_1$) and ($x_2$, $y_2$, $z_2$) on the line and the distance d between them (Protter et al., supra, p. 538, and Love, supra, p. 129):

$$AlphaDirecCos=(x_2-x_1)/d \quad (1)$$

$$BetaDirecCos=(y_2-y_1)/d \quad (2)$$

$$GammaDirecCos=(z_2-z_1)/d \quad (3)$$

Substituting the designations for the center of the circle (xx, yy, zz), for the tangent point ($ML_{gtang}$, $DV_{gtang}$, $AP_{gtang}$), and for the distance between them ($SQRT((xx-ML_{gtang})^2+(yy-DV_{gtang})^2+(zz-AP_{gtang})^2)$) renders the equations to:

$$AlphaDirecCos_{RADIUS}=(xx-ML_{gtang})/SQRT((xx-ML_{gtang})^2+(yy-DV_{gtang})^2+(zz-AP_{gtang})^2) \quad (4)$$

$$BetaDirecCos_{RADIUS}=(yy-DV_{gtang})/SQRT((xx-ML_{gtang})^2+(yy-DV_{gtang})^2+(zz-AP_{gtang})^2) \quad (5)$$

$$\text{GammaDirecCOS}_{RADIUS}=(zz-AP_{gtang})/\text{SQRT}((xx-ML_{gtang})^2+(yy-DV_{gtang})^2+(zz-AP_{gtang})^2) \quad (6)$$

The tangent lies in a plane normal to this radius. The general formula for a plane passing through a given point $(x_0, y_0, z_0)$ and perpendicular to a given line (direction cosines A, B, C) is (Protter et al., supra, p. 545; and Love, supra, p. 136):

$$A*(X-x_0)+B*(Y-y_0)+C*(Z-z_0)=0 \quad (7)$$

Substituting in Equation (7) the point ($ML_{gtang}$, $DV_{gtang}$, $AP_{gtang}$) and the direction cosines of the radius given in Equations (4), (5), and (6) provides an equation for the plane normal to the radius:

$$[(xx-ML_{gtang})/\text{SQRT}((xx-ML_{gtang})^2+(yy-DV_{gtang})^2+ \quad (8)$$

$$(zz-AP_{gtang})^2)]*(X-ML_{Gtang})+[(yy-DV_{gtang})/\text{SQRT}((xx-$$

$$ML_{gtang})^2+(yy-DV_{gtang})^2+(zz-AP_{gtang})^2)]*(Y-DV_{gtang})+$$

$$[(zz-AP_{gtang})/\text{SQRT}((xx-ML_{gtang})^2+(yy-DV_{gtang})^2+$$

$$(zz-AP_{gtang})^2)]*(Z-AP_{gtang})=0$$

Now, the tangent line lies not only in the plane normal to the radius (Equation (8)), but also, by definition, in the circle plane:

$$AA*X+BB*Y+CC*Z+DD=0 \quad (9)$$

All solutions to the two Equations (8) and (9) have the proportions of the determinants implicit in the equations (Taylor, supra, pp. 522, 546, 554). For illustration, the equations and the determinants can be restated in more general form:

$$A*X+B*Y+C*Z+D=0 \quad (10)$$

$$A'*X+B'*Y+C'*Z+D'=0 \quad (11)$$

The proportional determinants implied by the pair of equations are:

$$\begin{vmatrix} B & C \\ B' & C' \end{vmatrix} \begin{vmatrix} C & A \\ C' & A' \end{vmatrix} \begin{vmatrix} A & B \\ A' & B' \end{vmatrix} \quad (12)$$

The same values can be expressed algebraically according to the standard definition of a 2×2 determinant:

$$(B*C'-B'*C):(C*A'-C'*A):(A*B'-A'*B) \quad (13)$$

These are the proportions of the direction cosines of the intersection line that is contained in both planes (10) and (11). By substitution in (13) of the values of the coefficients of the plane of the tangent (normal to the radius to the tangent point) (Equation 8) and the plane of the circle (Equation 9), and rearrangement, formulas for the direction cosines of the tangent can be expressed as three fractions, each of which has the same denominator:

$$den=\text{SQRT}(P+Q+R)$$

where $$P=(((DV_{gtang}-yy))*CC-((AP_{gtang}-zz))*BB)^2$$

$$Q=(((AP_{gtang}-zz))*AA-((ML_{gtang}-xx))*CC)^2$$

$$R=(((ML_{gtang}-xx))*BB-((DV_{gtang}-yy))*AA)^2$$

$$\text{AlphaDirecCos}_{gtang}=((DV_{gtang}-yy)*CC-(AP_{gtang}-zz)*BB)/den \quad (14)$$

$$\text{BetaDirecCos}_{gtang}=((AP_{gtang}-zz)*AA-(ML_{gtang}-xx)*CC)/den \quad (15)$$

$$\text{GammaDirecCos}_{gtang}=((ML_{gtang}-xx)*BB-(DV_{gtang}-yy)*AA)/den \quad (16)$$

The actual value of the square root in the denominator can be either positive or negative. AA, BB, CC, and DD (as defined earlier) represent the direction cosines for the circle-plane—i.e., for the vector normal to the plane. The direction of this vector depends in part on the ordering of the coronal planes ($Z=AP_A$, $Z=AP_B$, $Z=AP_C$) containing the three original target points. When these planes proceed from posterior to anterior—from smaller to larger AP—the normal is directed to the "subject's right" half of the coordinate space (octants II, III, VI, VII); when the ordering is from anterior to posterior—from larger to smaller AP—the normal is directed to the "subject's left" half of the coordinate space (octants I, IV, V, VIII). The direction does not affect the calculation of the circle's intersection points with coronal planes, based on AA, BB, CC, and DD (see above), but it does affect the direction cosines of the guide-tube cannula and the wire, which in turn affect the orientation of the guide-tube cannula. A change in the sign of "den", changing the sign of the direction cosines, reverses the direction of the cannula. When the order of $AP_A$, $AP_B$, $AP_C$ proceeds from anterior to posterior ($AP_A>AP_C$), a positive den directs the guide-tube cannula from its own top to its own tip, so that if the tangent point is posterior to the lowest point on the circle, then DVtop is positive and DVtop–DVtip as calculated below (Part V Step 2 Equation (8)) is positive; when the order of $AP_A$, $AP_B$, $AP_C$ proceeds from posterior to anterior ($AP_C>AP_A$), a negative den has the same effect. Therefore, in order to permit the ordered input of points $AP_A$, $AP_B$, and $AP_C$ in sequence either from anterior to posterior or from posterior to anterior, $\text{SIGN}(AP_A-AP_C)$ is factored into den. This has the effect of directing the guide-tube from its own top to its own tip in all cases. If the tangent point is posterior to the lowest point on the circle, then DVtop is above DVtip and DVtop–DVtip is positive; if the tangent point is anterior to the lowest point on the circle, then DVtop is below DVtip and DVtop–DVtip is negative. The complete formula for the denominator is therefore:

$$den=(\text{SIGN}(AP_A-AP_C))*\text{SQRT}(((DV_{gtang}-yy))*CC-((AP_{gtang}-zz))*BB)^2+(((AP_{gtang}-zz))*AA-((ML_{gtang}-xx))*CC)^2+(((ML_{gtang}-xx))*BB-((DV_{gtang}-yy))*AA)^2) \quad (17)$$

An entirely analogous derivation leads to the direction cosines of the wire tangent $\text{AlphaDirecCos}_{wtang}$, $\text{BetaDirecCos}_{wtang}$, and $\text{GammaDirecCos}_{wtang}$.

3. A third step is to use the direction cosines to determine the points at which the guide-tube cannula and the wire intersect each plane (in the series of planes parallel to the arbitrarily selected plane). Again, there are a number of ways to do this. One useful way is illustrated below.

Designate the coordinates of the point of intersection of the tangent with the parallel plane as $ML_{legtraj}$ (the X-coordinate), $DV_{legtraj}$ (the Y-coordinate), and $AP_{legtraj}$ (the Z-coordinate, which is the Z-coordinate of the entire parallel XY plane (coronal plane) in this example).

Now the direction cosines of a line, as stated above, are related to the coordinates of any two points $(x_1, y_1, z_1)$ and $(x_2, y_2, z_2)$ through which the line passes, and the distance d between the two points (Protter et al., supra, p. 538, and Love, supra, p. 129):

$$\text{AlphaDirecCos}=(x_2-x_1)/d \quad (1)$$

$$\text{BetaDirecCos}=(y_2-y_1)/d \quad (2)$$

$$\text{GammaDirecCos} = (z_2 - z_1)/d \qquad (3)$$

It is evident, from dividing (1) by (3), that $$\text{AlphaDirecCos/GammaDirecCos} = (x_2 - x_1)/(z_2 - z_1) \qquad (4)$$

The line passes through the tangent point ($ML_{gtang}$, $DV_{gtang}$, $AP_{gtang}$) and through the point in the parallel plane ($ML_{legtraj}$, $DV_{legtraj}$, $AP_{legtraj}$), of which $AP_{legtraj}$ (the Z-coordinate) is known. Therefore, by substitution of these points for the two points ($x_1$, $y_1$, $z_1$) and ($x_2$, $y_2$, $x_2$) in (4), it is clear that:

$$\text{AlphaDirecCos}_{gtang}/\text{GammaDirecCos}_{gtang} = (ML_{legtraj} - ML_{gtang})/(AP_{legtraj} - AP_{gtang}) \qquad (5)$$

and by rearrangement, $$ML_{legtraj} = ML_{tang} + (\text{AlphaDirecCos}_{gtang}/\text{GammaDirecCos}_{gtang}) * (AP_{legtraj} - AP_{gtang}) \qquad (6)$$

In similar fashion, it is clear from this that:

$$DV_{legtraj} = DV_{tang} + (\text{BetaDirecCos}_{gtang}/\text{GammaDirecCos}_{gtang}) * (AP_{legtraj} - AP_{gtang}) \qquad (7)$$

The guide-tube cannula tangent coordinates ($ML_{gtang}$, $DV_{gtang}$, $AP_{gtang}$) can of course be replaced by the analogous wire tangent coordinates ($ML_{wtang}$, $DV_{wtang}$, $AP_{wtang}$), in which case the resulting intersection coordinates ($ML_{legtraj}$, $DV_{legtraj}$, $AP_{legtraj}$) describe the wire tangent trajectory.

4. A fourth step is to construct a series of X, Y, and Z values copied from the results of Part II Steps 4–6 and Part III Step 3, which provide the points on the curved and straight parts of the trajectory, respectively. On the basis of the two tangent points selected in Part III Step 1, this series contains the coordinates of the guide-tube cannula intersections with the parallel planes up to the point of tangency, then the coordinates of the circle intersections up to the second point of tangency, then the coordinates of the wire intersections for the remainder of the parallel planes. This series represents the required trajectory. QED.

IV. Machine-dependent output Algorithms

From a series of trajectory points to a visual display.

1. A first step is to convert the final output trajectory (Core Algorithms) into pixel positions in a TIF file to be displayed by an imaging system. There are various ways to accomplish this conversion. One reasonable example is given below.

The AP coordinates for a trajectory point, ($AP_{arctraj}$) or ($AP_{legtraj}$), provide the equivalents in TIF coordinates ($AP_{arctrajPIX}$) or ($AP_{legtrajPIX}$) directly from Part I Step 5 Equation (11).

$$AP_B = \text{SliceThickness} * (Pt2AP - EBZeroAP) \qquad (1)$$

Substituting $AP_{arctraj}$ for $AP_B$ and $AP_{arctrajPIX}$ for Pt2AP gives:

$$AP_{arctraj} = \text{SliceThickness} * (AP_{arctrajPIX} - EBZeroAP) \qquad (2)$$

and rearranging provides:

$$AP_{arctrajPIX} = EBZeroAP + AP_{arctraj}/\text{SliceThickness} \qquad (3)$$

The ML and DV coordinates for a trajectory point ($ML_{arctraj}$ and $DV_{arctraj}$, or, $ML_{legtraj}$ and $DV_{legtraj}$), in terms of the orthogonal coordinate system used by the Core Algorithms, can be scaled and converted to pixels in the TIF coordinate system. Equations (17) and (18) from Part I Step 5 are already available for relating MRI ML and DV values in pixels (such as Pt2ML and Pt2DV) to Core Algorithm values in millimeters (such as $ML_B$ and $DV_B$):

$$ML_B = \text{PixelSize} * (\text{MidP2Slope} * Pt2ML - Pt2DV + \text{MidP2Intercept})/\text{SQRT}(\text{MidP2Slope}^2 + 1) \qquad (4)$$

$$DV_B = \text{PixelSize} * (\text{EarbarSlope} * Pt2ML - Pt2DV + \text{EarbarIntercept})/\text{SQRT}(\text{EarbarSlope}^2 + 1) \qquad (5)$$

The corresponding equations for trajectory points on the circle can be written by substituting the known values $ML_{arctraj}$ and $DV_{arctraj}$ (Part III Step 4, in millimeters) for $ML_B$ and $DV_B$ respectively in (1) and (2), and the unknown values $ML_{arctrajPIX}$ and $DV_{arctrajPIX}$ for Pt2ML and Pt2DV:

$$ML_{arctraj} = \text{PixelSize} * (\text{MidP2Slope} * ML_{arctrajPIX} - DV_{arctrajPIX} + \text{MidP2Intercept})/\text{SQRT}(\text{MidP2Slope}^2 + 1) \qquad (6)$$

$$DV_{arctraj} = \text{PixelSize} * (\text{EarbarSlope} * ML_{arctrajPIX} - DV_{arctrajPIX} + \text{EarbarIntercept})/\text{SQRT}(\text{EarbarSlope}^2 + 1) \qquad (7)$$

The only unknowns in these two equations are $ML_{arctrajPIX}$ and $DV_{arctrajPIX}$, the points in MRI pixel terms that are needed. Solving the two equations for the two unknowns provides the formulas:

$$(8)$$
$$ML_{arctrajPIX} =$$
$$[\, (DV_{arctraj} / \text{PixelSize}) * \text{SQRT}(\text{EarbarSlope}^2 + 1)$$
$$- (ML_{arctraj} / \text{PixelSize}) * \text{SQRT}(\text{MidP2Slope}^2 + 1)$$
$$+ \text{MidP2Intercept}$$
$$- \text{EarbarIntercept} \,]$$
$$/ [\, \text{EarbarSlope} - \text{MidP2Slope} \,]$$

$$(9)$$
$$DV_{arctrajPIX} =$$
$$[\, (DV_{arctraj} / \text{PixelSize}) * \text{MidP2Slope} * \text{SQRT}(\text{EarbarSlope}^2 + 1)$$
$$- (ML_{arctraj} / \text{PixelSize}) * \text{EarbarSlope} * \text{SQRT}(\text{MidP2Slope}^2 + 1)$$
$$+ \text{EarbarSlope} * \text{MidP2Intercept} - \text{MidP2Slope} * \text{EarbarIntercept} \,]$$
$$/ [\, \text{EarbarSlope} - \text{MidP2Slope} \,]$$

The same derivation provides the analogous display-ready leg-points ($ML_{legtraj}$, $DV_{legtraj}$, $AP_{legtraj}$).

2. A second step is to perform operations similar to those of Part I Step 2, configuring equipment that can be used to interface between the analytic algorithms that plan the trajectory and the display from the imaging scanner. Again, there are a number of ways to do this. One useful way is illustrated below.

As explained above (Part I Step 2 Procedures (1) to (3)), the TIF file as converted for video display is a series of numbers (of magnitude between 0 and 254) representing gray-scale values of pixels in an orderly array. For displaying point ($ML_{arctrajPIX}$, $DV_{arctrajPIX}$, $AP_{arctrajPIX}$), Procedures (5) and (4) of Part I Step 2 are reversed:

(1) The analytic algorithms pass this converted trajectory point to a text file, which is then taken up by another 80486 program (in Microsoft Visual BASIC) that surveys the original TIF file from the MRI and highlights the pixel representing the trajectory point in the appropriate section ($AP_{arctrajPIX}$) This program uses the TIF file's row and column arrangement and its header length to determine which pixel position to highlight. Altogether there are (HeaderLength+256*256) pixels. Actually pixels in a 3×3 square grid are highlighted (set to 255) for each point. A slightly different shape is used for the trajectory points nearest the original target points, and other shapes are used for the points at the beginning and end of the "target structure" and for the entry and exit points on the cranium (see Part VII Step 6 below).

(2) The file is then displayed by a commercial image-display package (Adobe Photoshop), for visual observation.

The highlighted pixels appear distinctly, at the predicted anatomical position of the point.

3. EPROM: A third step is to evaluate the trajectory resulting from the entry of the three original target points and two tangent points. If visual inspection of the display shows that the anatomical placement could be improved, changes can be made. The numerical value of an original target point or points can be modified. The algorithms repeat the analysis and display a modified trajectory. A sophisticated system (Steps 3b and 3c below) may be implemented utilizing procedures and software stored on a permanent memory device, such as an erasable programmable read only memory (EPROM) chip programmed to make these modifications by a variety of GUI input options and to keep all other algorithmic computations updated accordingly.

a. Real Input Mode

An elementary way to modify the input is simply to switch to "Real Input" mode (see Part I, Step 6), enter modified target points, and allow the algorithms to repeat the analysis. The specific "fine adjustments" introduced above (Part I Step 8) may also be made at this point.

b. Cross-section manipulation

Another way will be to incorporate image display algorithms into an EPROM device to permit rapid processing of GUI input and output. Both the underlying calculations and the image displayed on the basis of the calculations will be rapidly updated in response to keyboard or GUI inputs. The EPROM will display a series of separated parallel cross-sections that can be manipulated in perspective. The cross-sections can be viewed from an angle, with the dorsal edge up and the ventral edge down (for brain sections) and with the anterior surface appearing in perspective. Each trajectory point appears in position in its section. By option, the display can be adjusted, and the cross-sections can be manipulated in several ways by moving a cursor, e.g., with a mouse:

(1) the cross-sections can be variably rotated, each on its own mid-sagittal axis, like slats of a blind;

(2) the screen distance between cross-sections in the display can be changed;

(3) cross-sections can be added to or removed from the display;

(4) a common portion of each cross-section can be erased from the display for better visibility;

(5) the row of cross-sections can be divided at any point leaving a single larger between-section interval between two groups of cross-sections;

(6) a given cross-section can be removed from the row and examined full-front;

(7) that cross-section or all the cross-sections can be magnified or diminished;

(8) alternatively, the screen can be split between a smaller area for a reduced rendition of the series of cross-sections, emphasizing the trajectory points, and a large area showing selected cross-sections full-front.

c. Trajectory manipulation

The display of trajectory points can be separately manipulated. Its portrayal on the screen can be shifted from single points on individual sections to a continuous line of points for manipulation as a unit under optional constraints. The basic pattern of interaction is simple. The user "clicks and drags" a single point on the line from one position to another, the line remodels itself in response, and all displays and algorithms are updated. A given version can be saved at any point, to be recalled later on. Some of the constraints are:

(1) the entire trajectory moves as a single object, without changing its curvature or its angles of orientation;

(2) the line is fixed at two selected (clicked) points and when a third point is dragged it rotates the trajectory around these points as an axis;

(3) either the guide-tube cannula tangent or the wire tangent is selected as an axis, and when a point is dragged the trajectory rotates on that axis, without otherwise changing;

(4) each tangent is fixed at one selected point, and when a point on the trajectory is dragged the curvature of the arc is increased or decreased, and tangents are realigned to remain tangential, while the angles of orientation of the circle plane remain the same;

(5) the angles (direction cosines) of the tangents are fixed, and when a point on the arc is dragged the curvature of the arc is increased or decreased, and tangents are translated to remain tangential, while the angles of orientation of the circle plane remain the same;

(6) the point selected is substituted for the nearest original target point or tangent point, and the trajectory is adjusted in response, without altering the other four entry points.

A digital display of critical features of the trajectory will also be available, and changes made on this display from the keyboard will be reflected in the display of the trajectory. These features will include the coordinates of the original target points and tangent points, the center and radius of the circle and the angles of orientation of its plane (or the various features of the helix listed in Part IX, Step 15), the angles of orientation of the tangent lines, the coordinates of the points at which the trajectory enters or exits the body, and the coordinates of the points at which the trajectory enters or exits the target structure.

Input options will also include the helical trajectory, and the complex trajectories consisting of alternating straight and curved portions (see FIG. 2A–2E). More than three target points can be entered for fitting to these trajectories. The user will be required to specify the number of full periods to be included, for a helical trajectory, and the locations of break-points between one curvature and another for a complex trajectory. Options comparable to those listed above will be included for these trajectories in the EPROM. The arcuate trajectory will still be available by option, and the user will be able to shift back and forth among the best-fitting arcuate, helical, and complex trajectories for the full set of target points entered.

V. Machine-dependent output Algorithms

From the planned position of the guide-tube cannula to prescribed stereotactic angular settings.

1. The first step is to calculate lengths associated with the curvature concealed in the tip of the guide-tube cannula 20 and the straight wire segment 24 concealed in the tip of the curved nitinol tubing 28. There are a number of ways to do this. The example below describes one technique, referring to FIG. 5, where a partial cut-away view of the tool of FIG. 1 is shown.

The length of the guide-tube cannula 20 in which resides the initial curvature of the curved nitinol tubing 28 can be calculated by considering that this curvature is restrained by the inner edge of the cannula 20 at the cannula tip (point P). It is assumed that the curved nitinol tubing 28 is straight within the lower part of the cannula, held against its wall, just above a point at a level N near the tip, at which point it curves down and across the dead space in the cannula, from the far wall (far from the center of the circle) to the near wall (near the center of the circle). It emerges pressed against the near wall at the tip (point P).

The line from the center (point C) of the circle to a point E on the cannula directly across the cannula from point N is assumed to be perpendicular, since the tubing is assumed to express its curvature as far up the cannula as possible. The length of such a perpendicular to the inner edge of the curved tubing (point N) is simply the radius (rad) of the circle. (At this point the precise definition of the radius as the distance from the center to the inner aspect of the curved tubing becomes geometrically important and desirable from a practical point of view, in that it is easily measured and related in the simplest way to the fabrication of the curved tubing by wrapping it around a mandrill.) Its length to E is rad, less the deadspace (the difference between the inner diameter of the cannula and the outer diameter of the curved tubing). The distance from the center of the circle to the curved tubing at its point of emergence P, where it is pressed against the inner wall of cannula, is rad.

In $\Delta$CEP, the leg of the triangle EP, along the inner edge of the cannula, is the length (CurveInGuideLength) of the terminal portion of the cannula within which the initial curvature of the circle is contained. It can be calculated from the Pythagorean theorem ($CE^2+EP^2=PC^2$) that:

$$(rad-(ID-OD))^2 + CurveInGuideLength^2 = rad^2 \qquad (1)$$

or, $$CurveInGuideLength = SQRT(rad^2-(rad-(ID-OD))^2) \qquad (2)$$

On the same triangle, the angle ECP that subtends the arc concealed in the cannula can be calculated as:

$$\arcsin(CurveInGuideLength/rad) \qquad (3)$$

and therefore the linear length along this arc must be:

$$CurveInGuideArcLength = rad*\arcsin(CurveInGuideLength/rad) \qquad (4)$$

At the tip of the curved nitinol tubing, the forced curvature of the natively straight nitinol wire 24 will end at a point T on the inner wall of the tubing slightly before its tip. In the final arc ("omega") of the tubing, the wire is straight, traversing the tubing deadspace. At the tip of the tubing, the radius from the center of the circle (C) to its inner wall (H) does not quite reach the edge of the wire. It has to be extended across deadspace. But this deadspace is not simply the difference between the diameters, because the wire crosses the lumen at the tip of the tubing at an angle. By similar triangles ($\Delta$TCX and $\Delta$XFR), however, it can be seen that the angle XFR is also omega. Therefore:

$$FX = RF/\cos(omega) = ODNitWire/\cos(omega) \qquad (5)$$

Since HF=IDNitTube, the length HX can now be written:

$$HX = IDNitTube - (ODNitwire/\cos(omega)) \qquad (6)$$

and CX, the hypotenuse of $\Delta$TCX, is (rad+HX), or:

$$rad + IDNitTube - (ODNitWire/\cos(omega)) \qquad (7)$$

The cosine of the angle omega in $\Delta$TCX can now be set equal to CT/CX, leading to:

$$\cos(omega) = rad/(rad+IDNitTube-(ODNitWire/\cos(omega))) \qquad (8)$$

Solving (8) for cos(omega) yields:

$$\cos(omega) = (rad+ODNitWire)/(rad+IDNitTube) \qquad (9)$$

Therefore omega can be identified:

$$omega = \arccos((rad+ODNitWire)/(rad+IDNitTube)) \qquad (10)$$

and the linear length of the arc subtended by omega, the length, that is, of the tubing that conceals straight wire, is:

$$StraightWireArcLength = rad*\arccos((rad+ODNitWire)/(rad+IDNitTube)) \qquad (11)$$

The length (SF) of the straight wire "concealed" in the tubing (although $\Delta$XFR is beyond the tip) is also easily calculated from omega, since:

$$\tan(omega) = SF/CS \qquad (12)$$

or, substituting and rearranging, $$SF = (rad+ODNitwire)*\tan(omega) \qquad (13)$$

and, substituting the original values:

$$StraightWireLength = (rad+ODNitWire)*\tan(\arccos((rad+ODNitWire)/(rad+IDNitTube))) \qquad (14)$$

The length (GTUpper) of the guide-tube cannula 20 down to the beginning of the curvature of the nitinol tubing is a significant value, because it represents the total length of the guide-tube cannula line to its tangent point, and is used in certain calculations below:

$$GTUpper = LE - CurveInGuideLength \qquad (15)$$

2. A second step is to calculate the locations of the top and the tip of the guide-tube cannula 20 when it is in its final position. Again, there are a number of ways to do this. One useful way is illustrated below.

As stated above (Part III Step 2, Equations (1–3)), the general formulas for the direction cosines of a line between two points ($x_2$, $y_2$, $z_2$) and ($x_1$, $y_1$, $z_1$) at a distance d are:

$$AlphaDirecCos = (x_2-x_1)/d \qquad (1)$$

$$BetaDirecCos = (y_2-y_1)/d \qquad (2)$$

$$GammaDirecCos = (z_2-z_1)/d \qquad (3)$$

(Love, supra, p. 129, and Protter et al., supra, p. 538)

The point of tangency for the guide-tube cannula ($ML_{gtang}$, $DV_{gtang}$, $AP_{gtang}$) is known and can be substituted for one point, and the coordinates for the top of the guide-tube cannula (MLtop, DVtop, APtop) can be substituted for the other point in these formulas. The distance d, furthermore, from the top of the guide-tube to the point of tangency (at which curvature begins), is now known as (GTUpper=LE−CurveInGuideLength), derived above.

$$AlphaDirecCos_{gtang} = (ML_{gtang}-MLtop)/GTUpper \qquad (4)$$

$$BetaDirecCos_{gtang} = (DV_{gtang}-DVtop)/GTUpper \qquad (5)$$

$$GammaDirecCos_{gtang} = (AP_{gtang}-APtop)/GTUpper \qquad (6)$$

From these formulas, by rearrangement, it immediately follows that:

$$MLtop = ML_{gtang} - GTUpper*AlphaDirecCos_{gtang} \qquad (7)$$

$$DVtop = DV_{gtang} - GTUpper*BetaDirecCos_{gtang} \qquad (8)$$

$$APtop = AP_{gtang} - GTUpper*GammaDirecCos_{gtang} \qquad (9)$$

In like manner, the coordinates for the tip of the guide-tube cannula (MLtip, DVtip, APtip) can be substituted in formulas (1–3), along with the coordinates of the point of tangency and its distance from the tip (CurveInGuideLength), to provide the coordinates of the tip of the guide-tube cannula:

$$MLtip=ML_{trans}-CurveInGuideLength*AlphaDirecCos_{trans} \quad (10)$$

$$DVtip=DV_{trans}-CurveInGuideLength*BetaDirecCos_{trans} \quad (11)$$

$$APtip=AP_{trans}-CurveInGuideLength*GammaDirecCos_{trans} \quad (12)$$

3. A third step is to generate the angles at which to set the stereotactic apparatus. There are a number of ways to do this, depending in part on the type of stereotactic apparatus to be employed in surgery. The example below describes one technique adapted to the Kopf stereotactic apparatus. All angles have been left in radians, although in the software itself they must be converted into degrees to conform with the units used in typical stereotactic scales.

One specific implementation of an implantation tool 10 according to the present invention is shown in FIG. 4, where a Kopf stereotactic device 100 is shown with a cranium 150 mounted thereon. Briefly, the device 100 is used to position the tool 10 by holding the cranium 150 in a fixed position and by moving the guide-tube cannula relative to the cranium 150 through one of several calibrated adjustments. The device 100 includes horizontal and vertical slides 195, 120 and two adjustment scales 160, 170. The scales are known as the PED scale 160 and the ROT scale 170. The cranium 150 is fixed through use of an earbar 180 and eyebars 140. The implantation tool 10 is fixed to the device 100 by inserting the guide-tube cannula 20 into a block 15 mounted on a rod held by the horizontal slide 195. Calibration of the device 100 for use with the tool 10 of the present invention will now be described.

The Kopf stereotactic apparatus provides for two calibrated rotational adjustments. The PED scale 160 is located at the joint between the cannula-carrier and the lateral arm 110 of the apparatus on which it slides, and permits a rotation of the carrier around the DV axis by a measured angular distance (PED) away from the sagittal plane (YZ plane). The physical axis of rotation for this adjustment is offset from the shaft of the guide-tube cannula 20 itself, in the Kopf stereotactic, but this offset can be compensated by a translational adjustment later on. In effect, adjustment at this joint rotates what will be called the "cannula-carrier plane" away from its initial orientation parallel to the sagittal plane (YZ plane) of the cranium 150, to a new orientation, parallel to the plane containing the guide-tube cannula 20 in its planned final position and the projection of the guide-tube cannula onto the axial plane. This new position is specified by the direction cosines of the guide-tube cannula, which imply a projection onto the axial plane (XZ plane) at an angle PED from the Z axis.

Figure 6A:
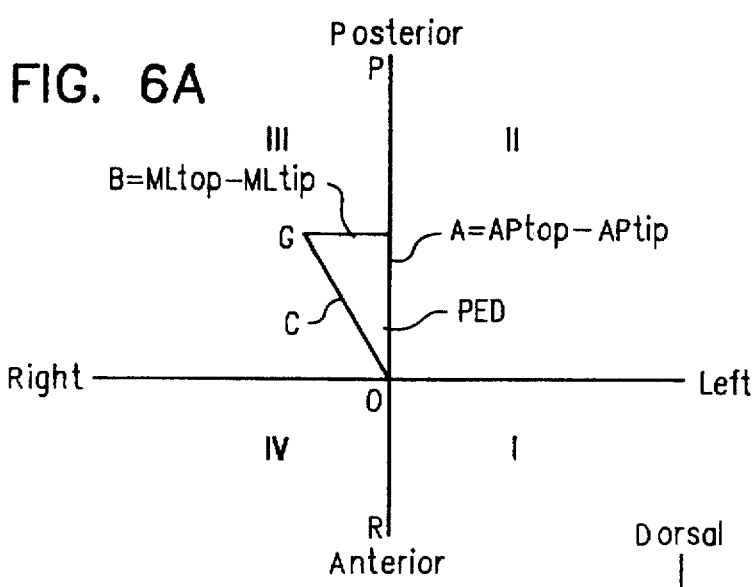
FIG. 6A–B illustrate geometrically the PED (6A) and ROT (6B) adjustments for a device of the present invention, as mounted on a Kopf stereotactic instrument (Description of Specific Embodiment, Part V, Step 3).

The angle PED can be calculated from the known points at the top and the tip of the guide-tube cannula by considering this projection (FIG. 6A). It is a transverse line in the axial plane that constitutes the hypotenuse of a triangle of which the height (parallel to the AP axis) is:

$$A=APtop-APtip \quad (1)$$

and the base (parallel to the ML axis) is:

$$B=MLtop-MLtip \quad (2)$$

The length of the hypotenuse is therefore:

$$C=SQRT((APtop-APtip)^2+(MLtop-MLtip)^2) \quad (3)$$

The angle of the hypotenuse from the AP axis is therefore:

$$PED_{unadjusted}=arccos((APtop-APtip)/SQRT((APtop-APtip)^2+(MLtop-MLtip)^2)) \quad (4)$$

This formula for the angle PED needs to be adjusted, however, to accommodate the ambiguity of the arccos function and the peculiarities of the stereotactic equipment. For each cosine value (from 1 to −1) the spreadsheet arccos function chooses the corresponding arccos value between 0 and $\pi$ although there is also a distinctive angle between $\pi$ and $2\pi$ which should be chosen in some cases. FIG. 6A with labeled vertices illustrates this point, portraying the projection of the guide-tube cannula 20 onto the XZ plane, translated to bring its tip to the origin for convenient analysis. The angle $PED_{unadjusted}$ specified by Equation (4) is the angle ROG, measured from the positive AP axis to the projection of the guide-tube cannula. The arccos function returns only the arccos value between 0 and $\pi$, even though in the case illustrated the angle ROG would be properly designated by the corresponding angle between $\pi$ and $2\pi$, rotating through quadrants I (+AP, +ML) and II (−AP, +ML) and into Quadrant III (−AP, −ML). One must account for the full 360° range of possible angles, counting in order from the "Anterior" axis through quadrants I, II, III, and IV. As the cosines go from 1 to −1 through quadrants I and II—i.e., (MLtop−MLtip)>0—the angles provided by the spreadsheet go from 0° to 180°. As the cosines continue from −1 to 1 through quadrants III and IV, however—i.e., (MLtop−MLtip)<0—the angles provided by the spreadsheet do not continue from 180° to 360° as desired, but go from 180° back down to 0°. This second series must be corrected by taking $360-PED_{unadjusted}$ instead of $PED_{unadjusted}$.

The angle $PED_{unadjusted}$ of Equation (4) also needs to be adjusted to accommodate peculiarities of the stereotactic equipment. The Kopf stereotactic scale for PED has a conveniently readable excursion of only ±50°. In keeping with the convention that anterior is positive, it is consistent to express the adjustment as a positive angle when it shifts the movable line on this scale toward the anterior, and as a negative angle when it shifts the movable line toward the posterior. This has to be true regardless of whether the carrier is placed on the left arm (SideArm=1) or the right arm (SideArm=−1).

An analysis of the possible cases is necessary to generate the appropriate adjustment for a PED angle that rotates the cannula-carrier plane into each quadrant of the ML/AP plane. In Table 1, on the next page, ORI represents the original unadjusted angle $PED_{unadjusted}$ of Equation (4). Further simplification yields the final Table 2 on the subsequent page. (The variable names "APorient", "MLorient", and "SideArm" are introduced for SIGN (APtop−APtip), SIGN (MLtop−MLtip), and Carrier on the Right or Left, respectively. The "Total Adjustment" column is simplified, an example is introduced, and the row order is rearranged.) The eight combinations of sign conditions represented in these eight rows can be summarized in the formula that heads the right-hand column, because: (1) If APorient is negative, then 180 must be added or subtracted. (2) If SideArm*MLorient is negative, the final value is either (ORI) or (ORI−180).

TABLE 1

| SIGN(APtop-APtip) | SIGN(MLtop-MLtip) | Quadrant | Arccos Adjustment | Total Adjustment | ROT |
|---|---|---|---|---|---|
| Carrier on the Right: | | | | | |
| 1 | 1 | I | ORI | ORI | negative |
| -1 | 1 | II | ORI | ORI-180 | positive |
| -1 | -1 | III | 360-ORI | (360-ORI)-180 | positive |
| 1 | -1 | IV | 360-ORI | (360-ORI)-360 | negative |
| Carrier on the Left: | | | | | |
| 1 | 1 | I | ORI | -ORI | negative |
| -1 | 1 | II | ORI | 180-ORI | positive |
| -1 | -1 | III | 360-ORI | 180-(360-ORI) | positive |
| 1 | -1 | IV | 360-ORI | 360-(360-ORI) | negative |

TABLE 2

| APorient | MLorient | SideArm | Quadrant | Adjustment to stereo | ROT | SampleORI | (-SideArm * MLorient) * (ORI-(180 * (-APorient))) |
|---|---|---|---|---|---|---|---|
| 1 | -1 | 1 | IV | ORI | negative | 30 | 30 |
| 1 | 1 | -1 | I | ORI | negative | 30 | 30 |
| 1 | -1 | -1 | IV | -ORI | negative | 30 | -30 |
| 1 | 1 | 1 | I | -ORI | negative | 30 | -30 |
| -1 | 1 | -1 | II | ORI-180 | positive | 30 | -150 |
| -1 | -1 | 1 | III | ORI-180 | positive | 30 | -150 |
| -1 | -1 | -1 | III | 180-ORI | positive | 30 | 150 |
| -1 | 1 | 1 | II | 180-ORI | positive | 30 | 150 |

The appropriately adjusted formula is therefore:

$$PED = (-SideArm * MLorient) * ([PED_{unadjusted}] - (180 * (-APorient))) \quad (5)$$

or, $$PED = (-SideArm * MLorient) * ([arccos((APtop-APtip)/SQRT((APtop-APtip)^2+(MLtop-MLtip)^2))] - (180 * (-APorient))) \quad (6)$$

Note that the set of cases in the table above assumes always an approach in which DVtop>DVtip. The alternative, an approach from below, is not permitted by the Kopf stereotactic equipment.

The Kopf stereotactic apparatus also provides for a second calibrated rotational adjustment ("ROT scale") 170, permitting rotation of the guide-tube 20 within the originally parasagittal (but now adjusted) cannula-carrier plane. This scale, located between the PED scale 160 and the vertical slide 120 of the cannula-carrier, permits a rotation of the cannula-carrier plane around its adjusted X axis ("ML" axis) by a measured angular distance (ROT). (Note that once adjusted, the originally AP, ML, and DV axes will be designated in quotation marks in this narrative.) The physical axis of rotation for this adjustment is offset from the shaft of the guide-tube cannula itself in the Kopf stereotactic, but like the PED offset this offset can be compensated by a translational adjustment later on. In effect, adjustment at this joint rotates the cannula-carrier plane from its initial orientation, with its DV axis parallel to the sagittal plane of the cranium, to a new orientation, with its "DV" axis parallel to the guide-tube cannula. This new position is specified by the direction cosines of the guide-tube cannula, which imply a new orientation within the cannula-carrier plane at an angle ROT from the Y axis (DV axis).

Figure 6B:
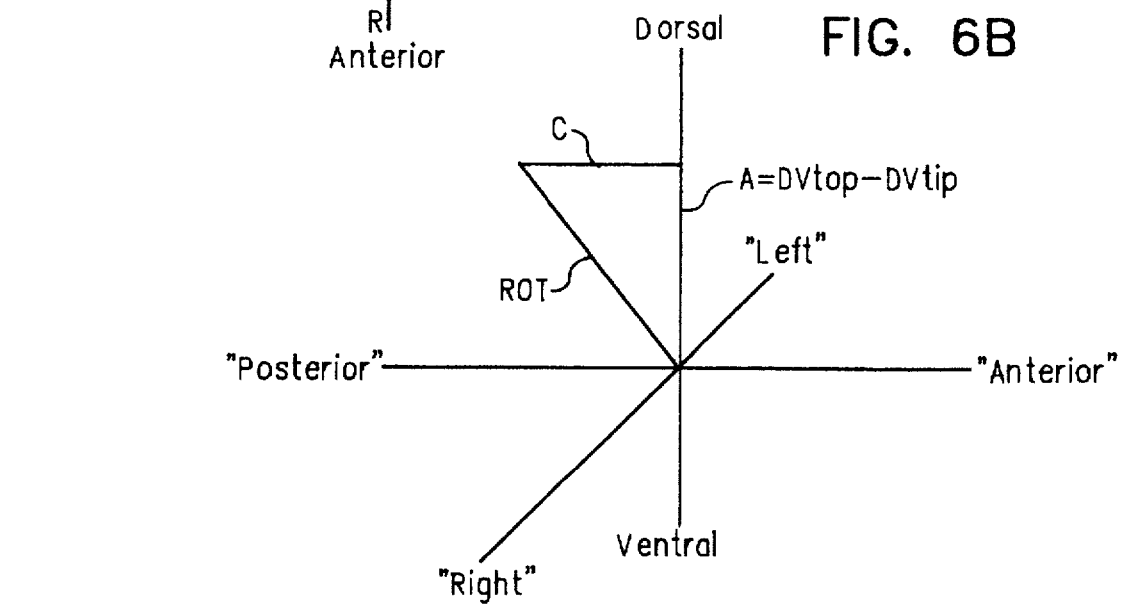

The angle ROT can be calculated from the known points at the top and the tip of the guide-tube cannula by considering this cannula-carrier plane (FIG. 6B). The cannula is a transverse line in the cannula-carrier plane that constitutes the hypotenuse of a triangle of which the height (parallel to the DV axis) is:

$$A = DVtop - DVtip \quad (7)$$

and the base (the transverse line across the axial plane (ML/AP plane or Z plane)), as calculated in (3) above is:

$$C = SQRT(APtop-APtip)^2 + (MLtop-MLtip)^2 \quad (8)$$

The angle of the hypotenuse from the DV axis is therefore:

$$ROT = (-APorient) * arctan((SQRT(APtop-APtip)^2+(MLtop-MLtip)^2)/(DVtop-DVtip)) \quad (9)$$

In Equation (9), the tangent (of which ROT is the arctan) can obviously lie between negative and positive infinity. For each tangent value the default arctan value is between $-\pi/2$ and $\pi/2$, although there is also a distinctive angle beyond this range. Note that if DVtop>DVtip, the tangent will always be positive, and the angle prescribed by Equation (9) will lie between 0 and $\pi/2$ (or between $-\pi/2$ and $-\pi$, but the default choice is the angle between 0 and $\pi/2$). As long as the guide-tube cannula 20 approaches a tangent point between the most posterior point and the most ventral point on the circle, APorient will be negative and the angle positive. Since the adjustment on the Kopf stereotactic moves the movable line anterior to the stationary line to set this angle, this sign is appropriate. If the approach is from the anterior direction, the guide-tube cannula will be tilted in the opposite manner, APorient will be positive, and the angle will appropriately be negative.

An approach in which DVtop<DVtip is not permitted by the Kopf stereotactic equipment, and cannot be appropriately accommodated by Equation (9).

4. A fourth step is to specify the "J–angle", the angle of rotation at which the arc of curved nitinol tubing will emerge.

The physical rotation of axes by the angles PED and ROT outlined in Part V Step 3 above brings the physical guide-tube cannula parallel to the position specified by its direction cosines, as provided by the Core Algorithms. The appropriate translational adjustments in three dimensions outlined in Part VI below will bring it into position as specified by the Core Algorithms. Although the cannula is now tangent to the circle planned by the Core Algorithms, it is also tangent to any other circle with a point of tangency at this point; an entire torus of tangent circles could be formed around the point of tangency, and the cannula would be tangent to any of them. Thus, as the curved nitinol tube emerges from the fully positioned guide-tube cannula, its plane of curvature can be oriented in any direction; but only one direction is correct. Therefore the algorithms must now specify that the curved nitinol tubing must be set at an angle of rotation (J) from the cannula-carrier plane. This is a convenient plane of reference for the J–angle, because when the PED and ROT angles are returned to 0, it is parallel to the sagittal plane.

The J–angle is calculated by considering that the plane of the circle must intersect the cannula-carrier plane, and that the guide-tube cannula must be included in both the plane of the circle and the cannula-carrier plane. As the curved portion is rotated (conceptually) from the cannula-carrier plane to the plane of the circle, its plane therefore moves through precisely the J–angle between those two planes.

In general, the angle $\theta$ between any two planes $$A_1*X + B_1*Y + C_1*Z + D_1 = 0 \quad (1)$$

and $$A_2*X + B_2*Y + C_2*Z + D_2 = 0 \quad (2)$$

is given by the formula $$\cos\theta = |A_1*A_2 + B_1*B_2 + C_1*C_2|/[(SQRT(A_1^2+B_1^2+C_1^2))*(SQRT(A_2^2+B_2^2+C_2^2))] \quad (3)$$

(Protter et al., supra, p. 549)
For the circle plane:

$$A_1 = AA = H/SQRT(H^2+I^2+J^2)$$
$$B_1 = BB = I/SQRT(H^2+I^2+J^2)$$
$$C_1 = CC = J/SQRT(H^2+I^2+J^2) \quad (4)$$

For the cannula-carrier plane, after the PED adjustment (with or without the ROT adjustment), all values of X and Z must satisfy the relationship:

$$(AlphaDirecCos/GammaDirecCos) = (X_2-X)/(Z_2-Z) \quad (5)$$

where $X_2$ and $Z_2$ are the ML and AP values of a point known to be on the cannula-carrier plane. Substituting the guide-tube cannula tangent point for $X_2$ and $Z_2$ in Equation (5), and rearranging to conform to the format of (2), the formula of the cannula-carrier plane is:

$$(1)*X+(0)*Y-(AlphaDirecCos/GammaDirecCos)*Z-(ML_{tang}-AP_{tang}*(AlphaDirecCos/GammaDirecCos))=0 \quad (6)$$

and $$A_2 = 1$$
$$B_2 = 0$$
$$C_2 = (-AlphaDirecCos/GammaDirecCos) \quad (7)$$

Substituting (4) and (7) in (3) provides:

$$\cos(J - \text{angle}) = |AA*(1) + BB*(0) + CC* \quad (8)$$
$$(-AlphaDirecCos/GammaDirecCos)|/[(SQRT(AA^2 + BB^2 + CC^2)) * (SQRT((1)^2 + (0)^2 + (-AlphaDirecCos/GammaDirecCos)^2))]$$

or, simplifying:

$$\cos(J-\text{angle}) = |AA-CC*(AlphaDirecCos/GammaDirecCos)|/[(SQRT(AA^2+BB^2+CC^2))*(SQRT(1+(AlphaDirecCos/GammaDirecCos)^2))] \quad (9)$$

To account for a full 360° range of possible J–angles, a sign must be provided for this expression. Counting in order from the Anterior axis through quadrants I (+Z, +X: Anterior Left) and II (–Z, +X: Posterior Left), the cosines go from 1 to –1, and the angles provided by the cosine function go from 0° to 180°. Continuing through quadrants III (–Z, –X: Posterior Right) and IV (+Z, –X: Anterior Right), the cosines return from –1 to 1, and the angles decrease from 180° back down to 0°. This second series is to be given a negative sign, indicating that the J–angle adjustment which rotates the guide-tube cannula moves the center of the circle to the right of the cannula-carrier plane.

If the center of the circle is to the right of the plane, then its ML will be less than the ML of a point on the plane at the same AP. To find such a point, the AP of the center of the circle (zz) is substituted for Z in the formula for the cannula-carrier plane (Equation (6) above), and the equation is rearranged and simplified to give:

$$X = ML_{tang} + (AlphaDirecCos/GammaDirecCos)*(zz-AP_{tang}) \quad (10)$$

If xx<X, then the arc should turn to the subject's right and it should have a negative sign; otherwise it should be positive. Therefore the J–angle is given by:

$$J = \text{SIGN}(xx - (ML_{tang} + \quad (11)$$
$$(AlphaDirecCos/GammaDirecCos) * (zz - AP_{tang}))) * \arccos\{|AA -$$
$$CC * (AlphaDirecCos/GammaDirecCos)|/[SQRT(AA^2 + BB^2 +$$
$$CC^2)) * (SQRT(1 + ((AlphaDirecCos/GammaDirecCos))^2))]\}$$

VI. Machine-dependent output Algorithms

From the planned position of the guide-tube cannula and the planned stereotactic angular settings to the translational adjustments necessary to bring the guide-tube cannula into the final position required by the Core Algorithms.

There are a number of ways to derive the necessary adjustments, depending in part on the type of stereotactic apparatus to be employed in surgery. The example below describes one technique adapted to the Kopf stereotactic apparatus which can be used for monkey or small-animal surgery. All angles have been left in radians, although in the software itself they must be converted into degrees to conform with the units used in typical stereotactic scales.

The Kopf stereotactic apparatus provides for three calibrated translational adjustments. One of these (AP) is at the base of the cannula-carrier, where it is clamped onto the stereotactic arm 110. The second (DV) is on the vertical slide 120, and the third (ML) is on the horizontal slide 195. Normal stereotactic practice involves "zeroing" the apparatus. This is necessary because the cannula can be attached to the cannula-carrier in a continuous range of different positions. It is therefore necessary in normal stereotactic practice to "find" the tip of the cannula by setting the translational adjustments to bring it to a known position, usually earbar zero.

In the following descriptions, "ML" and "DV" will be written in quotation marks when referring to the angled cannula, because after the PED and ROT angular adjustments have been made the "ML" and "DV" adjustments made on the originally vertical and horizontal slides are no longer truly ML and DV adjustments within the stereotactic coordinate system, which is still the frame of reference for the algorithms.

If the angles PED and ROT are small enough, the tip of the angled cannula can be zeroed as usual. (But see Part VIII Step 1 for the alternative case.) The settings on the "ML", "DV", and AP scales at earbar zero are designated MLZ, DVZ, and APZ, respectively. Even though the zero points are known, however, the proper "ML" and "DV" adjustments that need to be made to move from earbar zero to the prescribed implantation position cannot be calculated as straightforward additions or subtractions, as is the case for a non-angled cannula. The formulas for calculating the final settings are presented below.

Figure 7:
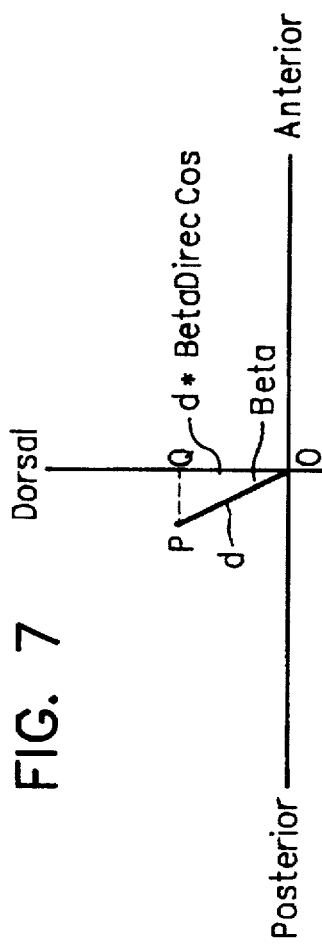
FIG. 7 illustrates geometrically the AX adjustment along the insertion axis for a device of the present invention, as mounted on a Kopf stereotactic instrument (Description of Specific Embodiment, Part VI, Step 1).

1. A first step is to make the insertion-axis adjustment. As shown in FIG. 7, which represents a projection of the guide-tube cannula 20 onto the sagittal plane (DV/AP plane; YZ plane), when PED=0, a "DV" adjustment of d millimeters on the vertical slide 120 of the stereotactic instrument moves the tip of the cannula along the insertion axis of the cannula from a position O ($x_1$, $y_1$, $z_1$) representing the origin, to a position P ($x_2$, $y_2$, $z_2$) representing the target point. For any such two points along the axis of the cannula, regardless of the value of PED, the DV values $y_1$ and $y_2$ and the distance between the points d must satisfy the equation:

$$BetaDireccos_{gtang} = (y_2 - y_1)/d \qquad (1)$$

Equation (1) implies, by substitution and rearrangement, that the "insertion-axis adjustment" that will bring the tip of the cannula from earbar zero (0, 0, 0) to the final prescribed position (MLtip, DVtip, APtip) has the length:

$$d = DVtip/BetaDirecCos_{gtang} \qquad (2)$$

If the reading on the "DV" scale (the vertical slide 120) was originally DVZ, then after the adjustment it will be:

$$AX = DVZ - (DVtip/BetaDireccos_{gtang}) \qquad (3)$$

The guide-tube cannula direction cosines are signed, as noted above (Part III Step 2 Equation (17)), to reflect the signed distance from the cannula "top" to the cannula "tip". Correspondingly, the quantity ($DVtip/BetaDirecCos_{gtang}$) measures the signed distance, in the same direction, from the DVtip level to the zero level. But the adjustment desired is the AX adjustment on the vertical scale, which is the distance from the zero level to the DVtip level. Therefore the quantity d must be subtracted as shown.

Figure 8:
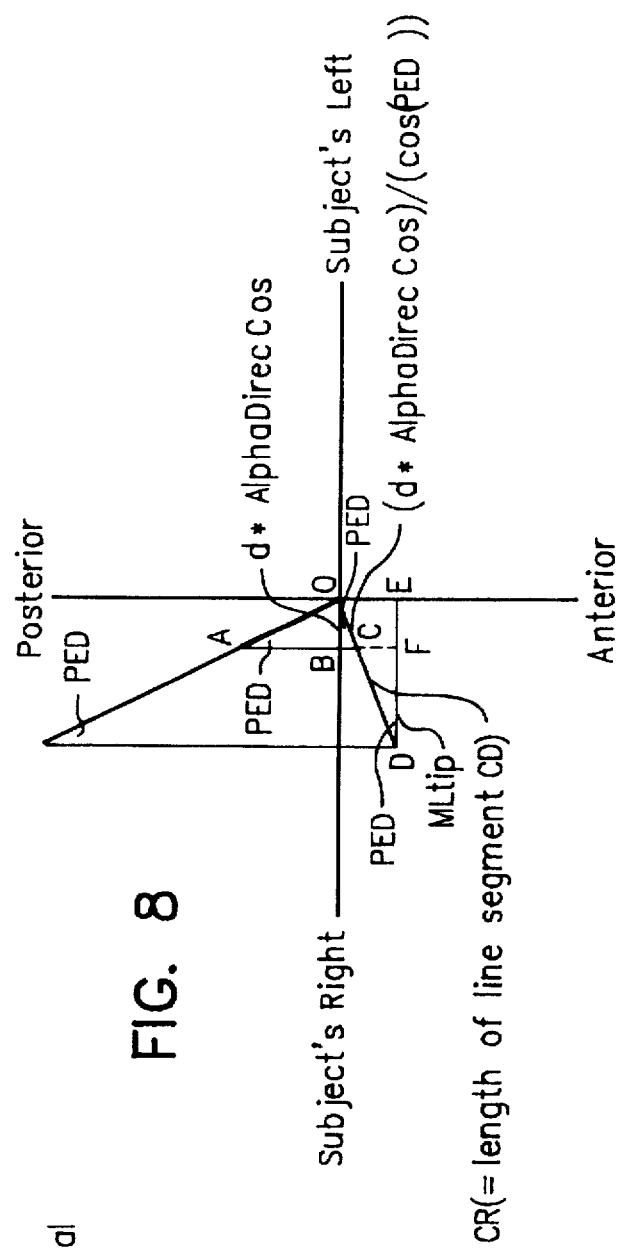
FIG. 8 illustrates geometrically the CR adjustment across the insertion axis for a device of the present invention, as mounted on a Kopf stereotactic instrument (Description of Specific Embodiment, Part VI, Step 2).

2. A second step is to make the cross-field adjustment. For the adjustment along the horizontal slide 195, it is helpful to picture the projection of the tip of the guide-tube cannula 20 onto the axial plane (ML/AP plane; XZ plane) as it moves during the adjustments (FIG. 8).

Point O represents the location of earbar zero, and line DE represents the distance MLtip from earbar zero. After the angle adjustments PED and ROT have been made and the cannula has been zeroed, its tip is at point O. The insertion-axis adjustment (just calculated in Part VI Step 1) along the direction of the guide-tube cannula moves the tip of the cannula along the axis of the cannula d millimeters from a position ($x_1$, $y_1$, $z_1$) to a position ($x_2$, $y_2$, $z_2$). (The projections of these points onto the XZ plane are labeled O and A, respectively, in FIG. 8.) This distance d must satisfy the equation:

$$AlphaDirecCos_{gtang} = (x_2 - x_1)/d \qquad (1)$$

This implies, by substitution and rearrangement, that the "DV" adjustment d along the direction of the guide-tube cannula that brings the tip of the cannula from earbar zero (0, 0, 0) to a position (ML, y, z) has the length:

$$d = ML/AlphaDirecCos_{gtang} \qquad (2)$$

and that the effect of such an adjustment on the ML position of the tip will be:

$$ML = d \ast AlphaDirecCos_{gtang} \qquad (3)$$

Figure 5:
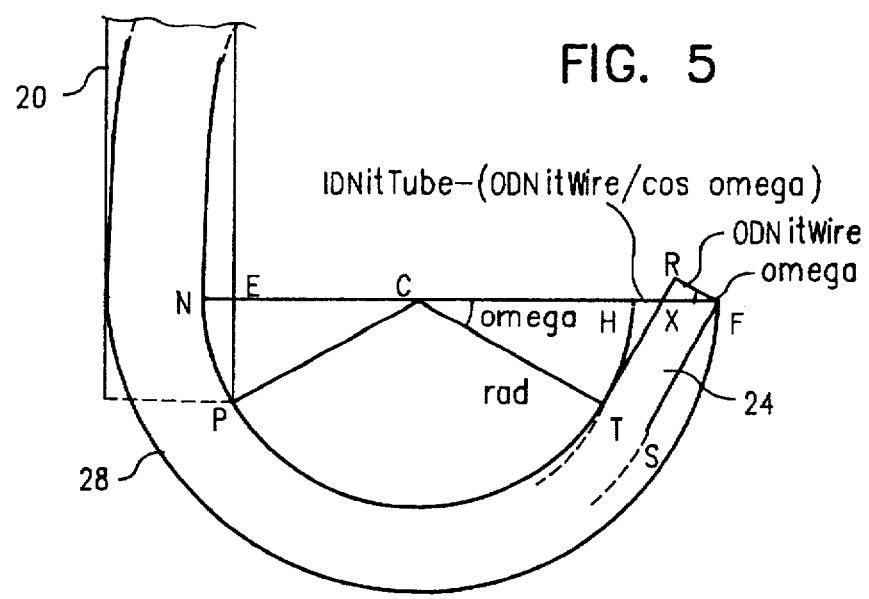
FIG. 5 illustrates a partial cut-away view of the device of FIG. 1, emphasizing the initial curvature of the curved cannula within the straight guide-tube cannula, and the initial straight portion of the innermost wire within the curved cannula (Description of Specific Embodiment, Part V, Step 1).

The line segments OA, OB, and OC all cover the same X distance ($ML = d \ast AlphaDirecCos_{gtang}$) in the projection diagram (FIG. 8); for line OB along the X axis itself this distance is equivalent to its length. If this X distance were the X distance prescribed by the Core Algorithms as MLtip, no further adjustment would be necessary. If some other X distance is prescribed, however, then a further adjustment CD will need to be made along the horizontal slide 195 (the "cross-field" slide) of the stereotactic instrument. The projection of this adjustment on the XZ plane (line segment CD, and by extension line segment OD) is perpendicular to the projection of the insertion-axis adjustment AO, because the horizontal slide 195 is perpendicular to the vertical slide 120 on the stereotactic instrument (FIGS. 4–5). Therefore, the angle PED is repeated in the triangle OBC, formed by the intersection between OD and the extension of line segment AB, as illustrated. Therefore the line OC has the length:

$$OC = (d \ast AlphaDirecCos_{gtang})/(\cos(PED)) \qquad (4)$$

This line segment, which marks the effect of the insertion-axis adjustment on the X position, and the line segment CD, which marks the additional distance to be moved along the horizontal slide to reach the final X position, compose the line OD in triangle ODE. The angle PED is again repeated in triangle ODE, so that:

$$\cos(PED) = DE/OD \qquad (5)$$

The known lengths of DE (MLtip) and OC (Equation 4), together with the unknown length CD can be substituted in Equation (5) to provide:

$$\cos(PED) = MLtip/[CD + (d \ast AlphaDirecCos_{gtang})/(\cos(PED))] \qquad (6)$$

Simplifying and rearranging Equation (6) provides:

$$CD \ast \cos(PED) = MLtip - (d \ast AlphaDirecCos_{gtang}) \qquad (7)$$

which provides the value of CD:

$$CD = [MLtip - (d \ast AlphaDirecCos_{gtang})]/[\cos(PED)] \qquad (8)$$

The value of d can now be substituted from Part VI Step 1 Equation (2) above, to yield:

$$CD = [MLtip - ((DVtip/BetaDirecCos_{gtang}) \ast AlphaDirecCos_{gtang})]/[\cos(PED)] \qquad (9)$$

In practice, to meet the requirements of the sign convention (right negative, left positive), and to permit use of the carrier on either arm of the stereotactic, this formula can be modified by using the variable SideArm (introduced in Part V Step 3 Equation (5)):

$$CD = SideArm \ast [MLtip - ((DVtip/$$

$$BetaDirecCos_{gtang})*AlphaDirecCos_{gtang})]/[\cos(PED)] \quad (10)$$

If the reading on the "ML" scale (the horizontal slide) was originally MLZ, then after the adjustment the final reading will be:

$$CR=MLZ+CD \quad (11)$$

or:

$$CR=MLZ+SideArm*[MLtip-((DVtip/BetaDirecCos_{gtang})*AlphaDirecCos_{gtang})]/[\cos(PED)] \quad (12)$$

3. A third step is to make the along-field adjustment. This involves positioning the carrier (essentially consisting of items 120, 160, 170, 190, 195) along the stereotactic arm 110. For the final adjustment, it is necessary to take into account the effects of the insertion-axis adjustment and the cross-field adjustment on the along-field position of the guide-tube cannula tip.

The insertion-axis adjustment described above in Part VI Step 1, of magnitude d along the direction of the guide-tube cannula, moves the tip of the cannula along the axis of the cannula d millimeters from a position $(x_1, y_1, z_1)$ to a position $(x_2, y_2, z_2)$. This distance d must satisfy the equation:

$$GammaDirecCos_{gtang}=(z_2-z_1)/d \quad (1)$$

This implies, by substitution and rearrangement, that the insertion-axis adjustment d along the direction of the guide-tube cannula, which brings the tip of the cannula from earbar zero (0, 0, 0) to a position (X, Y, AP), has the length (dashed line PQ in FIG. 6):

$$d=AP/GammaDirecCos_{gtang} \quad (2)$$

and that the effect of such an adjustment on the AP position of the tip will be:

$$AP=d*GammaDirecCos_{gtang} \quad (3)$$

The effect of the cross-field adjustment (dashed line CF in FIG. 7) can be calculated directly from triangle CDF, since:

$$\sin(PED)=CF/CD \quad (4)$$

so that $$CF=CD*(\sin(PED)) \quad (5)$$

or, substituting for CD from Part VI Step 2 Equation (10) above:

$$CF=\{SideArm*[MLtip-((DVtip/BetaDirecCos_{gtang})*AlphaDirecCos_{gtang})]/[\cos(PED)]\}*(\sin(PED)) \quad (6)$$

The tip of the cannula must be placed at a distance APtip from earbar zero as prescribed by the Core Algorithms. The adjustments AP and CF (Equations (3) and (6)) have already been made, so the remaining distance to be covered is:

$$APslide=APtip-AP-CF \quad (7)$$

$$APslide = APtip - \quad (8)$$

$$(DVtip/BetaDirecCos_{gtang}) * GammaDirecCos_{gtang} -$$

$$\{Sidearm * [MLtip - ((DVtip/BetaDirecCos_{gtang}) *$$

$$AlphaDirecCos_{gtang})]/[\cos(PED)]\} * (\sin(PED))$$

If the reading on the AP scale (on the stereotactic arm) was originally APZ, then after the adjustment the final reading will be:

$$APadj=APZ+APslide \quad (9)$$

or:

$$APadj = APZ + APtip - \quad (10)$$

$$(DVtip/BetaDirecCos_{gtang}) * GammaDirecCos_{gtang} -$$

$$\{SideArm * [MLtip - ((DVtip/BetaDirecCos_{gtang}) *$$

$$AlphaDirecCos_{gtang})]/[\cos(PED)]\} * (\sin(PED))$$

VII. Machine-dependent output Algorithms

From a series of trajectory points and characteristics of the implantation tool to prescribed tubing measurements.

Figure 9:
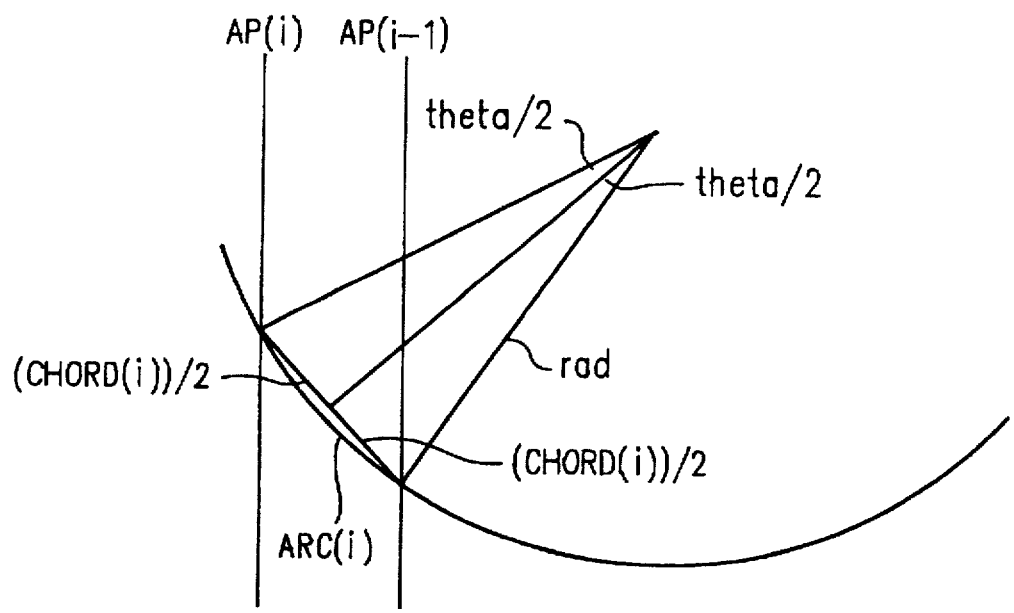
FIG. 9 illustrates geometrically the calculation of the length of the arc along the curvilinear portion of the trajectory from one intersecting parallel plane to the next, for an arcuate curvilinear trajectory, without helical torsion (Description of Specific Embodiment, Part VII, Step 1).

1. A first step is to determine, for the curved part of the trajectory, the length of the arc extending from one of the parallel planes to the next. Again, there are a number of ways to do this, as there are for doing most of the tasks to follow. One useful way is illustrated below. If the points are designated $(ML_{i-1}, DV_{i-1}, AP_{i-1})$ and $(ML_i, DV_i, AP_i)$, the length of the chord between the two points (FIG. 9) is:

$$CHORD_i=SQRT((ML_i-ML_{i-1})^2+(DV_i-DV_{i-1})^2+(AP_i-AP_{i-1})^2)) \quad (1)$$

The line bisecting the angle between the radii to the two points also bisects the chord and forms a right angle with it. The hypotenuse of the right triangle on either side of the bisector is the radius (rad) of the circle, and the base is half the chord. Therefore the sine of the angle (theta/2) between radius and bisector can be written as the base divided by the radius.

$$\sin(theta/2)=(SQRT((ML_i-ML_{i-1})^2+(DV_i-DV_{i-1})^2+(AP_i-AP_{i-1})^2))/2)/rad$$

or $$\sin(theta/2)=(SQRT((ML_i-ML_{i-1})^2+(DV_i-DV_{i-1})^2+(AP_i-AP_{i-1})^2)))/(2*rad) \quad (2)$$

Twice this angle is the angle that subtends the arc and therefore the angular length of the arc itself in radians.

$$theta=2*\arcsin((SQRT((ML_i-ML_{i-1})^2+(DV_i-DV_{i-1})^2+(AP_i-AP_{i-1})^2)))/(2*rad)) \quad (3)$$

This angular length times the radius gives the linear length of the arc.

$$ARC_i=2*rad*\arcsin((SQRT((ML_i-ML_{i-1})^2+(DV_iDV_{i-1})^2+(AP_i-AP_{i-1})^2)))/(2*rad)) \quad (4)$$

2. A second step is to cumulate these arc lengths all along the curved trajectory, by adding the arc lengths calculated above. The resulting series of increasing lengths provides the basis for calculating the arc length from any one point to any other point, simply by subtracting one cumulated arc length from the other. Two such sets are constructed, for different purposes, one beginning with the most posterior point on the circle, and the other beginning with the guide-tube cannula tangent point.

3. A third step is to determine, for the straight parts of the trajectory, the length of the line extending from the tangent point to the intersection point with each of the parallel planes. This provides for each tangent a series of lengths that is comparable to the series for the arcuate portion derived above.

If the intersection point is designated $(ML_i, DV_i, AP_i)$, the distance along the guide-tube cannula, for example, is simply:

$$LEG_i = SQRT((AP_i - AP_{gtang})^2 + (ML_i - ML_{gtang})^2 + (DV_i - DV_{gtang})^2) \quad (1)$$

4. A fourth step is the calculation of the points at the most extreme Z axis levels represented on the circle. A number of lengths are required as specifications, both for the metallic elements of the implantation tool and for the flexible implantable tubing itself. One additional calculation (this step) and several additional entries (next step) must be made to accomplish this.

There are a number of ways to visualize and calculate the most posterior and anterior points on the circle. One efficient way is illustrated below.

First, consider the circle plane (Part II Step 4 Equation 1):

$$AA*X + BB*Y + CC*Z + DD = 0 \quad (1)$$

Any plane parallel to the circle plane will have coefficients in the same proportion as coefficients (AA, BB, CC), which represent the direction components of any line perpendicular to the plane (Protter et al., supra, p. 546). The direction cosines of any such line can be computed from these numbers as:

$$AlphaDirecCos_{NORMAL} = AA/SQRT(AA^2 + BB^2 + CC^2) \quad (2)$$

$$BetaDirecCos_{NORMAL} = BB/SQRT(AA^2 + BB^2 + CC^2) \quad (3)$$

$$GammaDirecCos_{NORMAL} = CC/SQRT(AA^2 + BB^2 + CC^2) \quad (4)$$

(Love, supra, p. 128)

Figure 10:
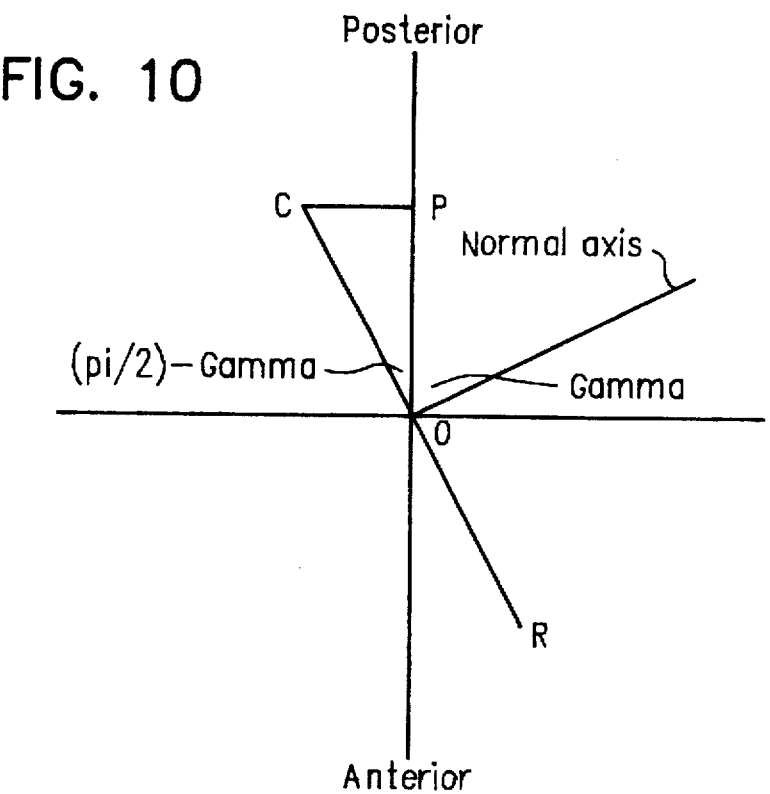
FIG. 10 illustrates geometrically the calculation of the most posterior and anterior points on the circle in which the curvilinear portion of the trajectory resides, in the case of an arcuate curvilinear trajectory, without helical torsion (Description of Specific Embodiment, Part VII, Step 4).

In particular, with reference to FIG. 10, consider the plane through the origin of the coordinate system and parallel to the circle plane. Translate the circle to this plane, with its center at the origin (O). The posterior point on the circle (C), at AP level P, will be in the same plane that contains the Z axis and the normal axis of the circle (the line normal to its plane and passing through its center). This plane is pictured in FIG. 10. Since the normal to the circle is in the plane, the circle necessarily appears as a straight line (CR, its projection onto this plane). The line segment OC is a radius (rad) of the circle. In the triangle OCP, it is evident that:

$$\cos(\pi/2 - Gamma) = OP/rad \quad (5)$$

so that the AP coordinate of the furthest posterior point (C) on the circle is:

$$OP = rad * \cos(\pi/2 - \arccos(GammaDirecCos_{NORMAL})) \quad (6)$$

Substituting from Equation (4) above provides:

$$OP = rad * \cos(\pi/2 - \arccos(CC/SQRT(AA^2 + BB^2 + CC^2))) \quad (7)$$

To calculate the most anterior and posterior planes containing a point on the circle, this length can be (respectively) added to or subtracted from the Z value of the actual center of the circle:

$$AnteriorAP = zz + rad * \cos(\pi/2 - \arccos(CC/SQRT(AA^2 + BB^2 + CC^2))) \quad (8)$$

$$PosteriorAP = zz - rad * \cos(\pi/2 - \arccos(CC/SQRT(AA^2 + BB^2 + CC^2))) \quad (9)$$

(10) The ML and DV values for these points (AnteriorML and AnteriorDV; PosteriorML and PosteriorDV) are available by application of Part II Step 4 Equation (10) and Part II Step 6 Equation (2).

5. A fifth step is the entry of certain additional values by the user.

a. Selection of proximal and distal points defined as the limits of the "target structure" along the trajectory In Part III Step 1 the points of tangency of the guide-tube cannula and the wire were selected by the user. These points condition the course of the trajectory itself, and were therefore included in the Core Algorithms above. The points of tangency do not necessarily—and in practice usually will not—represent the limits of the structure to be accessed. Once the trajectory is established, an independent pair of points on that trajectory has to be selected by the user to represent the beginning and end of the target structure.

As above, there are a number of ways in which the two points might be designated. One useful way is for the user simply to select one of the parallel planes for which the trajectory's intersection points have been calculated. One of these points is designated as (InitStructML, InitStructDV, InitStructAP), and the other as (FinalStructML, FinalStructDV, FinalStructAP) indicating their X, Y, and Z coordinates, respectively.

b. Selection of the entry and exit points on the body

Another pair of points to be designated, once the trajectory is established, are the body surface point at which the guide-tube cannula enters the body, and the exit point at which the wire emerges from the body. One way to provide these points would be to perform an image analysis of the scanner images, to permit the analysis to check after calculating each intersection of the trajectory with a coronal plane, to determine whether that point lies beyond the cranium. A simpler way is for the user to select the proper planes from the GUI output described above. One of these points is designated as (EntryML, EntryDV, EntryAP), and the other as (ExitML, ExitDV, ExitAP) indicating their X, Y, and Z coordinates, respectively.

For convenience, the AP levels of the labeled points defined on the circle and along the trajectory are listed here:
Parallel plane nearest the guide-tube cannula entrance to the cranium:

$$= EntryAP$$

AP coordinate of the most posterior point on the circle:

$$= PosteriorAP$$

AP coordinate of the tangent point at which the guide-tube cannula contacts the circle:

$$= APgtang$$

Parallel plane nearest the trajectory entrance to the target structure:

$$= InitStructAP$$

Parallel plane nearest the trajectory exit from the target structure:

$$= FinalStructAP$$

AP coordinate of the tangent point at which the wire leaves the circle:

$$= APwtang$$

AP coordinate of the most anterior point on the circle:

=AnteriorAP

Parallel plane nearest the guide-tube cannula exit from the cranium:

=ExitAP c. The following values as defined below are also to be entered by the user.

The desired distance, when the guide-tube cannula and curved nitinol tubing are fully advanced, between the lowest collar mount (bearing the cannula) and the second collar mount (bearing the curved nitinol tubing):

=FirstToSecondDisk

The desired length of wire to be showing above the cranium after full advancement:

=WireAboveHead

Normally the following value should be set to zero, but if APwtang equals AnteriorAP or PosteriorAP, then the point at which the wire emerges from the cranium cannot be calculated automatically and must be estimated by the user: The estimated length of nitinol wire from its point of tangency to the cranium:

=WireInHead

Similarly, if APwtang nearly equals AnteriorAP or PosteriorAP (nearer than SliceThickness), then it is convenient to include among the sample coronal planes an extra plane containing the point at which the wire reaches the surface of the cranium. For this purpose, the user may provide the distance from such an extra plane to AnteriorAP or PosteriorAP:

=SpecialWireIncrement

Likewise, if APgtang nearly equals AnteriorAP or PosteriorAP (nearer than SliceThickness), then it is convenient to include among the sample coronal planes an extra plane containing the point at which the cannula reaches the surface of the cranium. For this purpose, the user may provide the distance from such an extra plane to AnteriorAP or PosteriorAP:

=SpecialGuideIncrement

6. A sixth step is the summation of values to provide lengths for the preparation of tubing to meet the requirements of the Core Algorithms.

The designated coronal planes (Part VII step 5b) are used, in conjunction with the arc lengths and leg lengths determined in Part VII Steps 1–3, to summate the arc length and/or trajectory length from one designated point to another. For making these calculations, reference is made to two sets of cumulative lengths. One set (ARC) is defined, for planes from one point of tangency to the other, as the cumulative length of the arc of the circular path, starting from the point of tangency with the guide-tube cannula and ending with the designated point; for planes beyond the points of tangency, this set is defined as zero. The second set (LEG) is defined as zero for all points along the trajectory between the two points of tangency, inclusive; for points along the trajectories of the guide-tube cannula or the emergent wire, this set is defined as the distance from the given point to the respective point of tangency.

a. Circle (As written, the following definitions assume the target is entirely included in the circular portion of the trajectory; the first three lengths are therefore useful only if this is the case. In each case, what is meant by the definition is the difference between the cumulative arc length along the circle at the later point and the cumulative arc length at the earlier point.)

Posterior to targeted structure $$=ARC_{InitStruct}-ARC_{Posterior}$$

Within target $$=ARC_{FinalStruct}-ARC_{InitStruct}$$

Target to anterior point $$=ARC_{Anterior}-ARC_{FinalStruct}$$

Posterior to Anterior $$=ARC_{Anterior}-ARC_{posterior}$$

b. Trajectory (The following definitions are more general, making no assumption about the overlap of the target structure and the circular portion of the trajectory. If the trajectory is still within the target beyond the point of wire tangency, for example, the "TargetToWireTangency" becomes a negative number showing how far the target reaches beyond the point of wire tangency.)

CraniumToTangency $$=LEG_{Entry}-LEG_{gtang}$$

TangencyToTarget $$=ARC_{InitStruct}-ARC_{gtang}-LEG_{InitStruct}$$

WithinTarget $$=ARC_{FinalStruct}-ARC_{InitStruct}+LEG_{FinalStruct}+LEG_{InitStruct}$$

TargetToWireTangency $$=ARC_{wtang}-ARC_{FinalStruct}-LEG_{FinalStruct}$$

WireToCranium $$=LEG_{Exit}-LEG_{wtang}$$

TangentToTangent $$=ARC_{wtang}-ARC_{gtang}$$

C. Compound implantable tubing

Combinations of the Trajectory lengths (Part VII step 6b) are used in the construction of the compound implantable tubing, as follows.

The "leading" length of non-patent PAN-PVC tubing to be pulled in and implanted (on the guide-tube cannula "side" of the target structure) by retraction of the implantation tool:

Posterior Occlude=CraniumToTangency+TangencyToTarget

The length of patent PAN-PVC to be pulled in and implanted (in the target structure) by retraction of the implantation tool:

Patent Span=WithinTarget

The trailing length of non-patent PAN-PVC tubing to be pulled in and implanted (on the emergent wire "side" of the target structure) by retraction of the implantation tool:

Anterior Occlude=TargetToWireTangency+WireToCranium d. Implantation tool

Specifications for the implantation tool 10 itself are required for manufacturing.

Guide-tube cannula

Length of guide-tube cannula 20 in the block 15 and the lowest collar mount:

GuideCannulaInBlockAndLowestDisk=MountingBlockThickness+ CollarMountThickness

Length of guide-tube cannula 20 showing, from the bottom of the block 15 to the top of the cranium, when the tip of guide-tube cannula is in final position:

GuideFromBlockToCranium=$LE$-$SQRT$(($AP$tip−Entry$AP$)$^2$+($ML$tip−Entry$ML$)$^2$+($DV$tip−Entry$DV$)$^2$)

Length of guide-tube cannula 20 inside the cranium 150, from cranium to tip, in final position:

GuideInsideCranium=$SQRT$(($AP$tip−Entry$AP$)$^2$+($ML$tip−Entry$ML$)$^2$+($DV$tip−Entry$DV$)$^2$)

Total guide-tube cannula 20:

=GuideCannulaInBlockAndLowestDisk+GuideFromBlockToCranium+GuideInsideCranium

Nitinol tubing

Tubing in the block 15 and lower collar mount 16 and middle collar mount 14:

NitinolTubingInBlockAndDisks=MountingBlockThickness+ (2*CollarMountThickness)

Tubing from the bottom of the block 15 to the tip of the guide-tube cannula 20:

TubingInGuide=$LE$−CurveInGuideLength+CurveInGuideArcLength

Length of the nitinol tubing 28 from the tip of guide-tube cannula 20 to the emergence of nitinol wire 24 from the nitinol tubing 28:

TubingTravel=TangentToTangent−CurveInGuideArcLength+ StraightWireArcLength

Total nitinol tubing 28

=NitinolTubingInBlockAndDisks+TubingInGuide+TubingTravel

The nitinol tubing 28 should be manufactured with the curvature extended slightly beyond what is necessary—the slight excess includes the concealed CurveInGuideArcLength, and a little extra which will be concealed in the guide-tube cannula 20 and have no influence on the trajectory:

PlannedExcessArc=1+$INT$(CurveInGuideArcLength+0.5)

Nitinol tubing straight part:

=NitinolTubingInBlockAndDisks+TubingInGuide−PlannedExcessArc

Nitinol tubing curved part:

=TubingTravel+PlannedExcessArc

Nitinol wire 24

The length of nitinol wire 24 in the block 15 and the collar mounts 16, 14, 12, plus the length of the stop 30 between the lower and middle collar mounts 16, 14 when the wire is fully advanced:

NitinolWireInDisks=MountingBlockThickness+(3*CollarMountThickness)+FirstToSecondDisk The length of nitinol wire 24 from the bottom of the block 15 to the tip of the nitinol tubing 28:

WireInTubing=TubingInGuide+TubingTravel−StraightWireArcLength

The length of nitinol wire 24, from the nitinol tubing 28 to the point of emergence from cranium, plus the amount to be showing above cranium:

WireTravel=WireAboveHead+WireToCranium or, if WireInHead is given a non-zero value:

WireTravel=WireAboveHead+WireInHead

Total nitinol wire 24:

=NitinolWireInDisks+WireInTubing+WireTravel

Guide-rail

Third guide-rail (gauge 22):

=FirstToSecondDisk+2*CollarMountThickness+WireTravel

VIII. Alternative input methods

1. A first alternative is an alternative method for zeroing the guide-tube cannula 20.

Note that in Part VI it was assumed that the stereotactic carrier could be zeroed in the normal way, at earbar zero. For placements that involve relatively large angles PED and ROT, however, it is not possible or not convenient to reach both earbar zero and the point (MLtip, DVtip, APtip) at which the guide-tube cannula is to be set for the implantation. In this case, it is necessary to set up a second, non-angled "marker" carrier which can be zeroed at earbar zero and then conveyed to (MLtip, DVtip, APtip). The guide-tube cannula is then positioned to touch the same point, and the settings on the horizontal slide (CRzero), vertical slide (AXzero), and stereotactic arm (APzero) are recorded directly.

It is helpful, for purposes of checking the settings and the formulas, to back-calculate the location of earbar zero in this case, but it is not necessary. This back-calculation requires a number of formulas, the derivation of which can be shown by considerations similar to those in Part VI above. Therefore the formulas leading to this back-calculation are merely presented below, without derivation.

First, it is useful to express the effects, on X, Y, and Z position (all else equal), of an insertion-axis adjustment that increases "DV" position by 1 millimeter:

$AXml$Effect=−AlphaDirecCos$_{gtang}$ $AXdv$Effect=−BetaDirecCos$_{gtang}$ $AXap$Effect=−GammaDirecCos$_{gtang}$ (1)

Likewise, it is useful to express the effects, on X, Y, and Z position (all else equal), of a cross-field adjustment that increases "ML" position by 1 millimeter:

$CRml$Effect=SideArm*cos (*PED*)

$$CRdvEffect=0$$

$$CRapEffect=\sin(PED) \quad (2)$$

Since the stereotactic arm remains parallel to the Z axis, an along-field adjustment of 1 mm (all else equal) does not change ML or DV position, and changes AP position simply by the nominal 1 mm.

If adjustments are to be made on all three scales, then "all else" is not "equal". Since there is only one way to adjust DV, this adjustment is made first, conceptually. The insertion-axis adjustment that will bring the guide-tube cannula tip from DVtip to the DV of earbar zero is:

$$AXtoZero=DVtip/AXdvEffect \quad (3)$$

The effects of this move in the other two directions are:

$$AXtoZeroMLeffect=AXtoZero*AXmlEffect \quad (4)$$

$$AXtoZeroAPeffect=AXtoZero*AXapEffect \quad (5)$$

Since there is only one remaining way to adjust ML, this adjustment is made next, conceptually. The cross-field adjustment that will bring the guide-tube cannula tip from its new position to the ML of earbar zero is:

$$CRtoZero=(-MLtip-AXtoZeroMLeffect)/CRmlEffect \quad (6)$$

The effect of this move in the AP direction is:

$$CRtoZeroAPeffect=CRtoZero*CRapEffect \quad (7)$$

The along-field adjustment that will bring the guide-tube cannula tip from its new position to the AP of earbar zero is:

$$APadjtoZero=APtip-AXtoZeroAPeffect-CRtoZeroAPeffect \quad (8)$$

The calculated values for earbar zero are then:

$$MLZ=CRzero+CRtoZero$$

$$DVZ=AXzero+AXtoZero$$

$$APZ=APzero+APadjtoZero \quad (9)$$

If the values of Equation (9) are used as MLZ, DVZ, and APZ to calculate the AX, CR, and APadj values, they will arrive at the original inputs made at the beginning of this step.

2. A second alternative is an alternative input method, designed for making inputs from measurements in a brain atlas. The atlas may be a conventional atlas, or it may be a set of scanner images for which the .TIF files are not available.

This input method allows readings to be entered directly from the scanner images or atlas and provides scaling and offsetting to convert them to the surgical stereotactic coordinate system with origin at earbar zero. This method (assuming the pictures available are coronal views) requires from the user (1) a pair of distances, one number (ScaleMeasured) representing a length measured on the scanner image or atlas, and another (ScaleReal) representing the known corresponding distance in real millimeters; (2) for each of the three target points, its measured distance from the midline (MLmeas) and from the bottom of the picture (DVmeas), and the number of its coronal section (APmeas), in the series of coronal sections (in typical MRI sections this represents real millimeters from machine zero, but machine zero does not fall at the earbar zero AP); (3) the measured distance from the bottom of the picture for earbar zero (DVEZ) on the scanner image or atlas, and the number of the coronal section containing earbar zero (APEZ), in the series of coronal sections. The algorithms below convert these values into terms of real millimeters from earbar zero for the final entries ($ML_A$, $DV_A$, $AP_A$), ($ML_B$, $DV_B$, $AP_B$), ($ML_C$, $DV_C$, $AP_C$) suitable for the Core Algorithms.

The pair of distances provides a scale factor for converting the measured ML and DV values to real millimeters:

$$MRItoReal=ScaleReal/ScaleMeasured \quad (1)$$

The scale factor and the measured coordinates and earbar zero values are used to make the conversions for all three points as shown here for target point 1, and the results are provided to the Core Algorithms as the three original target points:

$$ML_A=[MLmeas_A]*MRItoREAL \quad (2)$$

$$DV_A=[DVmeas_A]*MRItoREAL-DVEZ*MRItoREAL \quad (3)$$

$$AP_A=[APmeas_A]-APEZ \quad (4)$$

Analogous conversions can be made in the opposite direction to provide the coordinates of the trajectory points on the scanner image or atlas, for each coronal section.

3. A third alternative is similar to the second, but instead of three points it takes input in the form of one point, the radius, and one angle of orientation (supplying the second angle of rotation by default).

This input method provides for a circle plane orthogonal to the axial plane (XZ: AP/ML), which can be "targeted" on a single point (target point 2), but placed transversely at a specified angle, rotated on its orthogonal (DV) axis from a conceptual "starting position" parallel to coronal plane. This method (also assuming the pictures available are coronal views) requires from the user (1) a pair of distances, one number (ScaleMeasured) representing a length measured on the scanner image or atlas, and another (ScaleReal) representing the known corresponding distance in real millimeters; (2) for only one target point, its measured distance from the midline ($MLmeas_B$) and from the bottom of the picture ($DVmeas_B$), and the number of its coronal section ($APmeas_B$) in the series of coronal sections; (3) the measured distance from the bottom of the picture for earbar zero (DVEZ) on the scanner image or atlas, and the number of the coronal section containing earbar zero (APEZ) in the series of coronal sections; (4) the desired angle of rotation from the coronal orientation (AxialRotation); and (5) the desired radius of the circle (WireRadius). The algorithms below convert these values into terms of real millimeters from earbar zero for the final entries ($ML_A$, $DV_A$, $AP_A$), ($ML_B$, $DV_B$, $AP_B$), ($ML_C$, $DV_C$, $AP_C$) suitable for the Core Algorithms.

The pair of distances provide a scale factor for converting the measured ML and DV values to real millimeters, as above, but also a scale factor for converting real millimeters to the scale represented by the measured values:

$$RealtoMRI=ScaleMeasured/ScaleReal \quad (1)$$

The scale factors, the measured coordinates and earbar zero values, and the selected angle and radius are then used to make the conversions for target points 1 and 3, while target point 2 is simply converted as shown under Part VIII Step 2 above:

$$ML_A=[MLmeas_B-SIGN(MLmeas_B)*WireRadius*REALtoMRI*\cos(AxialRotation)]*MRItoREAL \quad (2)$$

$$DV_A=[DVmeas_B+WireRadius*REALtoMRI]*MRItoREAL-DVEZ*MRItoREAL \quad (3)$$

$$AP_A=[APmeas_B+WireRadius*\sin(AxialRotation)]-APEZ \quad (4)$$

$$ML_B=[MLmeas_B]*MRItoREAL \quad (5)$$

$$DV_B=[DVmeas_B]*MRItoREAL-DVEZ*MRItoREAL \quad (6)$$

$$AP_B=[APmeas_B]-APEZ \quad (7)$$

$$ML_C=[MLmeas_B+SIGN(MLmeas_B)*WireRadius*REALtoMRI*\cos(AxialRotation)]*MRItoREAL \quad (8)$$

$$DV_C=[DVmeas_B+WireRadius*REALtoMRI]*MRItoREAL-DVEZ*MRItoREAL \quad (9)$$

$$AP_C=[APmeas_B-WireRadius*\sin(AxialRotation)]-APEZ \quad (10)$$

The results are provided to the Core Algorithms as original target points 1, 2, and 3.

4. A fourth alternative is an alternative input method, similar to Part VIII Step 3 above, designed for targeting a single given point, whether it is input from the GUI interface, from scanner images, from an atlas, or as a real value. It enables rotating the circle through two angles and specifying its radius. This input method is useful for targeting a small site with structures nearby that must be avoided by the entire trajectory.

This input method assumes that the input point has been pre-scaled by other algorithms to expression in terms of the stereotactic coordinate system with its origin at earbar zero; it requires from the user (1) inputs to provide a single target point ($ML_B$, $DV_B$, $AP_B$); (2) an angle HOR through which to twist the circle conceptually, with that target point as the base, from a coronal starting position; (3) an angle SAG to lever the circle down, with the "target point" as the only fixed point and with the circle's angular relationship to the sagittal plane maintained; (4) the desired size of the radius (siz); (5) the side to be treated (SideTreated: left +1, right −1). The algorithms below use these values to select the other two points ($ML_A$, $DV_A$, $AP_A$) and ($ML_C$, $DV_C$, $AP_C$) that will force the Core Algorithms to provide a circle that has the provided features.

The conceptual starting point is (1) a vertical guide-tube cannula; (2) a circle of the desired radius (siz), in a coronal plane, normal to the AP axis; (3) the target point ($ML_B$, $DV_B$, $AP_B$) fixed at the bottom center of the circle; (4) the other two points ($ML_A$, $DV_A$, $AP_A$) and ($ML_C$, $DV_C$, $AP_C$) originally 90° from it on either side of the circle. Before rotating, then, $$ML_A=ML_B-\text{Side Treated}* siz \quad (1)$$

$$ML_C=ML_B+\text{Side Treated}* siz \quad (2)$$

$$DV_A=DV_C=DV_B+siz \quad (3)$$

$$AP_A=AP_C=AP_B \quad (4)$$

The formulas perform the following conceptual steps:

First, rotate the circle by HOR around its vertical diameter, which is parallel to DVaxis, such that the medial 90° point moves posterior. For AP, this subtracts (siz*sin(HOR)) from the medial side, and adds (siz*sin(HOR)) to the lateral side. For ML, this adds ((Side Treated)*(siz−siz*cos(HOR))) to the medial point and subtracts (SideTreated*(siz−siz*cos(HOR)) from the lateral point. The axis remains vertical. The following formulas carry out this first maneuver:

$$ML_A=ML_B-\text{Side Treated}*siz*\cos(HOR) \quad (5)$$

$$ML_C=ML_B+\text{Side Treated}*siz*\cos(HOR) \quad (6)$$

Second, lever this vertical axis down within the sagittal plane by the angle SAG. The previously vertical axis is moving like the spoke of a wheel with the center at the bottom point. The circle moves along with it. For levering the top point of the axis back and down, a point just lateral to the center comes up a little, and a point just medial comes down a little to lie lower than the original DV of the bottom point.

The following intermediates simplify the formulas that follow:

$$angmed=SAG+\arctan(\sin(HOR)) \quad (7)$$

$$anglat=SAG-\arctan(\sin(HOR)) \quad (8)$$

$$mul=SQRT(siz^2+(siz*\sin(HOR))^2) \quad (9)$$

The following formulas carry out the second maneuver:

$$DV_A=DV_{B+mul}*\cos(angmed) \quad (10)$$

$$AP_A=AP_B-mul*\sin(angmed) \quad (11)$$

$$DV_C=DV_{B+mul}*\cos(anglat) \quad (12)$$

$$AP_C=AP_B-mul*\sin(anglat) \quad (13)$$

The starting point 2 ($ML_B$, $DV_B$, $AP_B$), which has not moved, and the adjusted target points 1 ($ML_A$, $DV_A$, $AP_A$) and 3 ($ML_C$, $DV_C$, $AP_C$) from Equations (5), (6), and (10) through (13) above, are then used as the three original target points for the Core Algorithms.

IX. Fitting a Three-Dimensional Helical Curve to a Set of Points

From an ordered series of four or more points to a helical curve fit to pass through or near these points.

Similar methods may be used to determine helical paths that include curvature in three dimensions. The methods outlined below describe the fitting of a helix to a set of input points, analogous to the determination of a circle from three points (Part II, Steps 1–3).

1. Strategy: An Overview.

(0) Consider n points in space, $\vec{x}_1=(x_1, y_1, z_1), \ldots, \vec{x}_n=(x_n, y_n, z_n)$, called "the data."

(1) Fit any curve $\vec{G}$ to or through the data, for example, segments of straight lines joining consecutive points, or a cubic spline through the data.

(2) Parameterize the curve $\vec{G}$ with its arclength. At all data points, estimate with finite differences or calculate with derivatives the following objects:

(2.1) the tangent vectors $\vec{T}:=d\vec{G}/ds$, $\vec{T}_1, \ldots, \vec{T}_n$, so that they all have unit length, $\|\vec{T}_i\|=1$;

(2.2) the derivatives $d\vec{T}/ds$ and the curvatures $\kappa_i:=\|d\vec{T}_i/ds\|$; the average curvature $\kappa:=(1/n)\Sigma_{i=1}^n \kappa_i$ serves as the curvature of the helix;

(2.3) the normal vectors $\vec{N}_1, \ldots, \vec{N}_n$, defined by $\vec{N}_i:=(1/\|d\vec{T}_i/ds\|)d\vec{T}_i/ds$;

(2.4) the binormal vectors $\vec{B}_1, \ldots, \vec{B}_n$, defined by the cross product $\vec{B}_i:=\vec{T}_i \times \vec{N}_i$, (2.5) the derivatives $d\vec{N}_i/ds$ and the torsions given by the dot product $\tau_i:=(d\vec{N}_i/ds)\cdot\vec{B}_i$; the average torsion $\tau:=(1/n)\Sigma_{i=1}^n \tau_i$ serves as the torsion of the helix.

(3) Fit a plane P to the normal vectors $\vec{N}_1, \ldots, \vec{N}_n$, for instance, by the method of total least squares (See, van Huffel et al., *The Total Least Squares Problem: Computational Aspects and Analysis*, Society for Industrial and Applied Mathematics, Philadelphia, Pa., 1991). (A cheap alternative might use the average of the binormal vectors, $(1/n)\Sigma_{i=1}^{n} \vec{B}_i$, as the normal to the plane, but that might prove unstable.)

(4) Compute the projections $\vec{P}_1, \ldots, \vec{P}_n$ of the data on the plane P.

(5) Fit a circle to the projections in the plane P, for instance, by the method of Moura & Kitney (*Computer Physics Communications*, 64, pp. 57–63, 1991). The radius $r_0$ of the fitted circle serves as the radius of the helix, and the axis of the helix now passes through the center of the fitted circle, perpendicularly to the plane P.

(6) Change to coordinates (u,v,w), with (u,v) in the plane P and w measured along the axis of the helix. Each data point now also has coordinates $(u_i, v_i, w_i)$.

(7) Cut a piece of the helix of height $w_n-w_1$, and shift it parallelly to the axis, so that its endpoints lie at the same heights as $\vec{x}_1$ and $\vec{x}_n$ respectively. Then rotate the piece of helix about the axis, so that the endpoints lie at the same minimum distance from $\vec{x}_1$ and $\vec{x}$ respectively.

(8) If desired, refine the fitted helix iteratively.

2. Introduction

An Example of Subroutines With Segments Between Data Points: The algorithm just outlined depends upon the initial curve $\vec{G}$ fitted to the data. The following subroutines illustrate the case with $\vec{G}$ consisting of segments of straight lines between the data, and for computing systems without compilers. Other curves will require other subroutines, but the functions of the subroutines remain the same regardless of the curve.

3. Organization of the Data

Because giving a different name to each data point may prove impractical, a two-dimensional array X may prove effective to store and manipulate the data, for instance, with the convention that:

$$x_{i,j} := (\vec{x}_j)_i$$

so that the j-th column of the array X contains the point $\vec{x}_j = (X_{1,j}, X_{2,j}, X_{3,j})$.

4. Subroutines for Arithmetic with Vectors

The following subroutines may prove efficient for an algorithm selected to fit a helix to points in space.

SAXPY$(a, \vec{p}, \vec{q})$.     4.1

The acronym "SAXPY" stands for "Scalar 'A' times X Plus Y," which constitutes a mnemonic device to remember that the subroutine SAXPY takes one number a and two vectors $\vec{x}$ and $\vec{y}$, and computes $(a \cdot \vec{x}) - \vec{y}$. The vectors $\vec{x}$ and $\vec{y}$ may also be columns of X. In the particular case $a = \pm 1$, the subroutine gives $\vec{x} \pm \vec{y}$. Specifically, SAXPY$(a, \vec{p}, \vec{q})$ is again a vector with three components, SAXPY$(a, \vec{p}, \vec{q})_1 := a \cdot p_1 - q_1$.

SAXPY$(a, \vec{p}, \vec{q})_2 := a \cdot p_2 - q_2$.

SAXPY$(a, \vec{p}, \vec{q})_3 := a \cdot p_3 - q_3$.

4.2. DOT$(\vec{p}, \vec{q})$

The subroutine DOT calculates the dot product of is two vectors:

DOT$(\vec{p}, \vec{q}) := p_1 q_1 + p_2 q_2 + p_3 q_3$.

4.3. SIZE$(\vec{x})$

The subroutine "SIZE" computes the Euclidean norm $\|\vec{x}\|_2$, also called length, of a vector $\vec{x} = (x_1, x_2, x_3)$ in space. Specifically, SIZE$(\vec{x})$ is a number, $$\text{SIZE}(\vec{x}) := \sqrt{\text{DOT}(\vec{x}, \vec{x})}.$$

4.4. CROSS

From two vectors, the subroutine CROSS calculates their cross product, $\vec{p} \, \vec{q}$, which has components CROSS$(\vec{p}, \vec{q})_1 := p_2 q_3 - p_3 q_2$ CROSS$(\vec{p}, \vec{q})_2 := p_3 q_1 - p_1 q_3$ CROSS$(\vec{p}, \vec{q})_3 := p_1 q_2 - p_2 q_1$.

5. Subroutine DELTA for the Distance Between Consecutive Points

The subroutine DELTA(X) calculates the Euclidean distance $d_j = \|\vec{P}_{j+1} - \vec{P}_j\|_2$ between two points $\vec{P}_j$ and $\vec{P}_{j+1}$, and the normed difference $(\vec{P}_{j+1} - \vec{P}_j)/d_j$, which has length 1, and stores all the results into two arrays, whose names may vary, denoted here by D with dimension n and S with dimension 3×n, so that:

$S_j$ is the j-th column of S, defined by $S_j := \text{SAXPY}(1, \vec{P}_{j+1}, \vec{P}_j)$ $D_j$ is the length of $S_j$, $D_j := \text{SIZE}(S_j)$.

Finally, divide $S_j$ by its length to get a vector of unit length:

$S_j := S_j / D_j$

6. Subroutine TNGTS to Compute Tangents: The subroutine TNGTS calculates the unit tangent vector at each data point and stores them into two arrays, D of dimension n and T of dimension 3×n:

T,D := DELTA(X).

Thus, $D_j = \|\vec{x}_{j+1} - \vec{x}_j\|_2$ and $\vec{T}_j = (\vec{x}_{j+1} - \vec{x}_j)/D_j$ for every j $\in \{1, \ldots, n-1\}$.

Other approximations of the tangent vectors with finite differences exist.

7. Subroutine CURVAT for the Normal Vectors and Curvatures

The subroutine CURVAT(T) computes the curvature and the normal vector at each data point, and stores the results into two arrays, K of dimension n and N of dimension 3×n.

N,K := DELTA(T)

Thus, $K_j = \|\vec{T}_{j+1} - \vec{T}_j\|_2$ and $\vec{N}_j = (\vec{T}_{j+1} - \vec{T}_j)/K_j$ for every j $\in \{1, \ldots, n-2\}$.

8. Subroutine BINORM for the Binormal Vectors

The subroutine BINORM calculates the binormal vectors and the torsions, and stores the results into two arrays, B of dimension 3×n, and Q of dimension n.

$B_j := \text{CROSS}(\vec{T}_j, \vec{N}_j)$.

$Q_j := \text{DOT}(\vec{N}_j, \vec{B}_j)$.

Thus, $B_j = \vec{T}_j \times \vec{N}_j$ and $Q_j = \vec{N}_j \cdot \vec{B}_j$ for every $j \in \{1, \ldots, n-2\}$.

9. Subroutine PRMTRS for the Parameters of the Helix

The subroutine PRMTRS estimates parameters for the helix: its curvature KH and torsion QH, and the radius r and step s in the parameterization of the helix.

KH:=(1/[n−2]) $(K_1+ \ldots +K_{n-2})$,

QH:=(1/[n−2]) $(Q_1+ \ldots +Q_{n-2})$, c:=KH$^2$+QH$^2$, r:=KH/c, s:=QH/c.

10. Subroutine PLANE for the Plane Perpendicular to the Axis

The subroutine PLANE fits a plane to the normal vectors, for instance, by means of the Total Least Squares algorithm described in van Huffel and Vandervalle, supra.

An alternative consists of using the average binormal vector as the direction of the axis, perpendicular to the plane, stored into an array W with three components:

W:=(1/[n−2])$(B1+ \ldots +B_{n-2})$,

W:=W/SIZE(W).

However, this alternative may prove too inaccurate if the data cover only a small portion of one period. Yet another possibility consists of approximating the normal to the plane by the vectors $\vec{w}_j := \vec{N}_j \times \vec{N}_{j+1}$ for $j \in \{1, \ldots n-3\}$, and then averaging such vectors:

W:=(1/[n−2])$(\vec{N}_1 \times \vec{N}_2 + \ldots + \vec{N}_{n-2} \times \vec{N}_{n-3})$,

W:=W/SIZE(W).

Again, the best method uses Total Least Squares, if it is available.

11. Subroutine BASIS for New Coordinate Axes

The subroutine BASIS produces an orthonormal basis (U,V,W), which consists of three mutually perpendicular vectors U,V, and W, each with length 1, and such that W coincides with the vector W from PLANE.

To this end, consider the unit vector W from PLANE as a matrix W with 3 rows and 1 column, and apply to W the QR factorization from numerical analysis. The last two columns of the matrix Q are the vectors U and V.

12. Subroutine PRJCTN for the Projections of the Data

The subroutine PRJCTN computes the projections $\vec{p}_1, \ldots, \vec{p}_n$ of the data onto the plane normal to the axis W, and expresses these projections in the system of coordinates with the basis (U,V,W). In the plane P spanned by the vectors U and V, the projections have coordinates $u_j = \vec{x}_j \cdot U = DOT(\vec{x}_j, U)$, $v_j = \vec{x}_j \cdot V = DOT(\vec{x}_j, V)$, which the routine PRJCTN may store in one two-dimensional array P, so that $P_{1,j} = u_j$ and $P_{2,j} = v_j$.

13. Subroutine CIRCLE for the Axis of the Helix

The subroutine CIRCLE fits a circle to the projections $\vec{p}1, \ldots \vec{p}_n$ in the array P, for instance, with the algorithm of Moura & Kitney, supra.

The circle then determines the axis of the helix, which passes through the center $(x_0, y_0, z_0)$ of the fitted circle along the direction of W.

The radius of the helix may be either the radius $r_0$ of the fitted circle, or the radius r computed above by the routine PRMTRS. (For exact fits, the two radii coincide with each other.)

14. Subroutine ROTATE to Position the Helix

The subroutine ROTATE starts a piece of helix at $\vec{x}_1$ with the parameters just described, and focuses on the discrepancy between $\vec{x}_n$ and the endpoint of the piece of helix, defined as the point where the helix crosses the plane with equation $w = w_n$. Then the subroutine rotates the helix by an angle $\phi$ to even out the discrepancies at $\vec{x}_1$ and $\vec{x}_n$.

15. Summary of the Crude Algorithm

Read the data into the array X.

Call TNGTS.

Call CURVAT.

Call BINORM.

Call PRMTRS.

Call PLANE.

Call BASIS.

Call PRJCTN.

Call CIRCLE.

Call ROTATE.

Results

An orthonormal basis (U,V,W), with W along the axis of the helix, a point $(u_0, v_0, w_0)$, center of the fitted circle, where the axis passes, the radius r of the helix, the step s of the helix, the angle of rotation $\phi$ to rotate the helix to fit the data better, the constant $a = 1/\sqrt{r^2 + s^2}$ for computational convenience, the curvature KH, and the torsion QH, of the helix, which now has the formula:

$u(t) = u_0 + r \cos(a \cdot t)$, $v(t) = v_0 + r \sin(a \cdot t)$, $w(t) = s \cdot a \cdot t$, for $w_1/(s \cdot a) \leq t \leq w_n/(s \cdot a)$.

EXAMPLES

Example 1

This example demonstrates an embodiment of the present invention which is further developed and refined in subsequent examples. Stereotactic neurosurgical implantation was performed with polysulfone (PS) and polyacrylonitrile polyvinylchloride (PAN-PVC) copolymer tubing through most of the length of the neostriatum by the methods of the present invention. The planned trajectory was confirmed by x-ray. A small amount of dye was allowed to diffuse into the brain all along the course of the tubing, confirming the circumfusion of the dye and the positioning of the tubing by examination of histological sections.

Post-mortem cranial and brain specimens from two adult female pigtailed macaques (*Macaca nemestrina*) were acquired from the Tissue Distribution Program of the University of Washington Regional Primate Research Canter. Euthanasia was performed by Nembutal overdose in the manner approved by the university.

A spreadsheet was devised to provide specifications for passing the needle through a given brain structure. Inputs to the spreadsheet included (1) the stereotactic coordinates (AP, ML, and DV) of three points to be included in the trajectory, (2) the guide-tube length and inner diameter, and (3) the outer diameter of the curved needle. The spreadsheet also provided a choice of species (longtailed macaque, pigtailed macaque, or baboon) by incorporating the locations of the anterior commissure in each species as a point of reference, as pictured in standard brain atlases. Formulations for adjusting the stereotactic position on the basis of ventriculography were also incorporated in the spreadsheet, but were not used for the post-mortem test, for which ventriculography would be impractical.

Based upon these inputs, the spreadsheet provided the diameter of curvature, the angle and position at which the guide-tube was to be inserted, the points at which the tubing would intersect coronal planes, and the length of curved tubing that would reach from the top of the guide-tube to the point at which it re-emerged from the brain. The spreadsheet was written in Excel for Windows in the Windows 3.0 environment (Microsoft Corp., Redmond Wash.), implemented on a Dell System 310 IBM-compatible 80386 microcomputer (Dell Computer Corp, Austin Tex.).

The spreadsheet was cued by entry of the length (35 mm) and internal diameter (0.965 mm) of the guide-tube (18-gauge thinwall), the outer diameter (0.330 mm) of the curved needle (29-gauge), the choice of species and reference atlas, and the stereotactic coordinates of three non-collinear points on the planned trajectory. From these coordinates, a series of automatic matrix operations in the spreadsheet derived the orientation of the plane (plane "PP") containing the three points to the standard stereotactic coordinates, and the coordinates of the center of the circle in PP specified by those three points. The center was determined by taking the three original points as the vertices of a triangle, for which the perpendicular bisector planes of each side must intersect in a line perpendicular to the plane PP and equidistant from the three points. The intersection of the plane PP with this line (i.e., with any two of these bisector planes) was the center of the circle in PP determined by the points.

The two intersection points of the circle and any given coronal plane were determined from the equations for PP, the circle, and the coronal plane. (For the planned trajectory, with the straight guide-tube lying in the most posterior coronal plane, the upper point was in the brain only for the most anterior coronal planes.) The direction cosines of the tangent (in PP) to the circle, at each of these intersection points, were determined from the intersection of PP with the plane perpendicular to PP and tangent to the circle at the given point. For a guide-tube of the given length placed at the angle specified by these direction cosines, the coordinates of the top and the tip were derived from the direction cosines, taking into account the fact that the curvature of the needle would begin inside the guide-tube at a calculable distance above its tip. These calculations were carried out for all coronal planes represented in the atlas.

The most posterior point on the circle was calculated numerically by substituting values to determine the minimal AP level at which there were real ML and DV values. At this point, the angle of the tangent-plane with the AP axis in the sagittal plane must be 90°. The spreadsheet provided the coordinates of the top of the guide-tube when the tip was inserted to this point, allowing confirmation that the guide-tube length was sufficient to clear the top of the skull and allow for insertion of the circular needle.

The spreadsheet also provided two other coronal levels, at which the trajectory was expected to lie (1) outside the brain for the first time and (2) furthest outside the brain, when the needle was maximally inserted in the guide-tube. The spreadsheet provided the length of tubing required for the trajectory, including the portion above and within the guide-tube, as well as the portion circling through the brain and extending outside the brain at maximal insertion.

The putamen was targeted for implantation by the preparations. The head was positioned in the stereotactic instrument and scalp and bone tissue were removed from the working area. The carrier was moved to the anteroposterior (AP) position over the post-central gyrus specified by the spreadsheet, the mediolateral (ML) scale adjustment was made as specified, and the guide-tube, with a stylet inserted, was lowered by the stereotactic dorsoventral (DV) adjustment to the specified DV scale position (final location of tip: P2, R11.1, D29.7, relative to earbar zero). The stylet was removed and the curved needle inserted. A 29-gauge needle, curved to the specified radius, was lowered through the guide-tube, and as it passed out the tip of the guide-tube and through the brain, the plane of its emerging arc was kept parallel to the side of the rectangular needle-holder. When its tip emerged through the surface of the prefrontal cortex (about A25), it was inserted further into the guide-tube to bring the tip about 3 mm out of the brain. PS tubing (Amicon, Danvers Mass.; MW cutoff 100,000 Da, OD 0.5 mm, from H1P100-20 Diaflo Hollow Fiber Cartridge), or PAN-PVC tubing (MW cutoff 50,000 Da, OD 1.0 mm), previously cleared of glycerine by ultrafiltration with physiological saline and kept moist and filled in a saline bath, was fastened to the tip of the needle with Vetbond (Tissue Adhesive, N. 1469; 3M Animal Care Products, St. Paul Minn.). The needle was slowly withdrawn, retracing its course, pulling the polymer tubing into prefrontal cortex, down through the length of the neostriatum, and up to the lower tip of the guide-tube. The guide-tube, containing the curved needle and pulling the polymer tubing at its tip, was then raised by the stereotactic DV adjustment.

The radius of curvature of the needle, the angle at which the guide-tube was inserted, the points at which the tubing intersected coronal planes, and other useful parameters were provided by customized spreadsheet software as described above.

The 29-gauge insertion needle was curved to the diameter specified by the spreadsheet by (1) wrapping needle stock several times in a tight helix around a mandrill rod of about 0.25 the desired diameter, (2) passing the resultant coil through the guide-tube, and (3) manually adjusting the helical displacement to approach a circular contour.

A Kopf stereotactic instrument (#1404, David Kopf Instruments, Tujunga Calif.) was set with the rotary scale on the carrier facing squarely anterior, so that at a given AP level, the stereotactic shaft (mounted by the carrier to the stereotactic arm), along which DV adjustment is normally made, could move only in a plane vertical to the stereotactic horizontal. Because a guide-tube oriented tangential to the most posterior point of the circle must have a vertical trace, as viewed from the side, this placement pre-determined the first of three components of the proper setting for the plane PP.

A custom-designed needle-holder, in the form of a rectangular stainless-steel block, was mounted to the lower end of the stereotactic shaft by a universal ball-joint. The ball-joint was first adjusted to bring the needle parallel to the stereotactic shaft along which DV adjustment is normally made; this was accomplished by setting this shaft to vertical, loosening the ball joint, placing a rectangular, precision-machined, stainless-steel calibration bar squarely across the arms of the stereotactic instrument, adjusting the DV setting until the needle-holder sat squarely on the bar, then tightening the ball joint. The stereotactic shaft was then rotated by an angle prescribed by the spreadsheet and drawn with a protractor on the calibration bar; the plane PP now stood orthogonal to the stereotactic horizontal but at an acute angle to the stereotactic sagittal plane. With the shaft tightened in place, the third component was provided by adjusting the rotary scale on the carrier to an angle prescribed by the spreadsheet. With the angles fully adjusted, the tip of the guide-tube in the needle holder was brought to earbar zero, and the AP, ML, DV settings were recorded in the spreadsheet.

A ventriculography could have been performed in a living monkey, to bring the intercommissural line parallel to stereotactic horizontal and to locate the anterior commissure within the adjusted coordinate system with greater accuracy than available from the atlas alone. The spreadsheet allowed the necessary inputs to be made, but for the post-mortem test material, this step was omitted and the atlas values were considered the best estimates available.

The spreadsheet combined the AP, ML, and DV earbar zero scale readings, the estimate of the position of the anterior commissure, and the location of the point most posterior on the circle, to provide the AP, ML, and DV settings for lowering the guide-tube to the proper position.

With both ends protruding from the brain, the tubing was filled with radio-opaque iohexol (Sterling-Winthrop) and a lateral x-ray was taken to confirm the position and contour of the implant. The iohexol was then replaced with a 0.75% solution of malachite green dye. The dye was replaced with fresh dye every 30 min for 1.5 h (PAN-PVC tubing) or 3 h (PS tubing), to test for diffusion into the brain parenchyma surrounding the tubing. Finally, 10% formalin was introduced into the tubing, the brain was removed and blocked, and the portion containing the tubing was fixed by immersion in formalin for 24 h, then cryoprotected by immersion in 30% sucrose for 3 days. Coronal frozen sections were cut at 1-mm intervals throughout the course of the implant and mounted on glass slides. One series was compared with the 1-mm intervals in the brain atlas and the best match for each section was selected. The position of the implant in the section was transferred by reference to the comparable neighboring structures in the atlas, and the ML and DV levels of that position were then read from the atlas. The measured readings for each section were compared with the planned position for that section provided by the spreadsheet.

The implanted tubing was located in the dorsal half of the neostriatum for approximately 16 mm, reaching 80% of the AP extent from the anterior tip of the caudate to the posterior tip of the putamen. A halo of green dye surrounded the tubing in each section, fading at the edges, with a diameter of about 2 mm.

X-rays displayed a smooth course with a shape very similar to that predicted for a lateral view of the planned trajectory. The sequence of 1-mm coronal sections matched well with sections in the atlas. Within the measured series both the posterior and anterior limits of the trajectory were located about 2 mm posterior to the expected positions relative to the anterior commissure. For the other two dimensions, measurements from histological slides (PS tubing) indicated a trajectory generally more dorsal by about 2 mm and slightly more medial than planned at many points.

This study has demonstrated that permselective polymeric tubing can be accurately implanted over a substantial distance in a primate brain, leaving both ends available for the introduction of biochemicals, which are then free to diffuse out of the tubing and into the brain parenchyma. In tissue from the test subjects, the implant passed through most of the length of the neostriatum. The x-ray indicated a smooth trajectory for the polymer tubing, as planned, suggesting that irregularities in the rough numerical ML and DV estimates, made from the mounted sections, were due largely to measurement error associated with routine histological procedures. The measurements from histological slides indicated non-random systematic errors in the location of the trajectory, attributable to the variation of the individual animal from the estimate provided by the atlas. Placement was reasonably accurate, but the relative positions of bony and brain landmarks can vary substantially, making it necessary in nonhuman primates to improve stereotactic accuracy by performing ventriculography or magnetic resonance imaging in the living animal. Such a procedure was not possible for this post-mortem tissue, so that small errors in the placement of the circular trajectory were to be expected. The apparent deviations suggest that in this tissue, as positioned in the stereotactic instrument, brain landmarks were located 2 mm anterior, 2 mm ventral, and 0.8 mm to the right of their atlas locations. Compensation for these errors due to the deviation of this subject from the atlas series would have further improved the accuracy of placement.

The green haloes around the tubing in tissue sections were of dimensions comparable to those seen after point injections of malachite green in rodents (Myers, *Physiol. Behav.*, 1, p. 171, 1966). This suggests that passive diffusion is ample for passage of a biochemical, highly concentrated in the tubing, into surrounding brain tissue, even post-mortem. Beyond this observation, the distance covered by this diffusion over 1.5–3 h, in post-mortem tissue, with occasional replacement of the fluid in the tubing from a reservoir, cannot be assumed to represent the distance that would be covered by an endogenous biochemical such as dopamine applied chronically in a similar manner. This distance should be expected to depend not only on the concentration, the number of hours or days of treatment, and the rate of replacement, but also on the presence of co-infused metabolic inhibitors, the geometry and fluid dynamics of the extracellular space in gray and white matter, and long-term brain biochemical adaptations that may occur in response to the chronic presence of a source of biochemical.

PAN-PVC has been shown to be highly biocompatible with brain tissue, with inflammation subsiding after a few weeks and the astrocytic zone around the implant decreasing from over 400 μm to under 40 μm over 12 weeks (Winn et al., *Exper. Neurol.*, 105, pp. 244–250, 1989). The chronic presence of a stable high concentration of a biochemical in a renewable, biocompatible source that is well-integrated into the brain should lead to a steady state in which much of the neostriatum can be profoundly influenced from a single implant. In rats with unilateral substantia nigra lesions, infusion of dopamine by implanted cannula over several days into brain tissue has been shown to have substantial effects on apomorphine-induced rotational behavior and on striatal levels of dopamine, while intraventricular infusion at the same rate had no behavioral effect and raised dopamine levels only within 1 mm of the ventricle (Kroin et al., *J. Neurosurg.*, 74, pp. 105–111, 1991). Chronic infusion of labeled dopamine by a standard cannula over several days in rabbits has led to measurable label as far as 10 mm from the cannula tip (Sendelbeck and Vrguhart, *Brain Res.*, 328, pp. 251–258, 1985). We have shown in an earlier study (Dubach, *Neuroscience*, 45, pp. 103–115, 1991) that acute point injections of highly concentrated dopamine, along with an inhibitor of monoamine oxidase, can leave high tissue levels elevated for as long as two hours after injection, over a region that extends more than 3 mm from the center of the site.

Example 2

Striatal implantations and subsequent rotational observations were made in two baboons (*Papio cynocephalus*), and the parahippocampal region has also been implanted in a long-tailed macaque (*Macaca fascicularis*).

The baboons were treated unilaterally with the dopamine neurotoxin MPTP via the carotid artery several months before implantation using the technique originated by Bankiewicz et al. (*Life Sci.*, 39, pp. 7–16, 1986). Flow was directed from the common carotid up into the internal carotid during the infusion by occluding the external carotid. The internal carotid was easily distinguishable by its deep passage into the neck in the baboon; the two more superficial branches of the external carotid artery typically bifurcated immediately upon leaving the common carotid. The infusion rate (60 cc over 12 minutes) was slightly faster than that of Bankiewicz (60 cc over 15 minutes) (Bankiewicz et al., supra). Isoflurane anesthesia (Kordower et al., *J. Neurosurg.*, 73, pp. 418–428, 1990) was used for the lesion surgery. A high concentration of MPTP (1 mg/kg, 2.5 times the concentration used by Bankiewicz) was required for consistent results in baboons; possibly this is because the brain/body ratio is larger, so that to get the same amount to the brain requires a larger "per kilogram body weight" amount.

Calculations for planning trajectories were organized in the form of a spreadsheet implemented under Microsoft Excel (Microsoft Corp., Redmond Was.). The spreadsheet was augmented by access to magnetic resonance image (MRI: General Electric 1.5 Tesla) files manipulated by Microsoft Visual Basic and displayed by Adobe Photoshop in a Microsoft Windows environment. Inputs included the dimensions of the tubing and wire, landmarks that established the orientation of the brain in a coordinate system shared by the MRI and the stereotactic instrument, and three points through which the implant was intended to pass. The spreadsheet derived the orientation of the plane and the center and radius of the circle in that plane that were specified by the three "target" points. From these results it determined the intersection points of the circle with each coronal plane, if any, and the direction cosines of the tangent to the circle at each intersection point. Two tangent locations on the circle (for the guide-tube cannula and for the emergent straight wire) were selected by the user by choosing two of these coronal planes. Given the tangent selected as the course of the guide-tube cannula, the spreadsheet determined the coordinates of the tip of the cannula at full insertion (taking into account the curvature of the tubing that would remain inside the tip of the cannula) so that the user could zero the stereotactic equipment appropriately. The user entered the zero settings in the spreadsheet. The user also specified the coronal planes at which the trajectory would be expected to enter and exit the target structure, and the coronal planes at which the tangents (cannula and wire) would be expected to intersect the cranium. Output cells in the spreadsheet then reflected the stereotactic angle settings and Vernier-scale settings for the guide-tube cannula, and the required lengths of nitinol tubing, nitinol wire, and permselective implant tubing.

MR images were made for each monkey as an aid to stereotactic placement. A non-ferrous stereotactic instrument was designed and built for this and other projects, in the Regional Primate Research Center Machine Shop. The "spoiled GRASS" format on the GE 1.5-tesla magnet was used for making these images. This format provides a "voxel" (3-D pixel) that is 0.8 mm on a side, resulting in an accurate, continuous, customized "atlas" of each monkey's brain.

The spreadsheet provided several options for planning various types of trajectories, including a Graphical User Interface option, by which as many as 30 coronal MR images were displayed simultaneously on the monitor screen. Individual images could be enlarged and the location of landmark and target points entered graphically by a mouse. The system transferred these coordinates to the spreadsheet, which calculated the trajectory passing through the target points, and projected onto each of the 30 coronal views a marker for the point at which the tubing would pass through that section. This set of views greatly simplified evaluation and adjustment of a putative trajectory and determination of the planes near which that trajectory entered and exited the cranium and the target structure.

The putamen (or the parahippocampal cortex in the long-tailed macaque) was targeted for implantation by computer methods outlined above. The implantation consisted of establishing a curvilinear course down into and back up out of the brain with a shaped metal leader, and then drawing a piece of flexible tubing in the reverse direction back through the brain along that course. A telescoping set of concentric lengths of metal tubing and wire traveled along the planned course down into the brain. A stainless-steel guide-tube cannula (21-gauge encased in 18-gauge) passed through a burr-hole in the cranium and entered the brain at a prescribed point on the cortical surface and followed a straight line down to a "tangent point." At that point a radially curved span of nitinol tubing (approximately 26-gauge) emerged to trace an arc in the depths of the brain around to another prescribed point. At that point a length of fine nitinol wire (10-mil) emerged tangentially from the curved tubing and traveled up out of the brain along a straight line, to pierce through the cortical surface from underneath at a point not far from the original entry point. Nitinol, a "superelastic" nickel-titanium alloy, permits a much tighter curvature than stainless steel, as well as enabling the use of the fine wire to trace the second straight leg of a "hairpin" course through the brain. The cannula, curved nitinol tubing, and straight nitinol wire were mounted by set screws respectively into lower, middle, and upper stainless-steel collar mounts (disks), which were kept in register by similarly mounted guide rails. The guide-tube cannula extending from the lowest disk was mounted by set screw into a stainless-steel block fastened to a needle carrier on a conventional Kopf stereotactic instrument (#1404, David Kopf Instruments, Tujunga Calif.). During insertion, the final passage of the wire was stopped short of the underside of the cranium, x-rays were taken to confirm the point at which it would emerge, and another burr-hole was made in the cranium.

When the metallic elements were fully inserted, with the nitinol wire emerging from the brain, a length of polyethylene tubing (PE-10) was fastened to the wire with cyanoacrylic glue (Vetbond: Tissue Adhesive, N. 1469; 3M Animal Care Products, St. Paul Minn.) and the disks anchoring the wire and tubes were raised in series, pulling the PE-10 down into and back up out of the brain, following the same trajectory in reverse order. The PE-10 tubing had previously been glued into a length of permselective polyacrylonitrile polyvinylchloride (PAN-PVC) copolymer (MW cutoff 50,000 Da, OD 1.0 mm) tubing, in such a way as to provide a patent span of PAN-PVC in the targeted region of the brain and non-patent segments lined with PE-10 extending from this span up out of the brain; the span lengths were all read from the spreadsheet. The construction of the compound PE/PAN-PVC tubing was accomplished by (1) first slipping a length of PAN-PVC (one of the occluded segments) all the way onto the PE-10, (2) then inserting the tip of the PE-10 just inside another length of PAN-PVC (the patent span), (3) placing a small amount of Vetbond on a mark 5 mm up the PE-10, and (4) pushing it into the PAN-PVC tubing up to the mark, (5) then sliding the previously mounted PAN-PVC segment down to the glue joint. Another length of PE-10 was connected with the patent span of PAN-PVC at the other and in the same manner. This compound flexible tubing was then pulled far enough into the brain that the patent semi-permeable portion was exposed to the target area and the internally reinforced (PE-10) and externally biocompatible (PAN-PVC) tubing passed through remaining brain areas and the cranium. Tubing was bathed in saline as it passed into the brain. The friction at the brain/tubing interface was small enough, and the support provided by the brain as the tubing passed around the radial curve was large enough, that the PAN-PVC/PE-10 tubing traveled along the course established by the nitinol and stainless steel, which pierced but not did not tear the brain tissue.

The burr-holes in the cranium, which provided access to the brain for the tubing, were repaired by placing a thin layer of gelfoam at the depth, applying Vetbond to the sides of the hole and to 1–2 mm of the cranial surface surrounding the hole, and then introducing a few drops of Kooliner acrylic. The PAN-PVC tubing (reinforced with PE-10) that emerged from the brain was thus joined firmly to the cranium. A length of PE-50 tubing, previously sleeved in silicone tubing for tissue compatibility and passed subcutaneously from a point of emergence on the back up to cranial incisions, was joined with Vetbond and silk suture to the PE-10. This continuous length of tubing was then sutured to the scalp during closure, so that the entire implant—acrylic and compound PAN-PVC/PE tubing—was subcutaneous down to the point of emergence on the back.

The monkeys were equipped with nylon jackets and flexible-cable tethers for drug administration. The two lengths of PE-50 encased in silicone tubing, from the two ends of the implant, provided for safe subcutaneous passage and also continued up the flexible tubing fastened to the monkey's nylon jacket and then into the rotating shaft of the rotometer above the cage, where they were led out through a hole in the shaft and connected via three-way stopcocks to a pair of 1-cc syringes fastened to the shaft to rotate along with it and along with the monkey below. The stopcocks permitted repeated emptying and filling of the syringes without disturbing the continuity of fluid in the access tubing that passed through the brain. The "outflow" syringe, connected to the posterior-cranial PE-50 tubing, was mounted upside down; during replacement of fluid in the access tubing, its plunger was interlocked with that of the "inflow" syringe just below on the shaft, to provide a balanced push-pull action and to avoid any unnecessary pressurizing or decompression of the fluid in the access tubing in the brain.

Adaptations in the tether system enabled it to serve as the drive-shaft for baboon rotometry as well as the conduit for drug administration. The cable was strengthened and stiffened by a wire-braid wrapping. The connection to the jacket for Monkey 2 was also set at a right angle and reinforced with a sturdy stainless-steel housing that prevented its destruction, after the loss of several earlier implementations due to the challenging motor behavior of this monkey. A channel in the wire mesh of the top of the cage, from the middle to the front, allowed for transferring the monkey, tether cable, and syringe/rotometer shaft as a single unit from one cage to another, to permit removing and cleaning the cages.

Rotational behavior was monitored continuously by rotometer methods, and the effects of lesions and implants were studied without the peripheral administration of CNS stimulant drugs. The behavior of lesioned animals normally involves some contralateral turning as well as ipsilateral, but the distribution of this "paradoxical" turning was not evenly spaced through the day. In both baboons, the greatest amount of paradoxical turning occurred during an active period in the middle of the day, for the 2–3 hours preceding feeding. Drug applications via the access tubing were therefore made in the morning, before this period.

A concentrated solution of apomorphine (0.0045M) was placed in the access tubing of Monkey 1 on two occasions, separated by 11 days. The first application consisted of filling the entire length of tubing (approximately 7 feet) with a concentrated apomorphine solution by the push-pull action of the syringes described above, then obstructing the outflow line and slowly pushing in 0.25 cc under pressure. The only patency in the tubing was the 19-mm permselective portion in the putamen, the brain structure most affected by the MPTP lesion and by Parkinson's disease in humans. The second application was more gentle, by diffusion alone, using the same high concentration of apomorphine, but without any pressurized injection. A break in the line in the flexible cable a few days after the second treatment prevented further testing of Monkey 1. Treatments in Monkey 2 began with a low dose of apomorphine 1/100 of the original dose. Fluid at this concentration was placed in the implant on the second day and again on the third day after the surgery. A higher dose (1/50 original) was placed on each of the next three days, then 1/20, 1/10, and 1/5 for two days each, and finally the full concentration for the final day, after which saline was returned to the line.

Two days later, on the premise that oxidized apomorphine might be occluding the molecular pores in the tubing, the pressure resisting infusion of fluid was tested by releasing the syringe needle on the upper lead from its syringe and stopcock, allowing fluid to infuse under the pressure of gravity, and by measuring the rate at which the fluid level dropped in the tubing, over a distance of 3 mm. By comparing this to the rate of fall under similar conditions in vitro with the patent span of tubing resting in saline at atmospheric pressure, an estimate of "circumtubular" pressure was calculated. Subsequently, an attempt was made to clear potential occlusion of the pores with a solubilizing agent, dimethyl sulfoxide (DMSO). DMSO (10% in normal saline) was introduced and left in the tubing for 30 minutes, then replaced with saline. The drop-rate was then re-measured, then DMSO was introduced again for another 60 minutes, and the drop-rate was measured a third time.

Nine days after the last apomorphine exposure, dopamine and tranylcypromine were presented together in solution and left in place without replacement for the next four days. At this point a break in one line outside the brain required that behavioral experiments be terminated.

The tubing implanted in Monkey 2 was visualized by MR imaging after behavioral experiments were terminated. Series of images were made just before and just after the application of gadolinium (3 parts in 50 parts saline), as well as 25 min and 50 min after gadolinium. The tubing implanted in Monkey 1 was also visualized, but without gadolinium.

The portion of the brain containing the tubing was fixed by immersion in formalin for 24 h, then cryoprotected by immersion in 30% sucrose for 3 days. Coronal frozen sections were cut throughout the course of the implant, and Nissl sections and immunohistochemical sections (tyrosine hydroxylase and glial fibrillary acidic protein) were prepared at approximately 1-mm intervals by methods previously described.

Figure 11A:
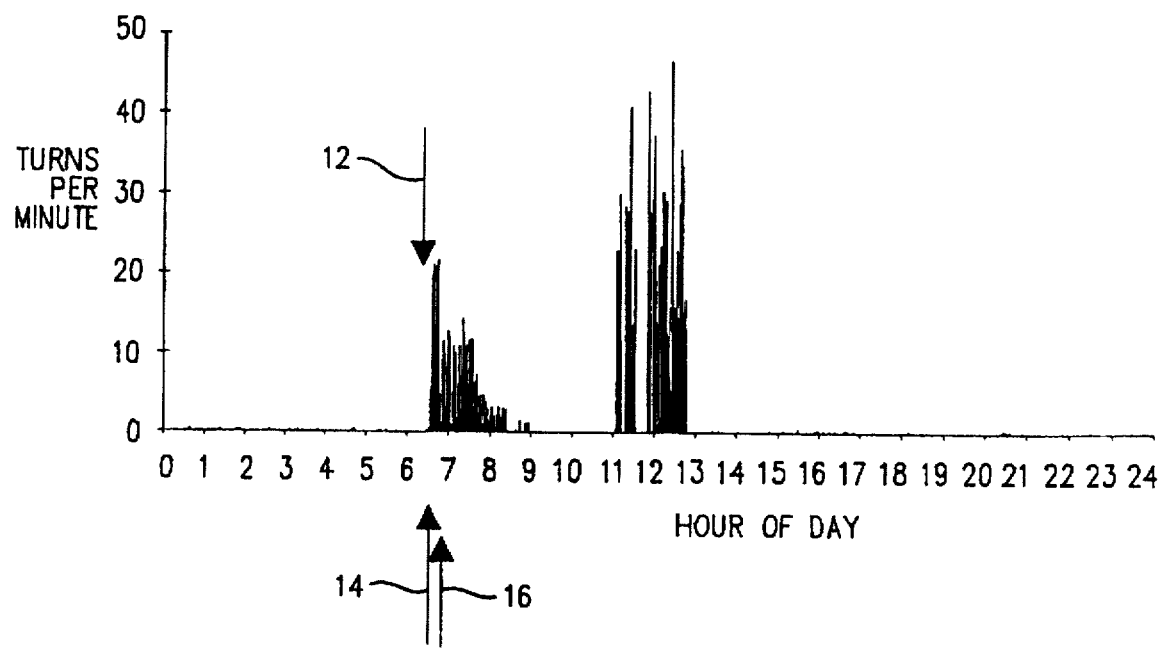
FIG. 11A–B depict quantitative records of turns made contralateral to the side of a lesion and an implant, in response to drug treatment via the implant. The number of turns (Y-axis) completed each minute throughout the 24 hours of the day (X-axis) is indicated by a line of appropriate height.

The pressurized infusion of 250 µl of concentrated apomorphine had both acute and lasting effects in Monkey 1. The monkey almost immediately (2 min) began turning in the direction contralateral to the side of the lesion and the implant. This turning was unlike the typical contralateral turning for this monkey. Typical contralateral turning was performed bipedally or on all fours with the face near the walls of the cage, directed straight ahead or toward the ipsilateral side. The "topography" of the apomorphine-induced turning behavior, on the other hand, was comparable with that of turning induced in lesioned rats by peripherally administered apomorphine. The face was usually directed toward the contralateral shoulder. Turns were fast and "tight" and were made with minimal use of the hindlimbs, especially the contralateral hindlimb, which was used as a pivot at an early point, within 3 min of drug infusion. Later on, the hindlimbs more often were flexed or collapsed. Some of the behavior could be described as "ischial spinning", mixed with bursts of bipedal spins or jumps (within 5 min). Turning was less continual by this time, and most turns were single full rotations, explosive movements at intervals of 5–40 seconds, with a prominent weaving and crouching of the upper body between turns. These effects were so intense that the apomorphine was replaced with saline (17 minutes after treatment). During this procedure bouts of multiple ischial spins occurred (21 minutes after treatment), and such bouts and isolated rapid turns continued to occur for about an hour, gradually becoming slower and more often aborted to a head-and-shoulder gesture in that period of time. FIG. 11A (apomorphine under pressure) represents contralateral turns per minute for each minute through the day, with the time marked on the x-axis in hours.

Figure 11B:
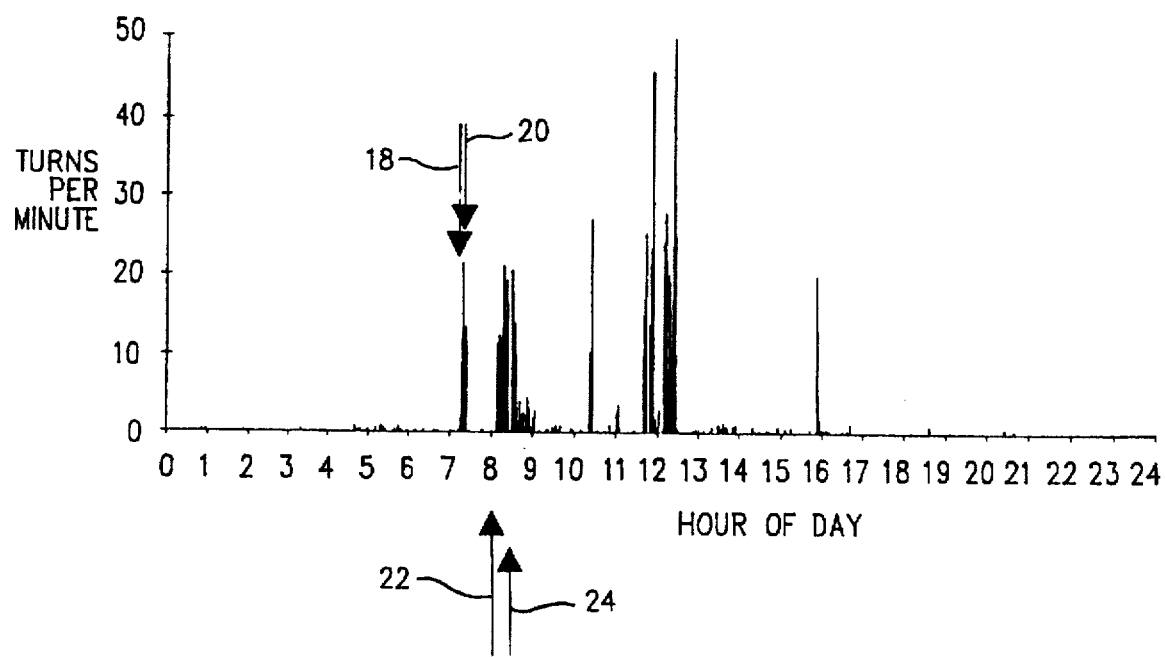

In a second trial after 11 days to assure recovery, introduction of apomorphine at the same high concentration, but without pressurized infusion, also produced ischial spinning of a similar topography and latency of onset. The rotation was somewhat less "explosive" in character, but more continual; it involved less ataxic weaving of the upper body, but more scratching, which made use of the affected contralateral limb, which was not normally used in this manner. Again, effects appeared so rapidly and intensely that an attempt was made to terminate them by replacing apomorphine in the tubing with saline (18 min after treatment). In addition, 28 minutes later, the saline was replaced by the dopamine antagonist droperidol (0.0053M). Immediately after this exchange the monkey became very inactive. Although the droperidol was left in the tubing for 7 hours, however, it did not prevent the midday bout of contralateral turning that was typical for this monkey. FIG. 11B (apomorphine by diffusion) shows the contralateral turns in response to the treatment.

Monkey 2 was implanted twice. The stabilization of the tubing as it emerged from the cranium after the first implantation was inadequate because Vetbond was omitted during preparation of the posterior acrylic pad, which quickly broke loose, interrupting the line. Examination of the preparation and removal of the implant after this occurrence, under inevitably non-sterile conditions, may have led to bacterial contamination of cranial and brain tissue, which was treated prophylactically with antibiotic. Six weeks later, a second implant was introduced, with the pads stabilized with additional Vetbond between the cranium and the acrylic pad as described above. This implant remained serviceable for five weeks.

For a 12-day period beginning two days after the second implant surgery, the fluid in the tubing was changed every day, gradually increasing the dose of apomorphine from 1% to 100% of the previous 0.0045M concentration. From a starting point of 5–10% contralateral turning per day, the monkey reached an average of 21% contralateral turning over the last week of this period, under the influence of the higher doses, with a peak day at 35%. Replacement of the highest concentration with saline alone, after this period, resulted in a gradual decline back to baseline over 7–8 days.

During this period the pressure resisting an infusion of fluid was found to be well beyond the normal limits of intracranial pressure. Given the possibility that the molecular pores in the tubing had been largely occluded by chronic exposure to oxidized apomorphine, an attempt was made to clear any such occlusion. The solubilizing agent DMSO was administered, first for 30 minutes, and then for 60 minutes, and the drop-rate increased after each exposure.

After a total of nine days at about 10% contralateral turning, including the day of these pressure tests, a solution of dopamine itself (0.045M) was placed in the implanted tubing, along with tranylcypromine (0.0188M), a monoamine oxidase inhibitor to delay the metabolic disposal of the dopamine. The day after this change, the monkey showed 31% contralateral turning, but returned on the following day to baseline levels. The fluid was not exchanged and the intactness of the line was not examined until four days after placement of the dopamine/tranylcypromine solution, at which time the outflow line was found to be interrupted.

Histological examination of Monkey 1 indicated the placement of the tubing in the medial putamen, internal capsule, and anterior caudate nucleus throughout most of the length of the neostriatum, and indicated that the lesion had greatly reduced TH immunoreactivity in the striatal dopamine terminal areas. GFAP immunoreactivity indicated activation of glial cell somata in the vicinity of the tubing, where labeled cells were approximately three times more common than in areas distant from the tubing. The trabecular walls of the tubing which surround the inner permselective membrane were marked at some points by intrusions of labeled material. Control sections reacted with normal rabbit serum as the primary, or with vehicle alone without any primary antibody, displayed different patterns of peroxidation in the walls of the tubing. It was not possible by LM observation alone to determine to what extent glial extensions had invested the walls of the tubing, or to what extent the "labeled" objects consisted of oxidized apomorphine. It is interesting to note, however, that every section subjected to free-floating immunohistochemical processing consisting of more than 24 hours of shaking still retained its PAN-PVC tubing cross-section.

In vivo MRI evaluation of the tubing in Monkey 2 indicated that its course through the brain closely matched the planned trajectory. The tubing when filled with saline appeared as a few dark voxels, an absence of signal similar to the lateral ventricle. The introduction of "caged" gadolinium into the tubing resulted in a strong signal within the tubing, providing a detailed assessment of its trajectory. The second and third MRI views at 25 and 50 minutes after introduction of gadolinium indicated a gradual spread of signal from the body of the tubing into the surrounding tissue. This could be observed by close comparison of the original pictures, but was more clearly evident from subtractions performed within the Adobe Photoshop environment.

Histological examination of Monkey 2 indicated the presence of two tubular implants extending through most of the length of the putamen. It was possible to identify the later implant in the more lateral of these two positions, corresponding to the gadolinium-marked tubing of the in vivo MRI evaluation, and the earlier implant, which was never used, in the position 2–3 mm more medial. The later implant, which was used chronically for applying dopamine and apomorphine, and acutely for applying DMSO and gadolinium, was associated with evidence of an intense local inflammatory response, but the medial implant did not appear to be directly associated with this. A reasonable interpretation would be that the presence of the tubular implant itself was innocuous, but that one or more of the substances applied via the tubing is capable of causing inflammation in the concentrations employed.

In vivo evaluation of the parahippocampal implant in Monkey 3 by MRI indicated that the tubing followed a course very similar to that planned. The trajectory followed a straight and nearly vertical path of entry posteriorly, as planned, down to a point just behind the anterior enlargement of the inferior horn of the third ventricle, then passed under the ventricle and hippocampus, in the parahippocampal area, to an anterior point just medial to the ventricle, from which it proceeded up again along a straight but angled course to the cortical surface. The ventricle itself appeared to be involved minimally if at all.

What is claimed is:

1. A method for stereotactically implanting a foreign material along a predetermined compound path through a desired region of parenchymal tissue in a host, comprising:
   identifying the predetermined compound path which includes at least one arcuate segment through the host, the predetermined compound path entering the host at an entry point, traversing the desired region of parenchymal tissue without substantially following along existing tissue surfaces or natural channels in the body, and exiting at an exit point different from the entry point;
   inserting a guide-tube cannula through a surface of the host along a first portion of the predetermined compound path;
   advancing at least a first extendable element selected from the group consisting of a cannula and a wire, preformed to match at least a second portion of the predetermined compound path, through the guide-tube cannula into the host along at least the second portion of the predetermined compound path until the end portion of the first or subsequent extendable element emerges from the host at an exit point different from the entry point;
   attaching the foreign material to the end portion protruding from said exit point;
   withdrawing each extendables element through the host in reverse order to implant the foreign material in the host along the predetermined compound path.

2. The method of claim 1, wherein the foreign material is indirectly attached to the final extendable element.

3. The method of claim 1, wherein the at least first extendable element is comprised of nitinol.

4. The method of claim 1, wherein the at least first extendable element is round in cross-section.

5. The method of claim 1, wherein the compound trajectory is determined by a computer.

6. The method of claim 1, wherein the foreign material includes a temperature-control device.

7. The method of claim 1, wherein the foreign material includes an electrode or electric device.

8. The method of claim 1, wherein the foreign material is a catheter.

9. The method of claim 8, wherein the catheter is semipermeable.

10. The method of claim 9, wherein the catheter comprises the copolymer polyacrylonitrile-polyvinylchloride.

11. The method of claim 9, wherein fluid withdrawn from the catheter is analyzed.

12. The method of claim 9, wherein cells are present in the catheter.

13. The method of claim 12, wherein the cells are cells from the host that have been transfected to express a therapeutic compound.

14. The method of claim 9, wherein the catheter is fluidly connected to a source of therapeutic compound or biological agent.

15. The method of claim 14, wherein the catheter is adjustably filled with the therapeutic compound or biological agent.

16. The method of claim 15, wherein the therapeutic compound is for treating a tumor.

17. The method of claim 15, wherein the therapeutic compound is for treating epilepsy, schizophrenia, Alzheimer's disease, depression, spinal cord trauma or Parkinson's disease.

18. The method of claim 17, wherein the therapeutic compound is a dopamine agonist.

19. The method of claim 12, wherein the therapeutic compound is a neurotrophic factor.

20. A device having a proximal end and a distal end for percutaneous localization of a foreign material in a body, comprising:
   a base collar mount having a proximal surface, a distal surface rigidly affixed to at least one perpendicular guide rail, and a channel between the upper and lower surfaces through which channel a guide-tube cannula extends from the proximal surface of the base collar;
   a first movable collar mount slidably located on each guide rail rigidly affixed to a curved first extendable element which is a cannula having a proximal end and a distal end, wherein the distal end of the first extendable cannula is affixed to the first movable collar in a channel through the first movable collar and the proximal portion of the first extendable cannula is in the guide-tube cannula; and
   a second movable collar mount slidably located on each guide rail rigidly affixed to a second extendable element selected from the group consisting of a cannula and a wire having a proximal end and a distal end, wherein the distal end of the second extendable element is affixed to the second movable collar in a channel through the second movable collar and the proximal portion of the second extendable element is in the first extendable element;
   wherein proximal sliding of the first movable collar will extend the first extendable element through the proximal end of the guide-tube cannula and proximal sliding of the second movable collar will extend the second extendable cannula or wire through the proximal end of the first extendable cannula.

21. The device of claim 20, further comprising a first slide stop for the first movable collar that will limit the proximal distance of sliding of the first movable collar on at least one guide rail.

22. The device of claim 21, wherein the first slide stop is rigidly affixed to the first movable collar.

23. The device of claim 21, wherein the first slide stop is rigidly affixed to at least one guide rail.

24. The device of claim 20, wherein the second extendable element is straight.

25. The device of claim 20, wherein the second extendable element is curved.

26. The device of claim 20, wherein the second extendable element is a cannula, further comprising at least a third movable collar mount slidably located on each guide rail, the at least third movable collar mount rigidly affixed to a third extendable element selected from the group consisting of a cannula and a wire having a proximal end and a distal end, wherein the distal end of the third extendable element is affixed to the at least third movable collar in a channel through the third movable collar and the proximal portion of the third extendable element is in the second extendable element;

wherein proximal sliding of the third movable collar will extend the third extendable element through the proximal end of the second extendable element.

27. The device of claim 20, wherein the first and second extendable elements comprise nitinol.

28. A method for percutaneous placement of foreign material in a desired location in a body, comprising:

positioning a device as in claim 20 at a predetermined location and orientation over the body;

advancing the guide-tube cannula into the body, covering an original predetermined distance;

advancing the first extendable element into the body, covering a first additional predetermined distance; and introducing the foreign material through the first extendable element to the desired location in the body.

29. The method of claim 28, wherein the foreign material is a catheter.

30. The method of claim 28, wherein the foreign material is a pharmaceutical compound.

31. The method of claim 28, further comprising the step of identifying the desired position in the body by an imaging technique.

32. The method of claim 31, wherein the imaging technique is magnetic resonance imaging.

33. The method of claim 12, wherein the imaging technique is computerized tomography.

34. The method of claim 12, wherein the imaging technique is ultrasound.

35. The device of claim 20, wherein the second extendable element is a cannula and the foreign material is a fluid that is ejected into a body from the end of the second extendable element.

36. The device of claim 20, wherein the foreign material comprises an elongated solid object fastened to the end of the second extendable element and drawn into a body by retracting said element.

37. A method for percutaneous placement of foreign material in a desired location in a body, comprising the steps of:

positioning a device as in claim 20 at a predetermined location and orientation over the body;

advancing the guide-tube cannula into the body, covering an original predetermined distance;

advancing the first extendable element into the body, covering a first additional predetermined distance;

advancing the second extendable element, which is a cannula, covering at least a second predetermined distance; and introducing the foreign material through the second extendable element to the desired location in the body.

38. A kit for placement of a catheter in a compound trajectory in a host, comprising:

a device having a base collar mount having a proximal surface, a distal surface rigidly affixed to at least one perpendicular guide rail, and a channel between the upper and lower surfaces through which channel a guide-tube cannula extends from the proximal surface of the base collar;

a first movable collar mount slidably located on each guide rail rigidly affixed to a curved first extendable element which is a cannula having a proximal end and a distal end, wherein the distal end of the first extendable element is affixed to the first movable collar in a channel through the first movable collar and the proximal portion of the first extendable element is in the guide-tube cannula; and a second movable collar mount slidably located on each guide rail rigidly affixed to a second extendable element selected from the group consisting of a cannula or wire having a proximal end and a distal end, wherein the distal end of the second extendable element is affixed to the second movable collar in a channel through the second movable collar and the proximal portion of the second extendable element is in the first extendable element;

wherein proximal sliding of the first movable collar will extend the first extendable element through the proximal end of the guide-tube cannula and proximal sliding of the second movable collar will extend the second extendable element through the proximal end of the first extendable element; and a catheter adapted to be coupled to an end of the second extendable element for implantation.

39. The kit of claim 38, wherein the catheter is semipermeable.

40. The kit of claim 39, wherein the catheter comprises the copolymer polyacrylonitrile-polyvinylchloride.

41. The kit of claim 38, further comprising at least one implantable pump.

* * * * *

UNITED STATES PATENT AND TRADEMARK OFFICE
CERTIFICATE OF CORRECTION

PATENT NO. : 5,788,713
DATED : August 4, 1998
INVENTOR(S) : MARK DUBACH and YVES NIEVERGELT It is certified that error appears in the above-identified patent and that said Letters Patent is hereby corrected as shown below:

On the Title page, in section [75], please correct the inventor's name "Yves Nlevergelt" to --Yves Nievergelt--.

Signed and Sealed this

Twenty-fourth Day of November, 1998

Attest:

BRUCE LEHMAN

Attesting Officer

Commissioner of Patents and Trademarks